US012729375B2

(12) United States Patent
Andersen

(10) Patent No.: US 12,729,375 B2
(45) Date of Patent: Sep. 8, 2026

(54) ALPHA-AMYLASE VARIANTS

(71) Applicant: NOVOZYMES A/S, Bagsvaerd (DK)

(72) Inventor: Carsten Andersen, Vaerloese (DK)

(73) Assignee: NOVOZYMES A/S, Bagsvaerd (DK)

( * ) Notice: Subject to any disclaimer, the term of this patent is extended or adjusted under 35 U.S.C. 154(b) by 649 days.

(21) Appl. No.: 18/044,836

(22) PCT Filed: Oct. 6, 2021

(86) PCT No.: PCT/EP2021/077513
§ 371 (c)(1),
(2) Date: Mar. 10, 2023

(87) PCT Pub. No.: WO2022/074037
PCT Pub. Date: Apr. 14, 2022

(65) Prior Publication Data

US 2025/0346879 A1 Nov. 13, 2025

(30) Foreign Application Priority Data

Oct. 7, 2020 (EP) .................................... 20200473

(51) Int. Cl.
*C12N 9/26* (2006.01)
*C11D 3/386* (2006.01)

(52) U.S. Cl.
CPC ............ *C12N 9/2414* (2013.01); *C11D 3/386* (2013.01); *C11D 2111/14* (2024.01); *C12Y 302/01001* (2013.01)

(58) Field of Classification Search
CPC ... C12N 9/2414; C11D 3/386; C11D 2111/14; C12Y 302/01001
See application file for complete search history.

(56) References Cited

U.S. PATENT DOCUMENTS

| | | | |
|---|---|---|---|
| 2009/0263881 A1 | 10/2009 | Borchert et al. |
| 2017/0240877 A1 | 8/2017 | Andersen et al. |

FOREIGN PATENT DOCUMENTS

| | | | |
|---|---|---|---|
| EP | 2726500 A2 | 1/2013 |
| EP | 3421595 A1 | 1/2019 |
| WO | 95/26397 A1 | 10/1995 |
| WO | WO 2015/044448 A1 * | 4/2015 |

OTHER PUBLICATIONS

Banerjee et al., Improving enzymes for biomass conversion: A basic research perspective. Bioenerg. Res., 2010, vol. 3: 82-92. (Year: 2010).*

Broun et al., Catalytic plasticity of fatty acid modification enzymes underlying chemical diversity of plant lipids. Science, 1998, vol. 282: 1315-1317 (Year: 1998).*

Chica et al., Semi-rational approaches to engineering enzyme activity: combining the benefits of directed evolution and rational design. Curr. Opi. Biotechnol., 2005, vol. 16: 378-384. (Year: 2005).*

Devos et al., Practical limits of function prediction. Proteins: Structure, Function, and Genetics. 2000, vol. 41: 98-107. (Year: 2000).*

Seffernick et al., Melamine deaminase and Atrazine chlorohydrolase: 98 percent identical but functionally different. J. Bacteriol., 2001, vol. 183 (8): 2405-2410. (Year: 2001).*

Sen et al., Developments in directed evolution for improving enzyme functions. Appl. Biochem. Biotechnol., 2007, vol. 143: 212-223. (Year: 2007).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

* cited by examiner

*Primary Examiner* — Ganapathirama Raghu
(74) *Attorney, Agent, or Firm* — Yoshimi D. Barron

(57) ABSTRACT

The present invention relates to alpha-amylase variants. The present invention also relates to polynucleotides encoding the variants; nucleic acid constructs, vectors, and host cells comprising the polynucleotides; and methods of using the variants.

13 Claims, No Drawings

Specification includes a Sequence Listing.

ALPHA-AMYLASE VARIANTS

CROSS-REFERENCE TO RELATED APPLICATIONS

This application is a 35 U.S.C. 371 national application of international application no. PCT/EP2021/077513 filed Oct. 6, 2021, which claims priority or the benefit under 35 U.S.C. 119 of European application no. 20200473.5 filed Oct. 7, 2020. The disclosure of each application is fully incorporated herein by reference.

REFERENCE TO A SEQUENCE LISTING

This application contains a Sequence Listing in computer readable form, which is incorporated herein by reference. The name of the file containing the Sequence Listing is SQ. Txt, which was created on Aug. 28, 2023 and has 64,861 bytes.

FIELD OF THE INVENTION

The present invention relates to variants of an alpha-amylase, polynucleotides encoding the variants, and methods of producing the variants.

BACKGROUND OF THE INVENTION

Alpha-amylases (alpha-1,4-glucan-4-glucanohydrolases, E. C. 3.2.1.1) constitute a group of enzymes, which catalyses hydrolysis of starch and other linear and branched 1,4-gluosidic oligo- and polysaccharides.

There is a long history of industrial application of alpha-amylases in e.g. detergent, baking, brewing, starch liquefaction and saccharification such as in preparation of high fructose syrups or as part of ethanol production from starch. Many of these and other applications of alpha-amylases utilize alpha-amylases derived from microorganisms, in particular bacterial alpha-amylases.

Among the first bacterial alpha-amylases to be used were an alpha-amylase from *B. licheniformis*, also known as Termamyl, which has been extensively characterized and the crystal structure has been determined for this enzyme. Alkaline amylases, such as the alpha-amylase derived from *Bacillus* sp. as disclosed in WO 95/26397, form a particular group of alpha-amylases that have found use in detergents.

Many of these known bacterial amylases have been modified in order to improve their functionality in a particular application.

Thus, it is an object of the present invention to provide variant polypeptides having alpha-amylase activity that exhibit an improved property, such as wash performance, when compared to the parent alpha amylase.

The present invention provides variant polypeptides having alpha-amylase activity and improved property compared to its parent alpha amylase.

SUMMARY OF THE INVENTION

The present invention relates to an alpha-amylase variant of a parent alpha-amylase comprising a) a deletion and/or a substitution at two or three or four positions corresponding to positions R181, G182, H1183 and G184, and b) an alteration at one or more positions corresponding to positions: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116,118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, 485, using SEQ ID NO: 1 for numbering; and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4, 5, 6, 7, 8, 9, 10, 11, 12 or 13, and wherein said variant has alpha-amylase activity and wherein the alpha-amylase variant has an improved property relative to said parent alpha-amylase of SEQ ID NO: 1 and/or SEQ ID NO: 2.

The present invention also relates to an alpha-amylase variant comprising a) a pairwise deletion of the amino acids corresponding to positions H183*+G184* and b) an alteration at one or more positions corresponding to positions: H1, H2, N3, G4, T5, M9, Y16, L17, N22, H23, N25,N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311, 1312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, I389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4, 5, 6, 7, 8, 9, 10, 11, 12 or 13, and wherein said variant has alpha-amylase activity and wherein the alpha-amylase variant has an improved property relative to said parent alpha-amylase of SEQ ID NO: 1 and/or SEQ ID NO: 2.

The present invention also relates to a method of producing an alpha-amylase variant, comprising (a) cultivating the host cell of the invention under conditions suitable for expression of the variant, and (b) recovering the variant.

The present invention further relates to a method of obtaining an alpha-amylase variant of a parent alpha-amylase comprising the steps of: a) introducing a deletion and/or a substitution at two or three or four positions corresponding to positions R181, G182, H183 and G184, and b) introducing an alteration at one or more positions corresponding to positions: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116,118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, 485, using SEQ ID NO: 1 for numbering; said method thereby providing an alpha-amylase variant of said parent alpha-amylase, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4, 5, 6, 7, 8, 9, 10, 11, 12 or 13, and wherein said variant has alpha-amylase activity and wherein the alpha-amylase variant has an improved property relative to said parent alpha-amylase.

Definitions

In accordance with this detailed description, the following definitions apply. Note that the singular forms “a,” “an,” and “the” include plural references unless the context clearly dictates otherwise.

Reference to “about” a value or parameter herein includes aspects that are directed to that value or parameter per se. For example, description referring to “about X” includes the aspect “X”.

Unless defined otherwise or clearly indicated by context, all technical and scientific terms used herein have the same meaning as commonly understood by one of ordinary skill in the art to which this invention belongs.

A-, B- and C-domains: The structure of alpha-amylases comprises three distinct domains A, B and C, see, e.g., Machius et al., 1995, J. MoL. Biol. 246: 545-559. The term “domain” means a region of a polypeptide that in itself forms a distinct and independent substructure of the whole molecule. Alpha-amylases consist of a beta/alpha-8 barrel harboring the active site residues, which is denoted the A-domain, a rather long loop between the beta-sheet 3 and alpha-helix 3, which is denoted the B-domain (together; “A and B domain”), and a C-domain and in some cases also a carbohydrate binding domain (e.g., WO 2005/001064; Machius et al., supra).

The domains of an alpha-amylase can be determined by structure analysis such as using crystallographically techniques. An alternative method for determining the domains of an alpha-amylase is by sequence alignment of the amino acid sequence of the alpha-amylase with another alpha-amylase for which the domains have been determined. The sequence that aligns with, e.g., the C-domain sequence in the alpha-amylase for which the C-domain has been determined can be considered the C-domain for the given alpha-amylase.

A and B domain: The term “A and B domain” as used herein means these two domains taken as one unit, whereas the C domain is another unit of the alpha-amylases. Thus, the amimo acid sequence of the “A and B domain” is understood as one sequence or one part of a sequence of an alpha-amylase comprising an “A and B domain” and other domains (such as the C domain). As used herein, the “A and B domain” of an alpha-amylase corresponds to amino acids 1-399 of SEQ ID NO: 1.

Alpha-Amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides. In one aspect, the alpha-amylase variants of the present invention has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

Alpha-amylase activity: The term ‘alpha-amylase activity’ as used herein, refers to the activity of an alpha-amylase wherein the activity is determined according to the procedure described in the Examples. The alpha-amylase activity may be determined according to a method using the micro swatch assay which is described in the Examples.

Amino acid: The term ‘amino acid’ as used herein, refers to the standard twenty genetically-encoded amino acids and their corresponding stereoisomers in the ‘d’ form (as compared to the natural ‘I’ form), omega-amino acids other naturally-occurring amino acids, unconventional amino acids (e.g. $\alpha,\alpha$-disubstituted amino acids, N-alkyl amino acids, etc.) and chemically derivatised amino acids. Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

When an amino acid is being specifically enumerated, such as 'alanine' or 'Ala' or 'A', the term refers to both I-alanine and d-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid. In one embodiment, the polypeptides of the invention comprise or consist of I-amino acids.

Catalytic Domain: The term "catalytic domain" means the region of an enzyme containing the catalytic machinery of the enzyme.

C domain: As used herein, the "C domain" of an alpha-amylase corresponds to amino acids 400-485 of SEQ ID NO: 17. Thus, the C domain of an alpha amylase may be found by alignment of said alpha amylase with the alpha amylase of SEQ ID NO: 1. The part of said alpha amylase that aligns with amino acids 400-485 of SEQ ID NO: 1 is according to the present invention "the C domain" of the alpha amylase.

cDNA: The term "cDNA" as used herein, refers to a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" as used herein, refers to a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" as used herein, refers to nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, pro-peptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Corresponding to: The term "corresponding to" as used herein, refers to a way of determining the specific amino acid of a sequence wherein reference is made to a specific amino acid sequence. E.g. for the purposes of the present invention, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the sequence as set forth in SEQ ID NOs: 1, 2, 3, 4 5, 6, 7, 8, 9, 10, 11, 12 or 13 or any other sequence listed herein, has been described elsewhere herein. Alternative alignment methods may be used and are well-known for the skilled person.

Dish washing composition: The term "dish washing composition" as used herein, refers to all forms of compositions for cleaning hard surfaces. The present invention is not restricted to any particular type of dish wash composition or any particular detergent. Thus, in one embodiment, the dish washing composition is a liquid dish washing composition, a powder dish washing composition, wherein the composition may optionally be in the form of a unit dose.

Enzyme Detergency benefit: The term "enzyme detergency benefit" used herein, refers to the advantageous effect an enzyme may add to a detergent compared to the same detergent without the enzyme. Important detergency benefits which can be provided by enzymes are stain removal with no or very little visible soils after washing and/or cleaning, prevention or reduction of re-deposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of re-deposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

Expression: The term "expression" as used herein, refers to any step involved in the production of a variant including, but not limited to, transcription, post-transcriptional modification, translation, post-translational modification, and secretion.

Expression vector: The term "expression vector" as used herein, refers to a linear or circular DNA molecule that comprises a polynucleotide encoding a variant and is operably linked to control sequences that provide for its expression.

Fragment: The term "fragment" as used herein, refers to a polypeptide having one or more (e.g., several) amino acids absent from the amino and/or carboxyl terminus of the mature polypeptide of any one of the parent sequences herein disclosed, such as SEQ ID NOs: SEQ ID NOs: 1, 2, 3, 4, 5, 6, 7, 8, 9, 10, 11, 12 or 13; wherein the fragment has alpha-amylase activity. In one aspect, a fragment contains at least 200 contiguous amino acid residues of SEQ ID NOs: 1, 2, 3, 4, 5, 6, 7, 8, 9, 10, 11, 12 or 13, for example at least 300 contiguous amino acid residues, or at least 350 contiguous amino acid residues, or at least 400 contiguous amino acid residues, or at least 450 contiguous amino acid residues of SEQ ID NOs: 1, 2, 3, 4 5, 6, 7, 8, 9, 10, 11, 12 or 13.

High Stringency: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Hard surface cleaning: The term "hard surface cleaning" as used herein, refers to cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics Host cell: The term "host cell" as used herein, refers to any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" is defined herein as a characteristic associated with a variant that is improved compared to the parent alpha-amylase. Such improved properties include, but are not limited to, increased amylolytic activity, increased catalytic efficiency, increased catalytic rate, increased chemical stability, increased oxidation stability, increased pH activity, increased pH stability, increased specific activity, increased substrate binding, increased substrate cleavage, increased substrate specificity, increased substrate stability, increased surface properties, increased thermal activity, and increased thermostability and increased wash performance such as soil performance e.g. performance to starch containing soils, stain removal, anti-greying, stability e.g. thermostability, pH stability, or stability in the presence of builders, including chelant, stability in powder, liquid or gel detergent formulations or dishwashing compositions, altered temperature-dependent performance and activity profile, pH activity, substrate specificity, product specificity, and chemical stability. The improved property may be any of those herein defined and described, such as increased specific activity.

Improved Wash Performance: The term "improved wash performance" is defined herein as displaying an alteration of the wash performance of an amylase of the present invention relative to the wash performance of the parent alpha-amylase. The alteration may e.g. be seen as increased stain removal. The wash performance is improved if the Improvement Factor (IF) is at least 1.1, at least 1.2, at least 1.3.

Isolated: The term "isolated" as used herein, refers to a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Isolated Polynucleotide: The term "isolated polynucleotide" means a polynucleotide that is modified by the hand of man. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Mature polypeptide: The term "mature polypeptide" as used herein, refers to means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" as used herein, refers to a polynucleotide that encodes a mature polypeptide having alpha-amylase activity.

Modification: The term "modification", in the context of the polypeptides of the invention, means that one or more amino acids within the reference amino acid sequence (i.e. SEQ ID NOs: 1, 2, 3, 4 5, 6, 7, 8, 9, 10, 11, 12 or 13) are altered by substitution with a different amino acid, by insertion of an amino acid or by deletion, preferably by at least one deletion. The terms "modification", "alteration", and "mutation" may be used interchangeably and constitute the same meaning and purpose.

Medium Stringency: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Mutant: The term "mutant" means a polynucleotide encoding a variant.

Nucleic acid construct: The term "nucleic acid construct" as used herein, refers to a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" as used herein, refers to a configuration in which a control sequence is placed at an appropriate position relative to the coding sequence of a polynucleotide such that the control sequence directs expression of the coding sequence.

Parent or parent alpha-amylase: The term "parent" alpha-amylase as used herein means an alpha-amylase to which alterations are made to produce the variant alpha-amylases of the present invention. This term also refers to the polypeptide with which a variant of the invention is compared. The parent may be a naturally occurring (wild type) polypeptide, or it may even be a variant thereof, prepared by any suitable means. For instance, the parent protein may be a variant of a naturally occurring polypeptide which has been modified or altered in the amino acid sequence. Thus, the parent alpha-amylase may have one or more (or one or several) amino acid substitutions, deletions and/or insertions. Thus, the parent alpha-amylase may be a variant of a parent alpha-amylase. A parent may also be an allelic variant which is a polypeptide encoded by any of two or more alternative forms of a gene occupying the same chromosomal locus. The term "parent" or "parent alpha-amylase" as used herein, refers to the alpha-amylase of SEQ ID NOs: 1, 2, 3, 4, 5, 6, 7, 8, 9, 10, 11, 12 or 13, or any alpha-amylase having at least 60% sequence identity to any of the polypeptides of SEQ ID NOs: 1, 2, 3, 4, 5, 6, 7, 8, 9, 10, 11, 12 or 13. The parent amylase may also be a polypeptide comprising a fragment of SEQ ID NOs: 1, 2, 3, 4, 5, 6, 7, 8, 9, 10, 11, 12 or 13.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. MoL. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used may be gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

Alternatively, the parameters used may be gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" as used herein, refers to a polynucleotide having one or more (e.g., several) nucleotides absent from the 5' and/or 3' end of a mature polypeptide coding sequence; wherein the subsequence encodes a fragment having alpha-amylase activity.

Textile: The term "textile" refers to woven fabrics, as well as staple fibres and filaments suitable for conversion to or use as yarns, woven, knit, and non-woven fabrics. The term encompasses yarns made from natural, as well as synthetic (e.g., manufactured) fibres. The term, "textile materials" is a general term for fibres, yarn intermediates, yarn, fabrics, and products made from fabrics (e.g., garments and other articles).

Textile care benefit: The term "textile care benefits", as used herein, is defined as not being directly related to catalytic stain removal or prevention of re-deposition of soils, are also important for enzyme detergency benefits. Examples of such textile care benefits are prevention or reduction of dye transfer from one textile to another textile or another part of the same textile (an effect that is also termed dye transfer inhibition or anti-backstaining), removal of protruding or broken fibers from a textile surface to decrease pilling tendencies or remove already existing pills or fuzz (an effect that also is termed anti-pilling), improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species."

Wild-Type Enzyme: The term "wild-type" alpha-amylase denotes an alpha-amylase expressed by a naturally occurring microorganism, such as a bacterium, yeast or filamentous fungus found in nature. The terms "wild-type enzyme" and "parent enzyme" can be used interchangeably when the parent enzyme is not a variant enzyme.

Variant Enzyme: The terms "variant" or "polypeptide variant" or "polypeptide" or "alpha-amylase variant" when used in relation to a variant of the present invention, as used herein, refer to a polypeptide having alpha-amylase activity comprising an alteration, i.e., a substitution, insertion, and/or deletion, at one or more (e.g., several) positions relative to the 'parent' alpha-amylase. A substitution means replacement of the amino acid occupying a position with a different amino acid; a deletion means removal of the amino acid occupying a position; and an insertion means adding an amino acid adjacent to and immediately following the amino acid occupying a position The variants of the present invention have at least 20%, e.g., at least 40%, at least 50%, at least 60%, at least 70%, at least 80%, at least 90%, at least 95%, or at least 100% of the alpha-amylase activity of the polypeptide of SEQ ID NOs: 1-13.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "wash performance" is defined herein as displaying an alteration of the wash performance of an amylase of the present invention relative to the wash performance of the parent amylase of SEQ ID NO: 1 or the amylase of SEQ ID NO: 2. Improved wash performance may be measured by comparing of the so-called Intensity value.

The term "wash cycle" is defined herein with respect to dishwashing as a washing operation wherein dishware are exposed to the wash liquor for a period of time by circulating the wash liquor and spraying the wash liquor onto the dishware in order to clean the dishware and finally the superfluous wash liquor is removed. A wash cycle may be repeated one, two, three, four, five or even six times at the same or at different temperatures. Hereafter the dishware is generally rinsed and dried. One of the wash cycles can be a soaking step, where the dishware is left soaking in the wash liquor for a period.

The term "wash liquor" is defined herein as the solution or mixture of water and detergent components.

The term "wash time" with respect to automatic dishwashing is defined herein as the time it takes for the entire washing process; i.e. the time for the wash cycle(s) and rinse cycle(s) together.

The term "detergent composition", includes unless otherwise indicated, granular or powder-form all-purpose or heavy-duty washing agents, especially cleaning detergents;

liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, soap bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types. The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents").

The term "automatic dishwashing detergent composition" refers to compositions comprising detergent components, which composition is intended for cleaning dishware such as plates, cups, glasses, bowls, cutlery such as spoons, knives, forks, serving utensils, ceramics, plastics, metals, china, glass and acrylics in a dishwashing machine. It is not intended that the present invention be limited to any particular detergent formulation or composition.

The term "detergent composition" is not intended to be limited to compositions that contain surfactants. It is intended that in addition to the enzymes herein described, the detergents compositions may comprise, e.g. one or more additional components selected from stabilizing agents, surfactants, hydrotopes, builders, co-builders, chelating agents, bleaching systems, bleach activators, bleach catalysts, polymers, metal care agents, glass care agents, crystal growth inhibitors and fabric-hueing agents.

The term "non-fabric detergent compositions" include non-textile surface detergent compositions, including but not limited to compositions for hard surface cleaning, such as dishwashing detergent compositions, oral detergent compositions, denture detergent compositions, and personal cleansing compositions.

The term "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of an enzyme refers to the quantity of enzyme described hereinbefore that achieves a desired level of enzymatic activity, e.g., in a defined detergent composition. In one embodiment, the effective amount of a protease is the same as the effective amount of an alpha-amylase. In another embodiment, the effective amount of a protease is different to the effective amount of an alpha-amylase, e.g., the effective amount of a protease may be more or may be less than the effective amount of an alpha-amylase.

The term "water hardness" or "degree of hardness" or "dH" or "° dH" as used herein refers to German degrees of hardness. One degree is defined as 10 milligrams of calcium oxide per litre of water.

The term "relevant washing conditions" is used herein to indicate the conditions, particularly washing temperature, time, washing mechanics, detergent concentration, type of detergent and water hardness, actually used in households in a detergent market segment.

The term "adjunct materials" means any liquid, solid or gaseous material selected for the particular type of detergent composition desired and the form of the product (e.g., liquid, granule, powder, bar, paste, spray, tablet, gel, or foam composition), which materials are also preferably compatible with the enzymes used in the composition. In some embodiments, granular compositions are in "compact" form, while in other embodiments, the liquid compositions are in a "concentrated" form.

The term "stain removing enzyme" as used herein, describes an enzyme that aids the removal of a stain or soil from a fabric or a hard surface. Stain removing enzymes act on specific substrates, e.g., protease on protein, amylase on starch, lipase and cutinase on lipids (fats and oils), pectinase on pectin and hemicellulases on hemicellulose. Stains are often depositions of complex mixtures of different components which either results in a local discolouration of the material by itself or which leaves a sticky surface on the object which may attract soils dissolved in the washing liquor thereby resulting in discolouration of the stained area. When an enzyme acts on its specific substrate present in a stain the enzyme degrades or partially degrades its substrate thereby aiding the removal of soils and stain components associated with the substrate during the washing process. For example, when a protease acts on a grass stain it degrades the protein components in the grass and allows the green/brown colour to be released during washing.

The term "reduced amount" means in this context that the amount of the component is smaller than the amount which would be used in a reference process under otherwise the same conditions. In a preferred embodiment the amount is reduced by, e.g., at least 5%, such as at least 10%, at least 15%, at least 20% or as otherwise herein described.

The term "low detergent concentration" system includes detergents where less than about 800 ppm of detergent components is present in the wash water. Asian, e.g., Japanese detergents are typically considered low detergent concentration systems.

The term "medium detergent concentration" system includes detergents wherein between about 800 ppm and about 2000 ppm of detergent components is present in the wash water. North American detergents are generally considered to be medium detergent concentration systems.

The term "high detergent concentration" system includes detergents wherein greater than about 2000 ppm of detergent components is present in the wash water. European detergents are generally considered to be high detergent concentration systems.

The term "liquid laundry detergent composition" as used herein refers to a detergent composition which is in a stabilized liquid form and used in a method for laundering a fabric. Thus, the detergent composition has been formulated to be in fluid form.

The term "powder laundry detergent composition" as used herein refers to a detergent composition which is in a solid form, such as a granulate, non-dusting granulate or powder, which is used in a method for laundering a fabric.

The term "liquid dishwash detergent composition" as used herein refers to a detergent composition which is in a stabilized liquid form and used in dishwash. Dishwash may be any kind of dishwash, such as manual dishwash and such as automated dishwash (ADW).

The term "powder dishwash detergent composition" as used herein refers to a detergent composition which is in a solid form, such as a granulate, powder or compact unit and used in dishwash. A powder dishwash detergent composition is typically used in automated dishwash, but the used is not limited to such ADW, and may also be intended for used in any other kind of dishwash, such as manual dishwash.

The terms "Delta intensity" or "Delta intensity value" are defined herein as the result of an intensity measurement of a test material, e.g. a Melamine tiles stained with starch DM-277 (Center For Testmaterials BV, P.O. Box 120, 3133 KT Vlaardingen, the Netherlands) or a hard surface. The delta intensity is the intensity value of the test material washed with amylase subtracting the intensity value of the test material washed without amylase.

The term "numbering is according to" as used herein, refers to the way each of the amino acid residues in a polypeptide of the present invention is numbered. I.e. the skilled person would know that when, e.g. position 202 is numbered according to SEQ ID NO: 1, he would know that by alignment of any other polypeptide with SEQ ID NO: 1, he will be able to determine the corresponding amino acid residue in the other polypeptide. Alignment of two or more amino acid sequences has been described elsewhere herein.

Conventions for Designation of Variants

For the purposes of the present invention, the polypeptide disclosed in SEQ ID NO: 1 is used to determine the corresponding amino acid residue in another alpha-amylase polypeptide. Thus, all mentioned positions and specific substitutions and/or deletions refer to the numbering used in SEQ ID NO: 1. However, the skilled person would recognize that the sequence of any other sequence herein disclosed may also be used to determine the corresponding amino acid residue in another alpha-amylase polypeptide. The amino acid sequence of another alpha-amylase is aligned with the polypeptide disclosed in SEQ ID NO: 1, and based on the alignment, the amino acid position number corresponding the any amino acid residue in the polypeptide disclosed in SEQ ID No: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other alpha-amylase has diverged from the polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the alpha-amylase variants of the present invention, the nomenclature described below is adapted for ease of reference. The accepted IUPAC single letter or three letter amino acid abbreviation is employed.

Substitutions: For an amino acid substitution, the following nomenclature is used: Original amino acid, position, substituted amino acid. Accordingly, the substitution of e.g. threonine at position 226 with alanine is designated as "Thr226Ala" or "T226A". Multiple mutations are separated by addition marks ("+"), e.g., "Gly205Arg+Ser411 Phe" or "G205R+S411 F", representing substitutions at positions 205 and 411 of glycine (G) with arginine (R) and serine (S) with phenylalanine (F), respectively.

Deletions: For an amino acid deletion, the following nomenclature is used: Original amino acid, position, *. Accordingly, the deletion of serine at position 181 is designated as "Ser181*" or "S181*". Multiple deletions are separated by addition marks ("+"), e.g., "Ser181*+Thr182*" or "S181*+T182*".

Insertions: For an amino acid insertion, the following nomenclature is used: Original amino acid, position, original amino acid, inserted amino acid. Accordingly the insertion of lysine after e.g. glycine at position 195 is designated "Gly195GlyLys" or "G195GK". An insertion of multiple amino acids is designated [Original amino acid, position, original amino acid, inserted amino acid #1, inserted amino acid #2; etc.].

For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195<br>G | 195 195a 195b<br>G - K - A |

Multiple alterations: Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations: Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

Alpha-Amylase Variants

The present invention relates an alpha-amylase variant of a parent alpha-amylase comprising a) a deletion and/or a substitution at two or three or four positions corresponding to positions R181, G182, H183 and G184 and b) a alteration in one or more (e.g., several) positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein each alteration is independently a substitution, insertion, or deletion, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13, and wherein said variant has alpha-amylase activity and wherein the said variant has improved wash performance compared to said parent alpha-amylase.

In one aspect, the present invention relates to alpha-amylase variant of a parent alpha-amylase polypeptide having alpha-amylase activity. Thus, in particular aspect, the present invention relates to variant of a parent alpha-amylase polypeptide having alpha-amylase activity, wherein said variant has an improved wash performance, and wherein said variant has alpha-amylase activity.

In one aspect, the present invention relates to an alpha-amylase variant of a parent alpha-amylase comprising a) a deletion and/or a substitution at two or three or four positions corresponding to positions R181, G182, H183 and G184 and b) an alteration in one or more (e.g., several) positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering, and wherein each alteration is independently a substitution, insertion, or deletion, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13, and wherein said variant has alpha-amylase activity and wherein the said variant has improved wash performance compared to said parent alpha-amylase of SEQ ID NO: 1 and/or SEQ ID NO: 2.

In one aspect, the number of alterations is 1-50, e.g., 1-45, 1-40, 1-35, 1-30, 1-25, 1-20, 1-15, 1- or 1-5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations.

In one aspect, the number of substitutions is 1-50, e.g., 1-45, 1-40, 1-35, 1-30, 1-25, 1-20, 1-15, 1-10 or 1-5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 substitutions.

In one aspect, the number of deletion is 1-50, e.g., 1-45, 1-40, 1-35, 1-30, 1-25, 1-20, 1-15, 1-10 or 1-5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 deletion.

In one aspect, the substituted amino acid residue is different from the naturally-occurring amino acid residue in that position. In one embodiment, the substitution is selected from the group consisting of A, C, D, E, F, G, H, I, K, L, M, N, P, Q, R, S, T, V, W and Y, with the proviso that the substituted amino acid residue is different from the naturally-occurring amino acid residue in that position.

In one embodiment the alpha-amylase variants of the invention are isolated variants.

The term "pairwise deletion" as used herein, refers to one deletion in two separate positions. Such positions may be adjacent to one another but are not limited to such adjacent pairs. A pairwise deletion may thus, also be deletion of one amino acid and another amino acid which may be up to three amino acids further downstream or upstream from the first deletion.

In another embodiment a) comprises a pairwise deletion of the amino acids corresponding to R181+G182 using SEQ ID NO: 1 for numbering.

In another embodiment a) comprises a pairwise deletion of the amino acids corresponding to R181+H183 using SEQ ID NO: 1 for numbering.

In another embodiment a) comprises a pairwise deletion of the amino acids corresponding to R181+G184 using SEQ ID NO: 1 for numbering.

In another embodiment a) comprises a pairwise deletion of the amino acids corresponding to G182+H183 using SEQ ID NO: 1 for numbering.

In another embodiment a) comprises a pairwise deletion of the amino acids corresponding to G182+G184 using SEQ ID NO: 1 for numbering.

In another embodiment a) comprises a pairwise deletion of the amino acids corresponding to H183+G184 using SEQ ID NO: 1 for numbering.

In another embodiment, a) further comprises a substitution at one or both of the non deleted positions of 181, 182, 183 and 184 using SEQ ID NO: 1 for numbering.

In a preferred embodiment a) comprises a pairwise deletion of the amino acids corresponding to H183+G184, using SEQ ID NO: 1 for numbering.

In another aspect, a variant comprises a) a pairwise deletion of the amino acids corresponding to positions H183*+G184* and b) an alteration at one or more positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, a variant a) a pairwise deletion of the amino acids corresponding to positions H183*+G184* and b) an alteration at two or more positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, a variant a) a pairwise deletion of the amino acids corresponding to positions H183*+G184* and b) an alteration at three or more positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, a variant a) a pairwise deletion of the amino acids corresponding to positions H183*+G184* and b) an alteration at four or more positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138,140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, a variant a) a pairwise deletion of the amino acids corresponding to positions H183*+G184* and b) an alteration at five or more positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, a variant a) a pairwise deletion of the amino acids corresponding to positions H183*+G184* and b) an alteration at six or more positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, a variant a) a pairwise deletion of the amino acids corresponding to positions H183*+G184* and b) an alteration at seven or more positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, a variant a) a pairwise deletion of the amino acids corresponding to positions H183*+G184* and b) an alteration at eight or more positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, a variant a) a pairwise deletion of the amino acids corresponding to positions H183*+G184* and b) an alteration at nine or more positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, a variant a) a pairwise deletion of the amino acids corresponding to positions H183*+G184* and b) an alteration at ten or more positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142,144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, a variant a) a pairwise deletion of the amino acids corresponding to positions H183*+G184* and b) an alteration at each positions corresponding to any of positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142,144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In one aspect, a variant useful herein comprises a) a pairwise deletion of the amino acids corresponding to positions H183*+G184* and b) one or more of the following alteration at position corresponding to positions 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein said variant has alpha-amylase activity and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In another aspect, the variant comprises or consists of a deletion or substitution at a position corresponding to position 1. In another aspect, the amino acid at a position corresponding to position 1 is deleted of the polypeptide of SEQ ID NO: 1. In another aspect, the variant comprises or consists of deletion H1* of the polypeptide of SEQ ID NO: 1. In another aspect, the amino acid at a position corresponding to position 1 is substituted with Ala, Arg, Asn, Asp, Cys, Gln, Glu, Gly, lie, Leu, Lys, Met, Phe, Pro, Ser, Thr, Trp, Tyr or Val. In another aspect, the variant comprises or consists of the substitution H1A of the polypeptide of SEQ ID NO: 1. In a preferred embodiment a) comprises a pairwise deletion of the amino acids corresponding to H183*+G184* and b) comprises or consists of deletion H1* or substitution H1A of the polypeptide of SEQ ID NO: 1.

In another aspect, the variant comprises or consists of a deletion or substitution at a position corresponding to position 2. In another aspect, the amino acid at a position corresponding to position 2 is deleted of the polypeptide of SEQ ID NO: 1. In another aspect, the variant comprises or consists of deletion H2* of the polypeptide of SEQ ID NO: 1. In a preferred embodiment a) comprises a pairwise deletion of the amino acids corresponding to H183*+G184* and b) comprises or consists of deletion H2* of the polypeptide of SEQ ID NO: 1.

In another aspect, the variant comprises or consists of a substitution at a position corresponding to position 3. In another aspect, the amino acid at a position corresponding to position 3 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N3D or N3A of the polypeptide of SEQ ID NO: 1. In a preferred embodiment a) comprises a pairwise deletion of the amino acids corresponding to H183*+G184* and b) comprises or consists of the substitution N3D or N3A of the polypeptide of SEQ ID NO: 1.

In another aspect, the variant comprises or consists of a substitution at a position corresponding to position 4. In another aspect, the amino acid at a position corresponding to position 4 is substituted with Ala, Arg, Asn, Asp, Cys, Gln, Glu, His, lie, Leu, Lys, Met, Phe, Pro, Ser, Thr, Trp, Tyr or Val. In another aspect, the variant comprises or consists of the substitution G4N or G4A of the polypeptide of SEQ ID NO: 1. In a preferred embodiment a) comprises a pairwise deletion of the amino acids corresponding to H183*+G184* and b) comprises or consists of the substitution G4N or G4A of the polypeptide of SEQ ID NO: 1.

In another aspect, the variant comprises or consists of a substitution at a position corresponding to position 5. In another aspect, the amino acid at a position corresponding to position 5 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T5L of the polypeptide of SEQ ID NO: 1. In a preferred embodiment a) comprises a pairwise deletion of the amino acids corresponding to H183*+G184* and b) comprises or consists of the substitution T5L of the polypeptide of SEQ ID NO: 1.

In another aspect, the variant comprises or consists of a substitution at a position corresponding to position 9. In another aspect, the amino acid at a position corresponding to position 9 is substituted with Ala, Arg, Asn, Asp, Cys, Gln, Glu, Gly, His, lie, Leu, Lys, Phe, Pro, Ser, Thr, Trp, Tyr or Val. In another aspect, the variant comprises or consists of the substitution M9L or M91 of the polypeptide of SEQ ID NO: 1. In a preferred embodiment a) comprises a pairwise deletion of the amino acids corresponding to H183*+G184* and b) comprises or consists of the substitution M9L or M91 of the polypeptide of SEQ ID NO: 1.

In another aspect, the variant comprises or consists of a substitution at a position corresponding to position 16. In another aspect, the amino acid at a position corresponding to position 16 is substituted with Ala, Arg, Asn, Asp, Cys, Gln, Glu, Gly, His, lie, Leu, Lys, Met, Phe, Pro, Ser, Thr, Trp or Val. In another aspect, the variant comprises or consists of the substitution Y16N of the polypeptide of SEQ ID NO: 1. In a preferred embodiment a) comprises a pairwise deletion of the amino acids corresponding to H183*+G184* and b) comprises or consists of the substitution Y16N of the polypeptide of SEQ ID NO: 1.

In another aspect, the variant comprises or consists of a substitution at a position corresponding to position 17. In another aspect, the amino acid at a position corresponding to position 17 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution L17M or L17V of the polypeptide of SEQ ID NO: 1. In a preferred embodiment a) comprises a pairwise deletion of the amino acids corresponding to H183*+G184* and b) comprises or consists of the substitution L17M or L17V of the polypeptide of SEQ ID NO: 1.

In another aspect, the variant comprises or consists of a substitution at a position corresponding to position 22. In another aspect, the amino acid at a position corresponding to position 22 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution N22Q of the polypeptide of SEQ ID NO: 1. In a preferred embodiment a) comprises a pairwise deletion of the amino acids corresponding to H183*+G184* and b) comprises or consists of the substitution N22Q of the polypeptide of SEQ ID NO: 1.

In another aspect, the variant comprises or consists of a substitution at a position corresponding to position 23. In another aspect, the amino acid at a position corresponding to position 23 is substituted with Ala, Arg, Asn, Asp, Cys, Gln, Glu, Gly, lie, Leu, Lys, Met, Phe, Pro, Ser, Thr, Trp, Tyr or Val. In another aspect, the variant comprises or consists of the substitution H23Q of the polypeptide of SEQ ID NO: 1. In a preferred embodiment a) comprises a pairwise deletion of the amino acids corresponding to H183*+G184* and b) comprises or consists of the substitution H23Q of the polypeptide of SEQ ID NO: 1.

In another aspect, the variant comprises or consists of a substitution at a position corresponding to position 25. In another aspect, the amino acid at a position corresponding to position 25 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N25R or N25K of the polypeptide of SEQ ID NO: 1. In a preferred embodiment a) comprises a pairwise deletion of the amino acids corresponding to H183*+G184* and b) comprises or consists of the substitution N25R or N25K of the polypeptide of SEQ ID NO: 1.

In another aspect, the variant comprises or consists of a substitution at a position corresponding to position 28. In another aspect, the amino acid at a position corresponding to position 28 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N28R or N28Q of the polypeptide of SEQ ID NO: 1. In a preferred embodiment a) comprises a pairwise deletion of the amino acids corresponding to H183*+G184* and b) comprises or consists of the substitution N28R or N28Q of the polypeptide of SEQ ID NO: 1.

In another aspect, the variant comprises or consists of a substitution at a position corresponding to position 29. In another aspect, the amino acid at a position corresponding to position 29 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S29N or S29Tof the polypeptide of SEQ ID NO: 1. In a preferred embodiment a) comprises a pairwise deletion of the amino acids corresponding to H183*+G184* and b) comprises or consists of the substitution S29N or S29Tof the polypeptide of SEQ ID NO: 1.

In another aspect, the variant comprises or consists of a substitution at a position corresponding to position 30. In another aspect, the amino acid at a position corresponding to position 30 is substituted with Ala, Arg, Asn, Cys, Gln, Glu, Gly, His, lie, Leu, Lys, Met, Phe, Pro, Ser, Thr, Trp, Tyr or Val. In another aspect, the variant comprises or consists of the substitution D30N of the polypeptide of SEQ ID NO: 1. In a preferred embodiment a) comprises a pairwise deletion of the amino acids corresponding to H183*+G184* and b) comprises or consists of the substitution D30N of the polypeptide of SEQ ID NO: 1.

In another aspect, the variant comprises or consists of a substitution at a position corresponding to position 31. In another aspect, the amino acid at a position corresponding to position 31 is substituted with Arg, Asn, Asp, Cys, Gln, Glu, Gly, His, lie, Leu, Lys, Met, Phe, Pro, Thr, Trp, Tyr or Val. In another aspect, the variant comprises or consists of the substitution A31S of the polypeptide of SEQ ID NO: 1. In a preferred embodiment a) comprises a pairwise deletion of the amino acids corresponding to H183*+G184* and b) comprises or consists of the substitution A31S of the polypeptide of SEQ ID NO: 1.

In another aspect, the variant comprises or consists of a substitution at a position corresponding to position 32. In another aspect, the amino acid at a position corresponding to position 32 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S32P or S32A or S32Q of the polypeptide of SEQ ID NO: 1. In a preferred embodiment a) comprises a pairwise deletion of the amino acids corresponding to H183*+G184* and b) comprises or consists of the substitution S32P or S32A or S32Q of the polypeptide of SEQ ID NO: 1.

In another aspect, the variant comprises or consists of a substitution at a position corresponding to position 33. In another aspect, the amino acid at a position corresponding to position 33 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N33Y of the polypeptide of SEQ ID NO: 1. In a preferred embodiment a) comprises a pairwise deletion of the amino acids corresponding to H183*+G184* and b) comprises or consists of the substitution N33Y of the polypeptide of SEQ ID NO: 1.

In another aspect, the variant comprises or consists of a substitution at a position corresponding to position 35. In another aspect, the amino acid at a position corresponding to position 35 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution K35A or K35S of the polypeptide of SEQ ID NO: 1. In a preferred embodiment a) comprises a pairwise deletion of the amino acids corresponding to H183*+G184* and b) comprises or consists of the substitution K35A or K35S of the polypeptide of SEQ ID NO: 1.

In another aspect, the variant comprises or consists of a substitution at a position corresponding to position 36. In another aspect, the amino acid at a position corresponding to position 36 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S36E or S36D of the polypeptide of SEQ ID NO: 1. In a preferred embodiment a) comprises a pairwise deletion of the amino acids corresponding to H183*+G184* and b) comprises or consists of the substitution S36E or S36D of the polypeptide of SEQ ID NO: 1.

In another aspect, the variant comprises or consists of a substitution at a position corresponding to position 37. In another aspect, the amino acid at a position corresponding to position 37 is substituted with Ala, Arg, Asn, Asp, Cys, Gln, Glu, Gly, His, lie, Leu, Met, Phe, Pro, Ser, Thr, Trp, Tyr or Val. In another aspect, the variant comprises or consists of the substitution K37V or K37H of the polypeptide of SEQ ID NO: 1. In a preferred embodiment a) comprises a pairwise deletion of the amino acids corresponding to H183*+G184* and b) comprises or consists of the substitution K37V or K37H of the polypeptide of SEQ ID NO: 1.

In another aspect, the variant comprises or consists of a substitution at a position corresponding to position 40. In another aspect, the amino acid at a position corresponding to position 40 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T40S or T40N of the polypeptide of SEQ ID NO: 1. In a preferred embodiment a) comprises a pairwise deletion of the amino acids corresponding to H183*+G184* and b) comprises or consists of the substitution T40S or T40N of the polypeptide of SEQ ID NO: 1.

In another aspect, the variant comprises or consists of a substitution at a position corresponding to position 42. In another aspect, the amino acid at a position corresponding to position 42 is substituted with Ala, Arg, Asn, Asp, Cys, Gln, Glu, Gly, His, lie, Leu, Lys, Met, Phe, Pro, Ser, Thr, Trp, or Tyr. In another aspect, the variant comprises or consists of the substitution V421 of the polypeptide of SEQ ID NO: 1. In a preferred embodiment a) comprises a pairwise deletion of the amino acids corresponding to H183*+G184* and b) comprises or consists of the substitution V421 of the polypeptide of SEQ ID NO: 1.

In another aspect, the variant comprises or consists of a substitution at a position corresponding to position 44. In another aspect, the amino acid at a position corresponding to position 44 is substituted with Ala, Arg, Asn, Asp, Cys, Gln, Glu, Gly, His, Leu, Lys, Met, Phe, Pro, Ser, Thr, Trp, Tyr or Val. In another aspect, the variant comprises or consists of the substitution 144T of the polypeptide of SEQ ID NO: 1. In a preferred embodiment a) comprises a pairwise deletion of the amino acids corresponding to H183*+G184* and b) comprises or consists of the substitution 144T of the polypeptide of SEQ ID NO: 1.

In another aspect, the variant comprises or consists of a substitution at a position corresponding to position 48. In another aspect, the amino acid at a position corresponding to position 48 is substituted with Ala, Arg, Asn, Asp, Cys, Gln, Glu, Gly, His, lie, Leu, Lys, Met, Phe, Pro, Ser, Thr, Trp or Val. In another aspect, the variant comprises or consists of the substitution W48Y of the polypeptide of SEQ ID NO: 1. In a preferred embodiment a) comprises a pairwise deletion of the amino acids corresponding to H183*+G184* and b) comprises or consists of the substitution W48Y of the polypeptide of SEQ ID NO: 1.

In another aspect, the variant comprises or consists of a substitution at a position corresponding to position 51. In another aspect, the amino acid at a position corresponding to position 51 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A51T of the polypeptide of SEQ ID NO: 1. In a preferred embodiment a) comprises a pairwise deletion of the amino acids corresponding to H183*+G184* and b) comprises or consists of the substitution A51T of the polypeptide of SEQ ID NO: 1.

In another aspect, the variant comprises or consists of a substitution at a position corresponding to position 54. In another aspect, the amino acid at a position corresponding to position 54 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution N54A or N54S of the polypeptide of SEQ ID NO: 1. In a preferred embodiment a) comprises a pairwise deletion of the amino acids corresponding to H183*+G184* and b) comprises or consists of the substitution N54A or N54S of the polypeptide of SEQ ID NO: 1.

In another aspect, the variant comprises or consists of a substitution at a position corresponding to position 56. In another aspect, the amino acid at a position corresponding to position 56 is substituted with Ala, Arg, Asn, Asp, Cys, Gln, Glu, Gly, His, lie, Leu, Lys, Met, Phe, Pro, Ser, Thr, Trp, or Tyr. In another aspect, the variant comprises or consists of the substitution V56T of the polypeptide of SEQ ID NO: 1. In a preferred embodiment a) comprises a pairwise deletion of the amino acids corresponding to H183*+G184* and b) comprises or consists of the substitution V56T of the polypeptide of SEQ ID NO: 1.

In another aspect, the variant comprises or consists of a substitution at a position corresponding to position 60. In another aspect, the amino acid at a position corresponding to position 60 is substituted with Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A60P of the polypeptide of SEQ ID NO: 1. In a preferred embodiment a) comprises a pairwise deletion of the amino acids corresponding to H183*+G184* and b) comprises or consists of the substitution A60P of the polypeptide of SEQ ID NO: 1.

In another aspect, the variant comprises or consists of a substitution at a position corresponding to position 62. In another aspect, the amino acid at a position corresponding to position 62 is substituted with Ala, Arg, Asn, Cys, Gln, Glu, Gly, His, lie, Leu, Lys, Met, Phe, Pro, Ser, Thr, Trp, Tyr or Val. In another aspect, the variant comprises or consists of the substitution D62N of the polypeptide of SEQ ID NO: 1. In a preferred embodiment a) comprises a pairwise deletion of the amino acids corresponding to H183*+G184* and b) comprises or consists of the substitution D62N of the polypeptide of SEQ ID NO: 1.

In another aspect, the variant comprises or consists of a substitution at a position corresponding to position 70. In another aspect, the amino acid at a position corresponding to position 70 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N70H of the polypeptide of SEQ ID NO: 1. In a preferred embodiment a) comprises a pairwise deletion of the amino acids corresponding to H183*+G184* and b) comprises or consists of the substitution N70H of the polypeptide of SEQ ID NO: 1.

In another aspect, the variant comprises or consists of a substitution at a position corresponding to position 75. In another aspect, the amino acid at a position corresponding to position 75 is substituted with Ala, Arg, Asn, Asp, Cys, Gln, Glu, Gly, His, lie, Leu, Lys, Met, Phe, Pro, Ser, Thr, Trp, or Tyr. In another aspect, the variant comprises or consists of the substitution V751 of the polypeptide of SEQ ID NO: 1. In a preferred embodiment a) comprises a pairwise deletion of the amino acids corresponding to H183*+G184* and b) comprises or consists of the substitution V751 of the polypeptide of SEQ ID NO: 1.

In another aspect, the variant comprises or consists of a substitution at a position corresponding to position 82. In another aspect, the amino acid at a position corresponding to position 82 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R82K of the polypeptide of SEQ ID NO: 1. In a preferred embodiment a) comprises a pairwise deletion of the amino acids corresponding to H183*+G184* and b) comprises or consists of the substitution R82K of the polypeptide of SEQ ID NO: 1 In another aspect, the variant comprises or consists of a substitution at a position corresponding to position 83. In another aspect, the amino acid at a position corresponding to position 83 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S83N or S83G of the polypeptide of SEQ ID NO: 1. In a preferred embodiment a) comprises a pairwise deletion of the amino acids corresponding to H183*+G184* and b) comprises or consists of the substitution S83N or S83G of the polypeptide of SEQ ID NO: 1.

In another aspect, the variant comprises or consists of a substitution at a position corresponding to position 84. In another aspect, the amino acid at a position corresponding to position 84 is substituted with Ala, Arg, Asn, Asp, Cys, Glu, Gly, His, lie, Leu, Lys, Met, Phe, Pro, Ser, Thr, Trp, Tyr or Val. In another aspect, the variant comprises or consists of the substitution Q84D or Q84E of the polypeptide of SEQ ID NO: 1. In a preferred embodiment a) comprises a pairwise deletion of the amino acids corresponding to H183*+G184* and b) comprises or consists of the substitution Q84D or Q84E of the polypeptide of SEQ ID NO: 1.

In another aspect, the variant comprises or consists of a substitution at a position corresponding to position 86. In another aspect, the amino acid at a position corresponding to position 86 is substituted with Ala, Arg, Asn, Asp, Cys, Glu, Gly, His, lie, Leu, Lys, Met, Phe, Pro, Ser, Thr, Trp, Tyr or Val. In another aspect, the variant comprises or consists of the substitution Q86E or Q86K of the polypeptide of SEQ ID NO: 1. In a preferred embodiment a) comprises a pairwise deletion of the amino acids corresponding to H183*+G184* and b) comprises or consists of the substitution Q86E or Q86K of the polypeptide of SEQ ID NO: 1.

In another aspect, the variant comprises or consists of a substitution at a position corresponding to position 87. In another aspect, the amino acid at a position corresponding to position 87 is substituted with Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A87S or A87R of the polypeptide of SEQ ID NO: 1. In a preferred embodiment a) comprises a pairwise deletion of the amino acids corresponding to H183*+G184* and b) comprises or consists of the substitution A87S or A87R of the polypeptide of SEQ ID NO: 1.

In another aspect, the variant comprises or consists of a substitution at a position corresponding to position 89. In another aspect, the amino acid at a position corresponding to position 89 is substituted with Ala, Arg, Asn, Asp, Cys, Gln, Glu, Gly, His, lie, Leu, Lys, Met, Phe, Pro, Ser, Thr, Trp, or Tyr. In another aspect, the variant comprises or consists of the substitution V891 of the polypeptide of SEQ ID NO: 1. In a preferred embodiment a) comprises a pairwise deletion of the amino acids corresponding to H183*+G184* and b) comprises or consists of the substitution V891 of the polypeptide of SEQ ID NO: 1.

In another aspect, the variant comprises or consists of a substitution at a position corresponding to position 90. In another aspect, the amino acid at a position corresponding to position 90 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T90N or T90K of the polypeptide of SEQ ID NO: 1. In a preferred embodiment a) comprises a pairwise deletion of the amino acids corresponding to H183*+G184* and b) comprises or consists of the substitution T90N or T90K of the polypeptide of SEQ ID NO: 1.

In another aspect, the variant comprises or consists of a substitution at a position corresponding to position 91. In another aspect, the amino acid at a position corresponding to position 91 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S91A or S91T of the polypeptide of SEQ ID NO: 1. In a preferred embodiment a) comprises a pairwise deletion of the amino acids corresponding to H183*+G184* and b) comprises or consists of the substitution S91A or S91T of the polypeptide of SEQ ID NO: 1.

In another aspect, the variant comprises or consists of a substitution at a position corresponding to position 93. In another aspect, the amino acid at a position corresponding to position 93 is substituted with Ala, Arg, Asn, Asp, Cys, Gln, Glu, Gly, His, lie, Leu, Met, Phe, Pro, Ser, Thr, Trp, Tyr or Val. In another aspect, the variant comprises or consists of the substitution K93H of the polypeptide of SEQ ID NO: 1. In a preferred embodiment a) comprises a pairwise deletion of the amino acids corresponding to H183*+G184* and b) comprises or consists of the substitution K93H of the polypeptide of SEQ ID NO: 1.

In another aspect, the variant comprises or consists of a substitution at a position corresponding to position 94. In another aspect, the amino acid at a position corresponding to position 94 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N94S or N94A of the polypeptide of SEQ ID NO: 1. In a preferred embodiment a) comprises a pairwise deletion of the amino acids corresponding to H183*+G184* and b) comprises or consists of the substitution N94S or N94A of the polypeptide of SEQ ID NO: 1.

In another aspect, the variant comprises or consists of a substitution at a position corresponding to position 95. In another aspect, the amino acid at a position corresponding to position 95 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution N95R of the polypeptide of SEQ ID NO: 1. In a preferred embodiment a) comprises a pairwise deletion of the amino acids corresponding to H183*+G184* and b) comprises or consists of the substitution N95R of the polypeptide of SEQ ID NO: 1.

In another aspect, the variant comprises or consists of a substitution at a position corresponding to position 98. In another aspect, the amino acid at a position corresponding to position 98 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution Q98N of the polypeptide of SEQ ID NO: 1. In a preferred embodiment a) comprises a pairwise deletion of the amino acids corresponding to H183*+G184* and b) comprises or consists of the substitution Q98N of the polypeptide of SEQ ID NO: 1.

In another aspect, the variant comprises or consists of a substitution at a position corresponding to position 105. In another aspect, the amino acid at a position corresponding to position 105 is substituted with Ala, Arg, Asn, Asp, Cys, Gln, Glu, Gly, His, lie, Leu, Lys, Phe, Pro, Ser, Thr, Trp, Tyr or Val. In another aspect, the variant comprises or consists of the substitution M1 051 of the polypeptide of SEQ ID NO: 1. In a preferred embodiment a) comprises a pairwise deletion of the amino acids corresponding to H183*+G184* and b) comprises or consists of the substitution M105I of the polypeptide of SEQ ID NO: 1.

In another aspect, the variant comprises or consists of a substitution at a position corresponding to position 109. In another aspect, the amino acid at a position corresponding to position 109 is substituted with Ala, Arg, Asn, Asp, Cys, Gln, Glu, His, lie, Leu, Lys, Met, Phe, Pro, Ser, Thr, Trp, Tyr or Val. In another aspect, the variant comprises or consists of the substitution G109A of the polypeptide of SEQ ID NO: 1. In a preferred embodiment a) comprises a pairwise deletion of the amino acids corresponding to H183*+G184* and b) comprises or consists of the substitution G109A of the polypeptide of SEQ ID NO: 1.

In another aspect, the variant comprises or consists of a substitution at a position corresponding to position 113. In another aspect, the amino acid at a position corresponding to position 113 is substituted with Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A113Y or A113Q of the polypeptide of SEQ ID NO: 1. In a preferred embodiment a) comprises a pairwise deletion of the amino acids corresponding to H183*+G184* and b) comprises or consists of the substitution A113Y or A113Q of the polypeptide of SEQ ID NO: 1.

In another aspect, the variant comprises or consists of a substitution at a position corresponding to position 116. In another aspect, the amino acid at a position corresponding to position 116 is substituted with Ala, Arg, Asn, Asp, Cys, Gln, Glu, Gly, His, lie, Leu, Lys, Phe, Pro, Ser, Thr, Trp, Tyr or Val. In another aspect, the variant comprises or consists of the substitution M116D or M116N of the polypeptide of SEQ ID NO: 1. In a preferred embodiment a) comprises a pairwise deletion of the amino acids corresponding to H183*+G184* and b) comprises or consists of the substitution M116D or M116N of the polypeptide of SEQ ID NO: 1.

In another aspect, the variant comprises or consists of a substitution at a position corresponding to position 118. In another aspect, the amino acid at a position corresponding to position 118 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R118N or R118T or R118Q of the polypeptide of SEQ ID NO: 1. In a preferred embodiment a)

comprises a pairwise deletion of the amino acids corresponding to H183*+G184* and b) comprises or consists of the substitution R118N or R118T or R118Q of the polypeptide of SEQ ID NO: 1.

In another aspect, the variant comprises or consists of a substitution at a position corresponding to position 125. In another aspect, the amino acid at a position corresponding to position 125 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N125S or N125Q of the polypeptide of SEQ ID NO: 1. In a preferred embodiment a) comprises a pairwise deletion of the amino acids corresponding to H183*+G184* and b) comprises or consists of the substitution N125S or N125Q of the polypeptide of SEQ ID NO: 1.

In another aspect, the variant comprises or consists of a substitution at a position corresponding to position 128. In another aspect, the amino acid at a position corresponding to position 128 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N128Y of the polypeptide of SEQ ID NO: 1. In a preferred embodiment a) comprises a pairwise deletion of the amino acids corresponding to H183*+G184* and b) comprises or consists of the substitution N128Y of the polypeptide of SEQ ID NO: 1.

In another aspect, the variant comprises or consists of a substitution at a position corresponding to position 130. In another aspect, the amino acid at a position corresponding to position 130 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E130V of the polypeptide of SEQ ID NO: 1. In a preferred embodiment a) comprises a pairwise deletion of the amino acids corresponding to H183*+G184* and b) comprises or consists of the substitution E130V of the polypeptide of SEQ ID NO: 1.

In another aspect, the variant comprises or consists of a substitution at a position corresponding to position 131. In another aspect, the amino acid at a position corresponding to position 131 is substituted with Ala, Arg, Asn, Asp, Cys, Gln, Glu, Gly, His, lie, Leu, Lys, Met, Phe, Pro, Ser, Thr, Trp or Tyr. In another aspect, the variant comprises or consists of the substitution V131I of the polypeptide of SEQ ID NO: 1. In a preferred embodiment a) comprises a pairwise deletion of the amino acids corresponding to H183*+G184* and b) comprises or consists of the substitution V131I of the polypeptide of SEQ ID NO: 1.

In another aspect, the variant comprises or consists of a substitution at a position corresponding to position 132. In another aspect, the amino acid at a position corresponding to position 132 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T132S of the polypeptide of SEQ ID NO: 1. In a preferred embodiment a) comprises a pairwise deletion of the amino acids corresponding to H183*+G184* and b) comprises or consists of the substitution T132S of the polypeptide of SEQ ID NO: 1.

In another aspect, the variant comprises or consists of a substitution at a position corresponding to position 134. In another aspect, the amino acid at a position corresponding to position 134 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E134T or E134D of the polypeptide of SEQ ID NO: 1. In a preferred embodiment a) comprises a pairwise deletion of the amino acids corresponding to H183*+G184* and b) comprises or consists of the substitution E134T or E134D of the polypeptide of SEQ ID NO: 1.

In another aspect, the variant comprises or consists of a substitution at a position corresponding to position 135. In another aspect, the amino acid at a position corresponding to position 135 is substituted with Ala, Arg, Asn, Asp, Cys, Gln, Glu, Gly, His, lie, Leu, Lys, Met, Phe, Pro, Ser, Thr, Trp or Val. In another aspect, the variant comprises or consists of the substitution Y135H of the polypeptide of SEQ ID NO: 1. In a preferred embodiment a) comprises a pairwise deletion of the amino acids corresponding to H183*+G184* and b) comprises or consists of the substitution Y135H of the polypeptide of SEQ ID NO: 1.

In another aspect, the variant comprises or consists of a substitution at a position corresponding to position 136. In another aspect, the amino acid at a position corresponding to position 136 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T136L or T136N of the polypeptide of SEQ ID NO: 1. In a preferred embodiment a) comprises a pairwise deletion of the amino acids corresponding to H183*+G184* and b) comprises or consists of the substitution T136L or T136N of the polypeptide of SEQ ID NO: 1.

In another aspect, the variant comprises or consists of a substitution at a position corresponding to position 138. In another aspect, the amino acid at a position corresponding to position 138 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E138K or E138Q of the polypeptide of SEQ ID NO: 1. In a preferred embodiment a) comprises a pairwise deletion of the amino acids corresponding to H183*+G184* and b) comprises or consists of the substitution E138K or E138Q of the polypeptide of SEQ ID NO: 1.

In another aspect, the variant comprises or consists of a substitution at a position corresponding to position 140. In another aspect, the amino acid at a position corresponding to position 140 is substituted with Ala, Arg, Asn, Asp, Cys, Gln, Glu, Gly, His, lie, Leu, Lys, Met, Phe, Pro, Ser, Thr, Tyr or Val. In another aspect, the variant comprises or consists of the substitution W140Y of the polypeptide of SEQ ID NO: 1. In a preferred embodiment a) comprises a pairwise deletion of the amino acids corresponding to H183*+G184* and b) comprises or consists of the substitution W140Y of the polypeptide of SEQ ID NO: 1.

In another aspect, the variant comprises or consists of a substitution at a position corresponding to position 142. In another aspect, the amino acid at a position corresponding to position 412 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R142G or R142K or R142H of the polypeptide of SEQ ID NO: 1. In a preferred embodiment a) comprises a pairwise deletion of the amino acids corresponding to H183*+G184* and b) comprises or consists of the substitution R142G or R142K or R142H of the polypeptide of SEQ ID NO: 1.

In another aspect, the variant comprises or consists of a substitution at a position corresponding to position 144. In another aspect, the amino acid at a position corresponding to position 144 is substituted with Ala, Arg, Asn, Cys, Gln, Glu, Gly, His, lie, Leu, Lys, Met, Phe, Pro, Ser, Thr, Trp, Tyr or Val. In another aspect, the variant comprises or consists of the substitution D144N or D144H of the polypeptide of SEQ ID NO: 1. In a preferred embodiment a) comprises a pairwise deletion of the amino acids corresponding to H183*+G184* and b) comprises or consists of the substitution D144N or D144H of the polypeptide of SEQ ID NO: 1.

In another aspect, the variant comprises or consists of a substitution at a position corresponding to position 150. In another aspect, the amino acid at a position corresponding to position 150 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution N150T or N150S of the polypeptide of SEQ ID NO: 1. In a preferred embodiment a) comprises a pairwise deletion of the amino acids corresponding to H183*+G184* and b) comprises or consists of the substitution N150T or N150S of the polypeptide of SEQ ID NO: 1.

In another aspect, the variant comprises or consists of a substitution at a position corresponding to position 151. In another aspect, the amino acid at a position corresponding to position 151 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution T151Q of the polypeptide of SEQ ID NO: 1. In a preferred embodiment a) comprises a pairwise deletion of the amino acids corresponding to H183*+G184* and b) comprises or consists of the substitution T151Q of the polypeptide of SEQ ID NO: 1.

In another aspect, the variant comprises or consists of a substitution at a position corresponding to position 152. In another aspect, the amino acid at a position corresponding to position 152 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution H152Y of the polypeptide of SEQ ID NO: 1. In a preferred embodiment a) comprises a pairwise deletion of the amino acids corresponding to H183*+G184* and b) comprises or consists of the substitution H152Y of the polypeptide of SEQ ID NO: 1.

In another aspect, the variant comprises or consists of a substitution at a position corresponding to position 154. In another aspect, the amino acid at a position corresponding to position 154 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution S154N or S154D of the polypeptide of SEQ ID NO: 1. In a preferred embodiment a) comprises a pairwise deletion of the amino acids corresponding to H183*+G184* and b) comprises or consists of the substitution S154N or S154D of the polypeptide of SEQ ID NO: 1.

In another aspect, the variant comprises or consists of a substitution at a position corresponding to position 155. In another aspect, the amino acid at a position corresponding to position 155 is substituted with Ala, Arg, Asn, Asp, Cys, Gln, Glu, Gly, His, lie, Leu, Lys, Met, Pro, Ser, Thr, Trp, Tyr or Val. In another aspect, the variant comprises or consists of the substitution F155W of the polypeptide of SEQ ID NO: 1. In a preferred embodiment a) comprises a pairwise deletion of the amino acids corresponding to H183*+G184* and b) comprises or consists of the substitution F155W of the polypeptide of SEQ ID NO: 1.

In another aspect, the variant comprises or consists of a substitution at a position corresponding to position 158. In another aspect, the amino acid at a position corresponding to position 158 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R158Q or R158Y of the polypeptide of SEQ ID NO: 1. In a preferred embodiment a) comprises a pairwise deletion of the amino acids corresponding to H183*+G184* and b) comprises or consists of the substitution R158Q or R1 58Y of the polypeptide of SEQ ID NO: 1.

In another aspect, the variant comprises or consists of a substitution at a position corresponding to position 160. In another aspect, the amino acid at a position corresponding to position 160 is substituted with Ala, Arg, Asn, Asp, Cys, Gln, Glu, Gly, His, lie, Leu, Lys, Met, Phe, Pro, Ser, Thr, Trp, or Val. In another aspect, the variant comprises or consists of the substitution Y160F of the polypeptide of SEQ ID NO: 1. In a preferred embodiment a) comprises a pairwise deletion of the amino acids corresponding to H183*+G184* and b) comprises or consists of the substitution Y160F of the polypeptide of SEQ ID NO: 1.

In another aspect, the variant comprises or consists of a substitution at a position corresponding to position 165. In another aspect, the amino acid at a position corresponding to position 165 is substituted with Ala, Arg, Asn, Asp, Cys, Gln, Glu, Gly, His, lie, Leu, Lys, Met, Phe, Pro, Ser, Thr, Trp, or Tyr. In another aspect, the variant comprises or consists of the substitution V165T of the polypeptide of SEQ ID NO: 1. In a preferred embodiment a) comprises a pairwise deletion of the amino acids corresponding to H183*+G184* and b) comprises or consists of the substitution V165T of the polypeptide of SEQ ID NO: 1.

In another aspect, the variant comprises or consists of a substitution at a position corresponding to position 167. In another aspect, the amino acid at a position corresponding to position 167 is substituted with Ala, Arg, Asn, Asp, Cys, Gln, Glu, Gly, His, lie, Leu, Lys, Met, Phe, Pro, Ser, Thr, Tyr or Val. In another aspect, the variant comprises or consists of the substitution W167F of the polypeptide of SEQ ID NO: 1. In a preferred embodiment a) comprises a pairwise deletion of the amino acids corresponding to H183*+G184* and b) comprises or consists of the substitution W167F of the polypeptide of SEQ ID NO: 1.

In another aspect, the variant comprises or consists of a substitution at a position corresponding to position 169. In another aspect, the amino acid at a position corresponding to position 169 is substituted with Ala, Arg, Asn, Asp, Cys, Glu, Gly, His, lie, Leu, Lys, Met, Phe, Pro, Ser, Thr, Trp, Tyr or Val. In another aspect, the variant comprises or consists of the substitution Q169E of the polypeptide of SEQ ID NO: 1. In a preferred embodiment a) comprises a pairwise deletion of the amino acids corresponding to H183*+G184* and b) comprises or consists of the substitution Q169E of the polypeptide of SEQ ID NO: 1.

In another aspect, the variant comprises or consists of a substitution at a position corresponding to position 172. In another aspect, the amino acid at a position corresponding to position 172 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R172S of the polypeptide of SEQ ID NO: 1. In a preferred embodiment a) comprises a pairwise deletion of the amino acids corresponding to H183*+G184* and b) comprises or consists of the substitution R172S of the polypeptide of SEQ ID NO: 1.

In another aspect, the variant comprises or consists of a deletion or substitution at a position corresponding to position 174. In another aspect, the amino acid at a position corresponding to position 174 is deleted of the polypeptide of SEQ ID NO: 1. In another aspect, the variant comprises or consists of deletion N174* of the polypeptide of SEQ ID NO: 1. In another aspect, the amino acid at a position corresponding to position 174 is substituted with Ala, Arg, Asp, Cys, Gln, Glu, Gly, lie, Leu, Lys, His, Met, Phe, Pro, Ser, Thr, Trp, Tyr or Val. In another aspect, the variant comprises or consists of the substitution N174S of the polypeptide of SEQ ID NO: 1. In a preferred embodiment a) comprises a pairwise deletion of the amino acids corresponding to H183*+G184* and b) comprises or consists of deletion N174* or substitution N174S of the polypeptide of SEQ ID NO: 1.

In another aspect, the variant comprises or consists of a substitution at a position corresponding to position 175. In another aspect, the amino acid at a position corresponding to position 175 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution N175S of the polypeptide of SEQ ID NO: 1. In a preferred embodiment a) comprises a pairwise deletion of the amino acids corresponding to H183*+G184* and b) comprises or consists of the substitution N175S of the polypeptide of SEQ ID NO: 1.

In another aspect, the variant comprises or consists of a substitution at a position corresponding to position 178. In another aspect, the amino acid at a position corresponding to position 178 is substituted with Ala, Arg, Asn, Asp, Cys, Gln, Glu, Gly, His, lie, Leu, Lys, Met, Phe, Pro, Ser, Thr, Trp or Val. In another aspect, the variant comprises or consists of the substitution Y178F of the polypeptide of SEQ ID NO: 1. In a preferred embodiment a) comprises a pairwise deletion of the amino acids corresponding to H183*+G184* and b) comprises or consists of the substitution Y178F of the polypeptide of SEQ ID NO: 1.

In another aspect, the variant comprises or consists of a substitution at a position corresponding to position 181. In another aspect, the amino acid at a position corresponding to position 181 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R181Q or R181D of the polypeptide of SEQ ID NO: 1. In a preferred embodiment a) comprises a pairwise deletion of the amino acids corresponding to H183*+G184* and b) comprises or consists of the substitution R181 Q or R181D of the polypeptide of SEQ ID NO: 1 In another aspect, the variant comprises or consists of a substitution at a position corresponding to position 182. In another aspect, the amino acid at a position corresponding to position 182 is substituted with Ala, Arg, Asn, Asp, Cys, Gln, Glu, His, lie, Leu, Lys, Met, Phe, Pro, Ser, Thr, Trp, Tyr or Val. In another aspect, the variant comprises or consists of the substitution G182T or G182A of the polypeptide of SEQ ID NO: 1. In a preferred embodiment a) comprises a pairwise deletion of the amino acids corresponding to H183*+G184* and b) comprises or consists of the substitution G182T or G182A of the polypeptide of SEQ ID NO: 1.

In another aspect, the variant comprises or consists of a substitution at a position corresponding to position 186. In another aspect, the amino acid at a position corresponding to position 186 is substituted with Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A186G of the polypeptide of SEQ ID NO: 1. In a preferred embodiment a) comprises a pairwise deletion of the amino acids corresponding to H183*+G184* and b) comprises or consists of the substitution A186G of the polypeptide of SEQ ID NO: 1.

In another aspect, the variant comprises or consists of a substitution at a position corresponding to position 190. In another aspect, the amino acid at a position corresponding to position 190 is substituted with Ala, Arg, Asn, Asp, Cys, Gln, Giy, His, Ile, Leu, Lys, Met, Phe, Pro, Ser, Thr, Trp, Tyr or Val. In another aspect, the variant comprises or consists of the substitution E190P of the polypeptide of SEQ ID NO: 1. In a preferred embodiment a) comprises a pairwise deletion of the amino acids corresponding to H183*+G184* and b) comprises or consists of the substitution E190P of the polypeptide of SEQ ID NO: 1.

In another aspect, the variant comprises or consists of a substitution at a position corresponding to position 192. In another aspect, the amino acid at a position corresponding to position 192 is substituted with Ala, Arg, Asn, Cys, Gln, Glu, Giy, His, Ile, Leu, Lys, Met, Phe, Pro, Ser, Thr, Trp, Tyr or Val. In another aspect, the variant comprises or consists of the substitution D192S of the polypeptide of SEQ ID NO: 1. In a preferred embodiment a) comprises a pairwise deletion of the amino acids corresponding to H183*+G184* and b) comprises or consists of the substitution D192S of the polypeptide of SEQ ID NO: 1.

In another aspect, the variant comprises or consists of a substitution at a position corresponding to position 193. In another aspect, the amino acid at a position corresponding to position 193 is substituted with Ala, Arg, Asn, Asp, Cys, Gln, Glu, Giy, His, Ile, Leu, Lys, Met, Phe, Pro, Ser, Trp, Tyr or Val. In another aspect, the variant comprises or consists of the substitution T193S of the polypeptide of SEQ ID NO: 1. In a preferred embodiment a) comprises a pairwise deletion of the amino acids corresponding to H183*+G184* and b) comprises or consists of the substitution T193S of the polypeptide of SEQ ID NO: 1.

In another aspect, the variant comprises or consists of a substitution at a position corresponding to position 195. In another aspect, the amino acid at a position corresponding to position 195 is substituted with Ala, Arg, Asp, Cys, Gln, Glu, Giy, His, Ile, Leu, Lys, Met, Phe, Pro, Ser, Thr, Trp, Tyr or Val. In another aspect, the variant comprises or consists of the substitution N195F of the polypeptide of SEQ ID NO: 1. In a preferred embodiment a) comprises a pairwise deletion of the amino acids corresponding to H183*+G184* and b) comprises or consists of the substitution N195F of the polypeptide of SEQ ID NO: 1.

In another aspect, the variant comprises or consists of a substitution at a position corresponding to position 206. In another aspect, the amino acid at a position corresponding to position 206 is substituted with Ala, Arg, Asn, Asp, Cys, Gln, Glu, Giy, His, Leu, Lys, Met, Phe, Pro, Ser, Thr, Trp, Tyr or Val. In another aspect, the variant comprises or consists of the substitution I206L or I206Y of the polypeptide of SEQ ID NO: 1. In a preferred embodiment a) comprises a pairwise deletion of the amino acids corresponding to H183*+G184* and b) comprises or consists of the substitution I206L or I206Y of the polypeptide of SEQ ID NO: 1.

In another aspect, the variant comprises or consists of a substitution at a position corresponding to position 208. In another aspect, the amino acid at a position corresponding to position 208 is substituted with Ala, Arg, Asn, Asp, Cys, Gln, Glu, Gly, His, lie, Leu, Lys, Phe, Pro, Ser, Thr, Trp, Tyr or Val. In another aspect, the variant comprises or consists of the substitution M208Y of the polypeptide of SEQ ID NO: 1. In a preferred embodiment a) comprises a pairwise deletion of the amino acids corresponding to H183*+G184* and b) comprises or consists of the substitution M208Y of the polypeptide of SEQ ID NO: 1.

In another aspect, the variant comprises or consists of a substitution at a position corresponding to position 212. In another aspect, the amino acid at a position corresponding to position 212 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E212D of the polypeptide of SEQ ID NO: 1. In a preferred embodiment a) comprises a pairwise deletion of the amino acids corresponding to H183*+G184* and b) comprises or consists of the substitution E212D of the polypeptide of SEQ ID NO: 1.

In another aspect, the variant comprises or consists of a substitution at a position corresponding to position 214. In another aspect, the amino acid at a position corresponding to position 214 is substituted with Ala, Arg, Asn, Asp, Cys, Gln, Glu, Gly, His, lie, Leu, Lys, Met, Phe, Pro, Ser, Thr, Trp or Tyr. In another aspect, the variant comprises or consists of the substitution V214I or V214A of the polypeptide of SEQ ID NO: 1. In a preferred embodiment a) comprises a pairwise deletion of the amino acids corresponding to H183*+G184* and b) comprises or consists of the substitution V214I or V214A of the polypeptide of SEQ ID NO: 1.

In another aspect, the variant comprises or consists of a substitution at a position corresponding to position 217. In another aspect, the amino acid at a position corresponding to position 217 is substituted with Ala, Arg, Asn, Asp, Cys, Gln, Glu, Gly, His, lie, Lys, Met, Phe, Pro, Ser, Thr, Trp, Tyr or Val. In another aspect, the variant comprises or consists of the substitution L217I or L217M of the polypeptide of SEQ ID NO: 1. In a preferred embodiment a) comprises a pairwise deletion of the amino acids corresponding to H183*+G184* and b) comprises or consists of the substitution L217I or L217M of the polypeptide of SEQ ID NO: 1.

In another aspect, the variant comprises or consists of a substitution at a position corresponding to position 218. In another aspect, the amino acid at a position corresponding to position 218 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R218K or R218N of the polypeptide of SEQ ID NO: 1. In a preferred embodiment a) comprises a pairwise deletion of the amino acids corresponding to H183*+G184* and b) comprises or consists of the substitution R218K or R218N of the polypeptide of SEQ ID NO: 1.

In another aspect, the variant comprises or consists of a substitution at a position corresponding to position 219. In another aspect, the amino acid at a position corresponding to position 219 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N219K or N219R of the polypeptide of SEQ ID NO: 1. In a preferred embodiment a) comprises a pairwise deletion of the amino acids corresponding to H183*+G184* and b) comprises or consists of the substitution N219K or N219R of the polypeptide of SEQ ID NO: 1.

In another aspect, the variant comprises or consists of a substitution at a position corresponding to position 222. In another aspect, the amino acid at a position corresponding to position 222 is substituted with Ala, Arg, Asn, Asp, Cys, Gln, Glu, Gly, His, lie, Leu, Lys, Met, Phe, Pro, Ser, Thr, Trp or Tyr. In another aspect, the variant comprises or consists of the substitution V222T of the polypeptide of SEQ ID NO: 1. In a preferred embodiment a) comprises a pairwise deletion of the amino acids corresponding to H183*+G184* and b) comprises or consists of the substitution V222T of the polypeptide of SEQ ID NO: 1.

In another aspect, the variant comprises or consists of a substitution at a position corresponding to position 225. In another aspect, the amino acid at a position corresponding to position 225 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T225A of the polypeptide of SEQ ID NO: 1. In a preferred embodiment a) comprises a pairwise deletion of the amino acids corresponding to H183*+G184* and b) comprises or consists of the substitution T225A of the polypeptide of SEQ ID NO: 1.

In another aspect, the variant comprises or consists of a substitution at a position corresponding to position 227. In another aspect, the amino acid at a position corresponding to position 227 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T227E of the polypeptide of SEQ ID NO: 1. In a preferred embodiment a) comprises a pairwise deletion of the amino acids corresponding to H183*+G184* and b) comprises or consists of the substitution T227E of the polypeptide of SEQ ID NO: 1.

In another aspect, the variant comprises or consists of a substitution at a position corresponding to position 228. In another aspect, the amino acid at a position corresponding to position 228 is substituted with Ala, Arg, Asn, Asp, Cys, Gln, Glu, Gly, His, lie, Lys, Met, Phe, Pro, Ser, Thr, Trp, Tyr or Val. In another aspect, the variant comprises or consists of the substitution L228V of the polypeptide of SEQ ID NO: 1. In a preferred embodiment a) comprises a pairwise deletion of the amino acids corresponding to H183*+G184* and b) comprises or consists of the substitution L228V of the polypeptide of SEQ ID NO: 1.

In another aspect, the variant comprises or consists of a substitution at a position corresponding to position 229. In another aspect, the amino acid at a position corresponding to position 229 is substituted with Ala, Arg, Asn, Asp, Cys, Gln, Glu, His, lie, Leu, Lys, Met, Phe, Pro, Ser, Thr, Trp, Tyr or Val. In another aspect, the variant comprises or consists of the substitution G229Q of the polypeptide of SEQ ID NO: 1. In a preferred embodiment a) comprises a pairwise deletion of the amino acids corresponding to H183*+G184* and b) comprises or consists of the substitution G229Q of the polypeptide of SEQ ID NO: 1.

In another aspect, the variant comprises or consists of a substitution at a position corresponding to position 233. In another aspect, the amino acid at a position corresponding to position 233 is substituted with Ala, Arg, Asn, Asp, Cys, Gln, Glu, Gly, His, lie, Leu, Lys, Met, Pro, Ser, Thr, Trp, Tyr or Val. In another aspect, the variant comprises or consists of the substitution F233Y of the polypeptide of SEQ ID NO: 1. In a preferred embodiment a) comprises a pairwise deletion of the amino acids corresponding to H183*+G184* and b) comprises or consists of the substitution F233Y of the polypeptide of SEQ ID NO: 1.

In another aspect, the variant comprises or consists of a substitution at a position corresponding to position 235. In another aspect, the amino acid at a position corresponding to position 235 is substituted with Ala, Arg, Asn, Asp, Cys, Gln, Glu, Gly, His, Leu, Lys, Met, Phe, Pro, Ser, Thr, Trp, Tyr or Val. In another aspect, the variant comprises or consists of the substitution I235L of the polypeptide of SEQ ID NO: 1. In a preferred embodiment a) comprises a pairwise deletion of the amino acids corresponding to H183*+G184* and b) comprises or consists of the substitution I235L of the polypeptide of SEQ ID NO: 1.

In another aspect, the variant comprises or consists of a substitution at a position corresponding to position 243. In another aspect, the amino acid at a position corresponding to position 243 is substituted with Ala, Arg, Asn, Asp, Cys, Gln, Glu, Gly, His, lie, Leu, Lys, Met, Phe, Pro, Ser, Thr, Trp or Val. In another aspect, the variant comprises or consists of the substitution Y243F of the polypeptide of SEQ ID NO: 1. In a preferred embodiment a) comprises a pairwise deletion of the amino acids corresponding to H183*+G184* and b) comprises or consists of the substitution Y243F of the polypeptide of SEQ ID NO: 1.

In another aspect, the variant comprises or consists of a substitution at a position corresponding to position 246. In another aspect, the amino acid at a position corresponding to position 246 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T246M or T246L of the polypeptide of SEQ ID NO: 1. In a preferred embodiment a) comprises a pairwise deletion of the amino acids corresponding to H183*+G184* and b) comprises or consists of the substitution T246M or T246L of the polypeptide of SEQ ID NO: 1.

In another aspect, the variant comprises or consists of a substitution at a position corresponding to position 247. In another aspect, the amino acid at a position corresponding to position 247 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R247K of the polypeptide of SEQ ID NO: 1. In a preferred embodiment a) comprises a pairwise deletion of the amino acids corresponding to H183*+G184* and b) comprises or consists of the substitution R247K of the polypeptide of SEQ ID NO: 1.

In another aspect, the variant comprises or consists of a substitution at a position corresponding to position 250. In another aspect, the amino acid at a position corresponding to position 250 is substituted with Ala, Arg, Asn, Asp, Cys, Gln, Glu, Gly, His, Leu, Lys, Met, Phe, Pro, Ser, Thr, Trp, Tyr or Val. In another aspect, the variant comprises or consists of the substitution 1250L or 1250V of the polypeptide of SEQ ID NO: 1. In a preferred embodiment a) comprises a pairwise deletion of the amino acids corresponding to H183*+G184* and b) comprises or consists of the substitution 1250L or 1250V of the polypeptide of SEQ ID NO: 1.

In another aspect, the variant comprises or consists of a substitution at a position corresponding to position 251. In another aspect, the amino acid at a position corresponding to position 251 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N251 D or N251G of the polypeptide of SEQ ID NO: 1. In a preferred embodiment a) comprises a pairwise deletion of the amino acids corresponding to H183*+G184* and b) comprises or consists of the substitution N251 D or N251G of the polypeptide of SEQ ID NO: 1.

In another aspect, the variant comprises or consists of a substitution at a position corresponding to position 252. In another aspect, the amino acid at a position corresponding to position 252 is substituted with Ala, Arg, Asn, Asp, Cys, Gln, Glu, Gly, lie, Leu, Lys, Met, Phe, Pro, Ser, Thr, Trp, Tyr or Val. In another aspect, the variant comprises or consists of the substitution H252N of the polypeptide of SEQ ID NO: 1. In a preferred embodiment a) comprises a pairwise deletion of the amino acids corresponding to H183*+G184* and b) comprises or consists of the substitution H252N of the polypeptide of SEQ ID NO: 1.

In another aspect, the variant comprises or consists of a substitution at a position corresponding to position 253. In another aspect, the amino acid at a position corresponding to position 253 is substituted with Ala, Arg, Asn, Asp, Cys, Gln, Glu, Gly, His, lie, Leu, Lys, Met, Phe, Pro, Ser, Thr, Trp or Tyr. In another aspect, the variant comprises or consists of the substitution V253A of the polypeptide of SEQ ID NO: 1. In a preferred embodiment a) comprises a pairwise deletion of the amino acids corresponding to H183*+G184* and b) comprises or consists of the substitution V253A of the polypeptide of SEQ ID NO: 1.

In another aspect, the variant comprises or consists of a substitution at a position corresponding to position 255. In another aspect, the amino acid at a position corresponding to position 255 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S255E or S255G or S255A of the polypeptide of SEQ ID NO: 1. In a preferred embodiment a) comprises a pairwise deletion of the amino acids corresponding to H183*+G184* and b) comprises or consists of the substitution S255E or S255G or S255A of the polypeptide of SEQ ID NO: 1.

In another aspect, the variant comprises or consists of a substitution at a position corresponding to position 256. In another aspect, the amino acid at a position corresponding to position 256 is substituted with Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A256Q or A256K of the polypeptide of SEQ ID NO: 1. In a preferred embodiment a) comprises a pairwise deletion of the amino acids corresponding to H183*+G184* and b) comprises or consists of the substitution A256Q or A256K of the polypeptide of SEQ ID NO: 1.

In another aspect, the variant comprises or consists of a substitution at a position corresponding to position 260. In another aspect, the amino acid at a position corresponding to position 260 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N260E or N260G of the polypeptide of SEQ ID NO: 1. In a preferred embodiment a) comprises a pairwise deletion of the amino acids corresponding to H183*+G184* and b) comprises or consists of the substitution N260E or N260G of the polypeptide of SEQ ID NO: 1.

In another aspect, the variant comprises or consists of a substitution at a position corresponding to position 261. In another aspect, the amino acid at a position corresponding to position 261 is substituted with Ala, Arg, Asn, Asp, Cys, Gln, Glu, Gly, His, lie, Leu, Lys, Phe, Pro, Ser, Thr, Trp, Tyr or Val. In another aspect, the variant comprises or consists of the substitution M261 L of the polypeptide of SEQ ID NO: 1. In a preferred embodiment a) comprises a pairwise deletion of the amino acids corresponding to H183*+G184* and b) comprises or consists of the substitution M261 L of the polypeptide of SEQ ID NO: 1.

In another aspect, the variant comprises or consists of a substitution at a position corresponding to position 263. In another aspect, the amino acid at a position corresponding to position 263 is substituted with Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A263T of the polypeptide of SEQ ID NO: 1. In a preferred embodiment a) comprises a pairwise deletion of the amino acids corresponding to H183*+G184* and b) comprises or consists of the substitution A263T of the polypeptide of SEQ ID NO: 1.

In another aspect, the variant comprises or consists of a substitution at a position corresponding to position 265. In another aspect, the amino acid at a position corresponding to position 265 is substituted with Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A265G of the polypeptide of SEQ ID NO: 1. In a preferred embodiment a) comprises a pairwise deletion of the amino acids corresponding to H183*+G184* and b) comprises or consists of the substitution A265G of the polypeptide of SEQ ID NO: 1. In another aspect, the variant comprises or consists of a substitution at a position corresponding to position 267. In another aspect, the amino acid at a position corresponding to position 267 is substituted with Ala, Arg, Asn, Asp, Cys, Gln, Glu, Gly, His, lie, Leu, Lys, Met, Pro, Ser, Thr, Trp, Tyr or Val. In another aspect, the variant comprises or consists of the substitution F267Y of the polypeptide of SEQ ID NO: 1. In a preferred embodiment a) comprises a pairwise deletion of the amino acids corresponding to H183*+G184* and b) comprises or consists of the substitution F267Y of the polypeptide of SEQ ID NO: 1.

In another aspect, the variant comprises or consists of a substitution at a position corresponding to position 269. In another aspect, the amino acid at a position corresponding to position 269 is substituted with Ala, Arg, Asn, Asp, Cys, Gln, Glu, Gly, His, lie, Leu, Met, Phe, Pro, Ser, Thr, Trp, Tyr or Val. In another aspect, the variant comprises or consists of the substitution K269Q of the polypeptide of SEQ ID NO: 1. In a preferred embodiment a) comprises a pairwise deletion of the amino acids corresponding to H183*+G184* and b) comprises or consists of the substitution K269Q of the polypeptide of SEQ ID NO: 1.

In another aspect, the variant comprises or consists of a substitution at a position corresponding to position 275. In another aspect, the amino acid at a position corresponding to position 275 is substituted with Ala, Arg, Asn, Asp, Cys, Gln, Glu, Gly, His, Leu, Lys, Met, Phe, Pro, Ser, Thr, Trp, Tyr or Val. In another aspect, the variant comprises or consists of the substitution I275L of the polypeptide of SEQ ID NO: 1. In a preferred embodiment a) comprises a pairwise deletion of the amino acids corresponding to H183*+G184* and b) comprises or consists of the substitution I275L of the polypeptide of SEQ ID NO: 1.

In another aspect, the variant comprises or consists of a substitution at a position corresponding to position 276. In another aspect, the amino acid at a position corresponding to position 276 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E276N of the polypeptide of SEQ ID NO: 1. In a preferred embodiment a) comprises a pairwise deletion of the amino acids corresponding to H183*+G184* and b) comprises or consists of the substitution E276N of the polypeptide of SEQ ID NO: 1.

In another aspect, the variant comprises or consists of a substitution at a position corresponding to position 280. In another aspect, the amino acid at a position corresponding to position 280 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution Q280A or Q280N or Q280T of the polypeptide of SEQ ID NO: 1. In a preferred embodiment a) comprises a pairwise deletion of the amino acids corresponding to H183*+G184* and b) comprises or consists of the substitution Q280A or Q280N or Q280T of the polypeptide of SEQ ID NO: 1.

In another aspect, the variant comprises or consists of a substitution at a position corresponding to position 281. In another aspect, the amino acid at a position corresponding to position 281 is substituted with Ala, Arg, Asn, Asp, Cys, Gln, Glu, Gly, His, lie, Leu, Met, Phe, Pro, Ser, Thr, Trp, Tyr or Val. In another aspect, the variant comprises or consists of the substitution K281Y or K281 F of the polypeptide of SEQ ID NO: 1. In a preferred embodiment a) comprises a pairwise deletion of the amino acids corresponding to H183*+G184* and b) comprises or consists of the substitution K281Y or K281F of the polypeptide of SEQ ID NO: 1.

In another aspect, the variant comprises or consists of a substitution at a position corresponding to position 282. In another aspect, the amino acid at a position corresponding to position 282 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T282V of the polypeptide of SEQ ID NO: 1. In a preferred embodiment a) comprises a pairwise deletion of the amino acids corresponding to H183*+G184* and b) comprises or consists of the substitution T282V of the polypeptide of SEQ ID NO: 1.

In another aspect, the variant comprises or consists of a substitution at a position corresponding to position 284. In another aspect, the amino acid at a position corresponding to position 284 is substituted with Ala, Arg, Asn, Asp, Cys, Gln, Glu, Gly, His, lie, Leu, Lys, Met, Phe, Pro, Ser, Thr, Trp or Val. In another aspect, the variant comprises or consists of the substitution W284Y or W284F of the polypeptide of SEQ ID NO: 1. In a preferred embodiment a) comprises a pairwise deletion of the amino acids corresponding to H183*+G184* and b) comprises or consists of the substitution W284Y or W284F of the polypeptide of SEQ ID NO: 1.

In another aspect, the variant comprises or consists of a substitution at a position corresponding to position 285. In another aspect, the amino acid at a position corresponding to position 285 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N285T of the polypeptide of SEQ ID NO: 1. In a preferred embodiment a) comprises a pairwise deletion of the amino acids corresponding to H183*+G184* and b) comprises or consists of the substitution N285T of the polypeptide of SEQ ID NO: 1.

In another aspect, the variant comprises or consists of a substitution at a position corresponding to position 286. In another aspect, the amino acid at a position corresponding to position 286 is substituted with Ala, Arg, Asn, Asp, Cys, Gln, Glu, Gly, lie, Leu, Lys, Met, Phe, Pro, Ser, Thr, Trp, Tyr or Val. In another aspect, the variant comprises or consists of the substitution H286Q or H286M of the polypeptide of SEQ ID NO: 1. In a preferred embodiment a) comprises a pairwise deletion of the amino acids corresponding to H183*+G184* and b) comprises or consists of the substitution H286Q or H286M of the polypeptide of SEQ ID NO: 1.

In another aspect, the variant comprises or consists of a substitution at a position corresponding to position 288. In another aspect, the amino acid at a position corresponding to position 288 is substituted with Ala, Arg, Asn, Asp, Cys, Gln, Glu, Gly, His, lie, Leu, Lys, Met, Phe, Pro, Ser, Thr, Trp or Tyr. In another aspect, the variant comprises or consists of the substitution V288L or V288A of the polypeptide of SEQ ID NO: 1. In a preferred embodiment a) comprises a pairwise deletion of the amino acids corresponding to H183*+G184* and b) comprises or consists of the substitution V288L or V288A of the polypeptide of SEQ ID NO: 1.

In another aspect, the variant comprises or consists of a substitution at a position corresponding to position 291. In another aspect, the amino acid at a position corresponding to position 291 is substituted with Ala, Arg, Asn, Asp, Cys, Gln, Glu, Gly, His, lie, Leu, Lys, Met, Phe, Pro, Ser, Thr, Trp, or Tyr. In another aspect, the variant comprises or consists of the substitution V291A of the polypeptide of SEQ ID NO: 1. In a preferred embodiment a) comprises a pairwise deletion of the amino acids corresponding to H183*+G184* and b) comprises or consists of the substitution V291A of the polypeptide of SEQ ID NO: 1.

In another aspect, the variant comprises or consists of a substitution at a position corresponding to position 296. In another aspect, the amino acid at a position corresponding to position 296 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N296Q of the polypeptide of SEQ ID NO: 1. In a preferred embodiment a) comprises a pairwise deletion of the amino acids corresponding to H183*+G184* and b) comprises or consists of the substitution N296Q of the polypeptide of SEQ ID NO: 1.

In another aspect, the variant comprises or consists of a substitution at a position corresponding to position 297. In another aspect, the amino acid at a position corresponding to position 297 is substituted with Ala, Arg, Asn, Asp, Cys, Gln, Glu, Gly, His, lie, Lys, Met, Phe, Pro, Ser, Thr, Trp, Tyr or Val. In another aspect, the variant comprises or consists of the substitution L297F of the polypeptide of SEQ ID NO: 1. In a preferred embodiment a) comprises a pairwise deletion of the amino acids corresponding to H183*+G184* and b) comprises or consists of the substitution L297F of the polypeptide of SEQ ID NO: 1.

In another aspect, the variant comprises or consists of a substitution at a position corresponding to position 299. In another aspect, the amino acid at a position corresponding to position 299 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N299A or N299S of the polypeptide of SEQ ID NO: 1. In a preferred embodiment a) comprises a pairwise deletion of the amino acids corresponding to H183*+G184* and b) comprises or consists of the substitution N299A or N299S of the polypeptide of SEQ ID NO: 1.

In another aspect, the variant comprises or consists of a substitution at a position corresponding to position 302. In another aspect, the amino acid at a position corresponding to position 302 is substituted with Ala, Arg, Asn, Asp, Cys, Gln, Glu, Gly, His, lie, Leu, Met, Phe, Pro, Ser, Thr, Trp, Tyr or Val. In another aspect, the variant comprises or consists of the substitution K302N or K302T of the polypeptide of SEQ ID NO: 1. In a preferred embodiment a) comprises a pairwise deletion of the amino acids corresponding to H183*+G184* and b) comprises or consists of the substitution K302N or K302T of the polypeptide of SEQ ID NO: 1.

In another aspect, the variant comprises or consists of a substitution at a position corresponding to position 303. In another aspect, the amino acid at a position corresponding to position 303 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S303G of the polypeptide of SEQ ID NO: 1. In a preferred embodiment a) comprises a pairwise deletion of the amino acids corresponding to H183*+G184* and b) comprises or consists of the substitution S303G of the polypeptide of SEQ ID NO: 1.

In another aspect, the variant comprises or consists of a substitution at a position corresponding to position 304. In another aspect, the amino acid at a position corresponding to position 304 is substituted with Ala, Arg, Asn, Asp, Cys, Gln, Glu, His, lie, Leu, Lys, Met, Phe, Pro, Ser, Thr, Trp, Tyr or Val. In another aspect, the variant comprises or consists of the substitution G304S of the polypeptide of SEQ ID NO: 1. In a preferred embodiment a) comprises a pairwise deletion of the amino acids corresponding to H183*+G184* and b) comprises or consists of the substitution G304S of the polypeptide of SEQ ID NO: 1.

In another aspect, the variant comprises or consists of a substitution at a position corresponding to position 306. In another aspect, the amino acid at a position corresponding to position 306 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N306Y of the polypeptide of SEQ ID NO: 1. In a preferred embodiment a) comprises a pairwise deletion of the amino acids corresponding to H183*+G184* and b) comprises or consists of the substitution N306Y of the polypeptide of SEQ ID NO: 1.

In another aspect, the variant comprises or consists of a substitution at a position corresponding to position 311. In another aspect, the amino acid at a position corresponding to position 311 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N311K N311 Q of the polypeptide of SEQ ID NO: 1. In a preferred embodiment a) comprises a pairwise deletion of the amino acids corresponding to H183*+G184* and b) comprises or consists of the substitution N311K N311 Q of the polypeptide of SEQ ID NO: 1.

In another aspect, the variant comprises or consists of a substitution at a position corresponding to position 312. In another aspect, the amino acid at a position corresponding to position 312 is substituted with Ala, Arg, Asn, Asp, Cys, Gln, Glu, Gly, His, Leu, Lys, Met, Phe, Pro, Ser, Thr, Trp, Tyr or Val. In another aspect, the variant comprises or consists of the substitution I312L of the polypeptide of SEQ ID NO: 1. In a preferred embodiment a) comprises a pairwise deletion of the amino acids corresponding to H183*+G184* and b) comprises or consists of the substitution I312L of the polypeptide of SEQ ID NO: 1.

In another aspect, the variant comprises or consists of a substitution at a position corresponding to position 313. In another aspect, the amino acid at a position corresponding to position 313 is substituted with Ala, Arg, Asn, Asp, Cys, Gln, Glu, Gly, His, lie, Leu, Lys, Met, Pro, Ser, Thr, Trp, Tyr or Val. In another aspect, the variant comprises or consists of the substitution F313L of the polypeptide of SEQ ID NO: 1. In a preferred embodiment a) comprises a pairwise deletion of the amino acids corresponding to H183*+G184* and b) comprises or consists of the substitution F313L of the polypeptide of SEQ ID NO: 1.

In another aspect, the variant comprises or consists of a substitution at a position corresponding to position 315. In another aspect, the amino acid at a position corresponding to position 315 is substituted with Ala, Arg, Asn, Asp, Cys, Gln, Glu, His, lie, Leu, Lys, Met, Phe, Pro, Ser, Thr, Trp, Tyr or Val. In another aspect, the variant comprises or consists of the substitution G315N of the polypeptide of SEQ ID NO: 1. In a preferred embodiment a) comprises a pairwise deletion of the amino acids corresponding to H183*+G184* and b) comprises or consists of the substitution G315N of the polypeptide of SEQ ID NO: 1.

In another aspect, the variant comprises or consists of a substitution at a position corresponding to position 317. In another aspect, the amino acid at a position corresponding to position 317 is substituted with Ala, Arg, Asn, Asp, Cys, Gln, Glu, Gly, His, lie, Leu, Lys, Met, Phe, Pro, Ser, Thr, Trp, or Tyr. In another aspect, the variant comprises or consists of the substitution V317L of the polypeptide of SEQ ID NO: 1. In a preferred embodiment a) comprises a pairwise deletion of the amino acids corresponding to H183*+G184* and b) comprises or consists of the substitution V317L of the polypeptide of SEQ ID NO: 1.

In another aspect, the variant comprises or consists of a substitution at a position corresponding to position 319. In another aspect, the amino acid at a position corresponding to position 319 is substituted with Ala, Arg, Asn, Asp, Cys, Glu, Gly, His, lie, Leu, Lys, Met, Phe, Pro, Ser, Thr, Trp, Tyr or Val. In another aspect, the variant comprises or consists of the substitution Q319A or Q319S of the polypeptide of SEQ ID NO: 1. In a preferred embodiment a) comprises a pairwise deletion of the amino acids corresponding to H183*+G184* and b) comprises or consists of the substitution Q319A or Q319S of the polypeptide of SEQ ID NO: 1.

In another aspect, the variant comprises or consists of a substitution at a position corresponding to position 320. In another aspect, the amino acid at a position corresponding to position 320 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R320S or R320K of the polypeptide of SEQ ID NO: 1. In a preferred embodiment a) comprises a pairwise deletion of the amino acids corresponding to H183*+G184* and b) comprises or consists of the substitution R320S or R320K of the polypeptide of SEQ ID NO: 1.

In another aspect, the variant comprises or consists of a substitution at a position corresponding to position 321. In another aspect, the amino acid at a position corresponding to position 321 is substituted with Ala, Arg, Asn, Asp, Cys, Gln, Glu, Gly, lie, Leu, Lys, Met, Phe, Pro, Ser, Thr, Trp, Tyr or Val. In another aspect, the variant comprises or consists of the substitution H321N of the polypeptide of SEQ ID NO: 1. In a preferred embodiment a) comprises a pairwise deletion of the amino acids corresponding to H183*+G184* and b) comprises or consists of the substitution H321N of the polypeptide of SEQ ID NO: 1.

In another aspect, the variant comprises or consists of a substitution at a position corresponding to position 323. In another aspect, the amino acid at a position corresponding to position 323 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution S323L or S323T or S323M of the polypeptide of SEQ ID NO: 1. In a preferred embodiment a) comprises a pairwise deletion of the amino acids corresponding to H183*+G184* and b) comprises or consists of the substitution S323L or S323T or S323M of the polypeptide of SEQ ID NO: 1.

In another aspect, the variant comprises or consists of a substitution at a position corresponding to position 324. In another aspect, the amino acid at a position corresponding to position 324 is substituted with Ala, Arg, Asn, Asp, Cys, Gln, Glu, Gly, lie, Leu, Lys, Met, Phe, Pro, Ser, Thr, Trp, Tyr or Val. In another aspect, the variant comprises or consists of the substitution H324K of the polypeptide of SEQ ID NO: 1. In a preferred embodiment a) comprises a pairwise deletion of the amino acids corresponding to H183*+G184* and b) comprises or consists of the substitution H324K of the polypeptide of SEQ ID NO: 1.

In another aspect, the variant comprises or consists of a substitution at a position corresponding to position 325. In another aspect, the amino acid at a position corresponding to position 325 is substituted with Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A325S of the polypeptide of SEQ ID NO: 1. In a preferred embodiment a) comprises a pairwise deletion of the amino acids corresponding to H183*+G184* and b) comprises or consists of the substitution A325S of the polypeptide of SEQ ID NO: 1.

In another aspect, the variant comprises or consists of a substitution at a position corresponding to position 328. In another aspect, the amino acid at a position corresponding to position 328 is substituted with Ala, Arg, Asn, Asp, Cys, Gln, Glu, Gly, His, lie, Leu, Lys, Met, Pro, Ser, Thr, Trp, Tyr or Val. In another aspect, the variant comprises or consists of the substitution F328L of the polypeptide of SEQ ID NO: 1. In a preferred embodiment a) comprises a pairwise deletion of the amino acids corresponding to H183*+G184* and b) comprises or consists of the substitution F328L of the polypeptide of SEQ ID NO: 1.

In another aspect, the variant comprises or consists of a substitution at a position corresponding to position 330. In another aspect, the amino acid at a position corresponding to position 330 is substituted with Ala, Arg, Asn, Cys, Gln, Glu, Gly, His, lie, Leu, Lys, Met, Phe, Pro, Ser, Thr, Trp, Tyr or Val. In another aspect, the variant comprises or consists of the substitution D330E of the polypeptide of SEQ ID NO: 1. In a preferred embodiment a) comprises a pairwise deletion of the amino acids corresponding to H183*+G184* and b) comprises or consists of the substitution D330E of the polypeptide of SEQ ID NO: 1.

In another aspect, the variant comprises or consists of a substitution at a position corresponding to position 334. In another aspect, the amino acid at a position corresponding to position 334 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S334T of the polypeptide of SEQ ID NO: 1. In a preferred embodiment a) comprises a pairwise deletion of the amino acids corresponding to H183*+G184* and b) comprises or consists of the substitution S334T of the polypeptide of SEQ ID NO: 1.

In another aspect, the variant comprises or consists of a substitution at a position corresponding to position 337. In another aspect, the amino acid at a position corresponding to position 337 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E337G of the polypeptide of SEQ ID NO: 1. In a preferred embodiment a) comprises a pairwise deletion of the amino acids corresponding to H183*+G184* and b) comprises or consists of the substitution E337G of the polypeptide of SEQ ID NO: 1.

In another aspect, the variant comprises or consists of a substitution at a position corresponding to position 338. In another aspect, the amino acid at a position corresponding to position 338 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E338Q of the polypeptide of SEQ ID NO: 1. In a preferred embodiment a) comprises a pairwise deletion of the amino acids corresponding to H183*+G184* and b) comprises or consists of the substitution E338Q of the polypeptide of SEQ ID NO: 1.

In another aspect, the variant comprises or consists of a substitution at a position corresponding to position 339. In another aspect, the amino acid at a position corresponding to position 339 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A339S of the polypeptide of SEQ ID NO: 1. In a preferred embodiment a) comprises a pairwise deletion of the amino acids corresponding to H183*+G184* and b) comprises or consists of the substitution A339S of the polypeptide of SEQ ID NO: 1.

In another aspect, the variant comprises or consists of a substitution at a position corresponding to position 343. In another aspect, the amino acid at a position corresponding to position 343 is substituted with Ala, Arg, Asn, Asp, Cys, Gln, Glu, Gly, His, lie, Leu, Lys, Met, Pro, Ser, Thr, Trp, Tyr or Val. In another aspect, the variant comprises or consists of the substitution F343T of the polypeptide of SEQ ID NO: 1. In a preferred embodiment a) comprises a pairwise deletion of the amino acids corresponding to H183*+G184* and b) comprises or consists of the substitution F343T of the polypeptide of SEQ ID NO: 1.

In another aspect, the variant comprises or consists of a substitution at a position corresponding to position 345. In another aspect, the amino acid at a position corresponding to position 345 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E345Q of the polypeptide of SEQ ID NO: 1. In a preferred embodiment a) comprises a pairwise deletion of the amino acids corresponding to H183*+G184* and b) comprises or consists of the substitution E345Q of the polypeptide of SEQ ID NO: 1.

In another aspect, the variant comprises or consists of a substitution at a position corresponding to position 346. In another aspect, the amino acid at a position corresponding to position 346 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E346T or E346P of the polypeptide of SEQ ID NO: 1. In a preferred embodiment a) comprises a pairwise deletion of the amino acids corresponding to H183*+G184* and b) comprises or consists of the substitution E346T or E346P of the polypeptide of SEQ ID NO: 1.

In another aspect, the variant comprises or consists of a substitution at a position corresponding to position 347. In another aspect, the amino acid at a position corresponding to position 347 is substituted with Ala, Arg, Asn, Asp, Cys, Gln, Glu, Gly, His, lie, Leu, Lys, Met, Phe, Pro, Ser, Thr, Tyr or Val. In another aspect, the variant comprises or consists of the substitution W347R of the polypeptide of SEQ ID NO: 1. In a preferred embodiment a) comprises a pairwise deletion of the amino acids corresponding to H183*+G184* and b) comprises or consists of the substitution W347R of the polypeptide of SEQ ID NO: 1.

In another aspect, the variant comprises or consists of a substitution at a position corresponding to position 355. In another aspect, the amino acid at a position corresponding to position 355 is substituted with Ala, Arg, Asn, Asp, Cys, Gln, Glu, Gly, His, lie, Lys, Met, Phe, Pro, Ser, Thr, Trp, Tyr or Val. In another aspect, the variant comprises or consists of the substitution L355F or L355T of the polypeptide of SEQ ID NO: 1. In a preferred embodiment a) comprises a pairwise deletion of the amino acids corresponding to H183*+G184* and b) comprises or consists of the substitution L355F or L355T of the polypeptide of SEQ ID NO: 1.

In another aspect, the variant comprises or consists of a substitution at a position corresponding to position 356. In another aspect, the amino acid at a position corresponding to position 356 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T356I of the polypeptide of SEQ ID NO: 1. In a preferred embodiment a) comprises a pairwise deletion of the amino acids corresponding to H183*+G184* and b) comprises or consists of the substitution T356I of the polypeptide of SEQ ID NO: 1.

In another aspect, the variant comprises or consists of a substitution at a position corresponding to position 360. In another aspect, the amino acid at a position corresponding to position 360 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E360S of the polypeptide of SEQ ID NO: 1. In a preferred embodiment a) comprises a pairwise deletion of the amino acids corresponding to H183*+G184* and b) comprises or consists of the substitution E360S of the polypeptide of SEQ ID NO: 1.

In another aspect, the variant comprises or consists of a substitution at a position corresponding to position 361. In another aspect, the amino acid at a position corresponding to position 361 is substituted with Ala, Arg, Asn, Asp, Cys, Glu, Gly, His, lie, Leu, Lys, Met, Phe, Pro, Ser, Thr, Trp, Tyr or Val. In another aspect, the variant comprises or consists of the substitution Q361G or Q361S of the polypeptide of SEQ ID NO: 1. In a preferred embodiment a) comprises a pairwise deletion of the amino acids corresponding to H183*+G184* and b) comprises or consists of the substitution Q361G or Q361S of the polypeptide of SEQ ID NO: 1.

In another aspect, the variant comprises or consists of a substitution at a position corresponding to position 371. In another aspect, the amino acid at a position corresponding to position 371 is substituted with Ala, Arg, Asn, Asp, Cys, Gln, Glu, Gly, His, lie, Leu, Lys, Met, Phe, Pro, Ser, Thr, Trp or Val. In another aspect, the variant comprises or consists of the substitution Y371M of the polypeptide of SEQ ID NO: 1. In a preferred embodiment a) comprises a pairwise deletion of the amino acids corresponding to H183*+G184* and b) comprises or consists of the substitution Y371M of the polypeptide of SEQ ID NO: 1.

In another aspect, the variant comprises or consists of a substitution at a position corresponding to position 374. In another aspect, the amino acid at a position corresponding to position 374 is substituted with Ala, Arg, Asn, Asp, Cys, Gln, Glu, Gly, His, Leu, Lys, Met, Phe, Pro, Ser, Thr, Trp, Tyr or Val. In another aspect, the variant comprises or consists of the substitution 1374T of the polypeptide of SEQ ID NO: 1. In a preferred embodiment a) comprises a pairwise deletion of the amino acids corresponding to H183*+G184* and b) comprises or consists of the substitution 1374T of the polypeptide of SEQ ID NO: 1.

In another aspect, the variant comprises or consists of a substitution at a position corresponding to position 375. In another aspect, the amino acid at a position corresponding to position 375 is substituted with Ala, Arg, Asn, Asp, Cys, Gln, Glu, Gly, His, lie, Leu, Lys, Met, Phe, Ser, Thr, Trp, Tyr or Val. In another aspect, the variant comprises or consists of the substitution P375T or P375S of the polypeptide of SEQ ID NO: 1. In a preferred embodiment a) comprises a pairwise deletion of the amino acids corresponding to H183*+G184* and b) comprises or consists of the substitution P375T or P375S of the polypeptide of SEQ ID NO: 1.

In another aspect, the variant comprises or consists of a substitution at a position corresponding to position 376. In another aspect, the amino acid at a position corresponding to position 376 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T376S or T376Q of the polypeptide of SEQ ID NO: 1. In a preferred embodiment a) comprises a pairwise deletion of the amino acids corresponding to H183*+G184* and b) comprises or consists of the substitution T376S or T376Q of the polypeptide of SEQ ID NO: 1.

In another aspect, the variant comprises or consists of a substitution at a position corresponding to position 377. In another aspect, the amino acid at a position corresponding to position 377 is substituted with Ala, Arg, Asn, Asp, Cys, Gln, Glu, Gly, lie, Leu, Lys, Met, Phe, Pro, Ser, Thr, Trp, Tyr or Val. In another aspect, the variant comprises or consists of the substitution H377R or H377D of the polypeptide of SEQ ID NO: 1. In a preferred embodiment a) comprises a pairwise deletion of the amino acids corresponding to H183*+G184* and b) comprises or consists of the substitution H377R or H377D of the polypeptide of SEQ ID NO: 1.

In another aspect, the variant comprises or consists of a substitution at a position corresponding to position 378. In another aspect, the amino acid at a position corresponding to position 378 is substituted with Ala, Arg, Asn, Asp, Cys, Gln, Glu, His, lie, Leu, Lys, Met, Phe, Pro, Ser, Thr, Trp, Tyr or Val. In another aspect, the variant comprises or consists of the substitution G378E of the polypeptide of SEQ ID NO: 1. In a preferred embodiment a) comprises a pairwise deletion of the amino acids corresponding to H183*+G184* and b) comprises or consists of the substitution G378E of the polypeptide of SEQ ID NO: 1.

In another aspect, the variant comprises or consists of a substitution at a position corresponding to position 379. In another aspect, the amino acid at a position corresponding to position 379 is substituted with Ala, Arg, Asn, Asp, Cys, Gln, Glu, Gly, His, lie, Leu, Lys, Met, Phe, Pro, Ser, Thr, Trp or Tyr. In another aspect, the variant comprises or consists of the substitution V379I of the polypeptide of SEQ ID NO: 1. In a preferred embodiment a) comprises a pairwise deletion of the amino acids corresponding to H183*+G184* and b) comprises or consists of the substitution V379I of the polypeptide of SEQ ID NO: 1.

In another aspect, the variant comprises or consists of a substitution at a position corresponding to position 381. In another aspect, the amino acid at a position corresponding to position 381 is substituted with Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A381S of the polypeptide of SEQ ID NO: 1. In a preferred embodiment a) comprises a pairwise deletion of the amino acids corresponding to H183*+G184* and b) comprises or consists of the substitution A381S of the polypeptide of SEQ ID NO: 1.

In another aspect, the variant comprises or consists of a substitution at a position corresponding to position 382. In another aspect, the amino acid at a position corresponding to position 382 is substituted with Ala, Arg, Asn, Asp, Cys, Gln, Glu, Gly, His, lie, Leu, Lys, Phe, Pro, Ser, Thr, Trp, Tyr or Val. In another aspect, the variant comprises or consists of the substitution M382Y or M382L of the polypeptide of SEQ ID NO: 1. In a preferred embodiment a) comprises a pairwise deletion of the amino acids corresponding to H183*+G184* and b) comprises or consists of the substitution M382Y or M382L of the polypeptide of SEQ ID NO: 1.

In another aspect, the variant comprises or consists of a substitution at a position corresponding to position 383. In another aspect, the amino acid at a position corresponding to position 383 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R383K of the polypeptide of SEQ ID NO: 1. In a preferred embodiment a) comprises a pairwise deletion of the amino acids corresponding to H183*+G184* and b) comprises or consists of the substitution R383K of the polypeptide of SEQ ID NO: 1.

In another aspect, the variant comprises or consists of a substitution at a position corresponding to position 384. In another aspect, the amino acid at a position corresponding to position 384 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S384Q S384H of the polypeptide of SEQ ID NO: 1. In a preferred embodiment a) comprises a pairwise deletion of the amino acids corresponding to H183*+G184* and b) comprises or consists of the substitution S384Q S384H of the polypeptide of SEQ ID NO: 1.

In another aspect, the variant comprises or consists of a substitution at a position corresponding to position 385. In another aspect, the amino acid at a position corresponding to position 385 is substituted with Ala, Arg, Asn, Asp, Cys, Gln, Glu, Gly, His, lie, Leu, Met, Phe, Pro, Ser, Thr, Trp, Tyr or Val. In another aspect, the variant comprises or consists of the substitution K385Q of the polypeptide of SEQ ID NO: 1. In a preferred embodiment a) comprises a pairwise deletion of the amino acids corresponding to H183*+G184* and b) comprises or consists of the substitution K385Q of the polypeptide of SEQ ID NO: 1.

In another aspect, the variant comprises or consists of a substitution at a position corresponding to position 387. In another aspect, the amino acid at a position corresponding to position 387 is substituted with Ala, Arg, Asn, Cys, Gln, Glu, Gly, His, lie, Leu, Lys, Met, Phe, Pro, Ser, Thr, Trp, Tyr or Val. In another aspect, the variant comprises or consists of the substitution D387E or D387L of the polypeptide of SEQ ID NO: 1. In a preferred embodiment a) comprises a pairwise deletion of the amino acids corresponding to H183*+G184* and b) comprises or consists of the substitution D387E or D387L of the polypeptide of SEQ ID NO: 1.

In another aspect, the variant comprises or consists of a substitution at a position corresponding to position 389. In another aspect, the amino acid at a position corresponding to position 389 is substituted with Ala, Arg, Asn, Asp, Cys, Gln, Glu, Gly, His, Leu, Lys, Met, Phe, Pro, Ser, Thr, Trp, Tyr or Val. In another aspect, the variant comprises or consists of the substitution I389L of the polypeptide of SEQ ID NO: 1. In a preferred embodiment a) comprises a pairwise deletion of the amino acids corresponding to H183*+G184* and b) comprises or consists of the substitution I389L of the polypeptide of SEQ ID NO: 1.

In another aspect, the variant comprises or consists of a substitution at a position corresponding to position 391. In another aspect, the amino acid at a position corresponding to position 391 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution E391A or E391K of the polypeptide of SEQ ID NO: 1. In a preferred embodiment a) comprises a pairwise deletion of the amino acids corresponding to H183*+G184* and b) comprises or consists of the substitution E391A or E391K of the polypeptide of SEQ ID NO: 1.

In another aspect, the variant comprises or consists of a substitution at a position corresponding to position 394. In another aspect, the amino acid at a position corresponding to position 394 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution Q394K of the polypeptide of SEQ ID NO: 1. In a preferred embodiment a) comprises a pairwise deletion of the amino acids corresponding to H183*+G184* and b) comprises or consists of the substitution Q394K of the polypeptide of SEQ ID NO: 1.

In another aspect, the variant comprises or consists of a substitution at a position corresponding to position 395. In another aspect, the amino acid at a position corresponding to position 395 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution K395Q or K395D of the polypeptide of SEQ ID NO: 1. In a preferred embodiment a) comprises a pairwise deletion of the amino acids corresponding to H183*+G184* and b) comprises or consists of the substitution K395Q or K395D of the polypeptide of SEQ ID NO: 1.

In another aspect, the variant comprises or consists of a substitution at a position corresponding to position 400. In another aspect, the amino acid at a position corresponding to position 400 is substituted with Ala, Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution P400R or P400A or P400T of the polypeptide of SEQ ID NO: 1. In a preferred embodiment a) comprises a pairwise deletion of the amino acids corresponding to H183*+G184* and b) comprises or consists of the substitution P400R or P400A or P400T of the polypeptide of SEQ ID NO: 1.

In another aspect, the variant comprises or consists of a substitution at a position corresponding to position 402. In another aspect, the amino acid at a position corresponding to position 402 is substituted with Ala, Arg, Asn, Asp, Cys, Gln, Glu, Gly, lie, Leu, Lys, Met, Phe, Pro, Ser, Thr, Trp, Tyr or Val. In another aspect, the variant comprises or consists of the substitution H402R of the polypeptide of SEQ ID NO: 1. In a preferred embodiment a) comprises a pairwise deletion of the amino acids corresponding to H183*+G184* and b) comprises or consists of the substitution H402R of the polypeptide of SEQ ID NO: 1.

In another aspect, the variant comprises or consists of a substitution at a position corresponding to position 407. In another aspect, the amino acid at a position corresponding to position 407 is substituted with Ala, Arg, Asn, Asp, Cys, Gln, Glu, Gly, lie, Leu, Lys, Met, Phe, Pro, Ser, Thr, Trp, Tyr or Val. In another aspect, the variant comprises or consists of the substitution H407N of the polypeptide of SEQ ID NO: 1. In a preferred embodiment a) comprises a pairwise deletion of the amino acids corresponding to H183*+G184* and b) comprises or consists of the substitution H407N of the polypeptide of SEQ ID NO: 1.

In another aspect, the variant comprises or consists of a substitution at a position corresponding to position 408. In another aspect, the amino acid at a position corresponding to position 408 is substituted with Ala, Arg, Asn, Asp, Cys, Gln, Glu, Gly, His, lie, Leu, Lys, Met, Phe, Ser, Thr, Trp, Tyr or Val. In another aspect, the variant comprises or consists of the substitution P408H or P408Q of the polypeptide of SEQ ID NO: 1. In a preferred embodiment a) comprises a pairwise deletion of the amino acids corresponding to H183*+G184* and b) comprises or consists of the substitution P408H or P408Q of the polypeptide of SEQ ID NO: 1.

In another aspect, the variant comprises or consists of a substitution at a position corresponding to position 410. In another aspect, the amino acid at a position corresponding to position 410 is substituted with Ala, Arg, Asn, Asp, Cys, Gln, Glu, Gly, His, lie, Leu, Lys, Met, Phe, Pro, Ser, Thr, Trp or Tyr. In another aspect, the variant comprises or consists of the substitution V410I of the polypeptide of SEQ ID NO: 1. In a preferred embodiment a) comprises a pairwise deletion of the amino acids corresponding to H183*+G184* and b) comprises or consists of the substitution V410I of the polypeptide of SEQ ID NO: 1.

In another aspect, the variant comprises or consists of a substitution at a position corresponding to position 411. In another aspect, the amino acid at a position corresponding to position 411 is substituted with Ala, Arg, Asn, Asp, Cys, Gln, Glu, Gly, His, Leu, Lys, Met, Phe, Pro, Ser, Thr, Trp, Tyr or Val. In another aspect, the variant comprises or consists of the substitution 1411V of the polypeptide of SEQ ID NO: 1. In a preferred embodiment a) comprises a pairwise deletion of the amino acids corresponding to H183*+G184* and b) comprises or consists of the substitution 1411V of the polypeptide of SEQ ID NO: 1.

In another aspect, the variant comprises or consists of a substitution at a position corresponding to position 420. In another aspect, the amino acid at a position corresponding to position 420 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S420A or S420T of the polypeptide of SEQ ID NO: 1. In a preferred embodiment a) comprises a pairwise deletion of the amino acids corresponding to H183*+G184* and b) comprises or consists of the substitution S420A or S420T of the polypeptide of SEQ ID NO: 1.

In another aspect, the variant comprises or consists of a substitution at a position corresponding to position 423. In another aspect, the amino acid at a position corresponding to position 423 is substituted with Ala, Arg, Asn, Asp, Cys, Gln, Glu, Gly, His, lie, Leu, Met, Phe, Pro, Ser, Thr, Trp, Tyr or Val. In another aspect, the variant comprises or consists of the substitution K423N or K423G of the polypeptide of SEQ ID NO: 1. In a preferred embodiment a) comprises a pairwise deletion of the amino acids corresponding to H183*+G184* and b) comprises or consists of the substitution K423N or K423G of the polypeptide of SEQ ID NO: 1.

In another aspect, the variant comprises or consists of a substitution at a position corresponding to position 429. In another aspect, the amino acid at a position corresponding to position 429 is substituted with Ala, Arg, Asn, Asp, Cys, Gln, Glu, Gly, His, lie, Lys, Met, Phe, Pro, Ser, Thr, Trp, Tyr or Val. In another aspect, the variant comprises or consists of the substitution L429V of the polypeptide of SEQ ID NO: 1. In a preferred embodiment a) comprises a pairwise deletion of the amino acids corresponding to H183*+G184* and b) comprises or consists of the substitution L429V of the polypeptide of SEQ ID NO: 1.

In another aspect, the variant comprises or consists of a substitution at a position corresponding to position 430. In another aspect, the amino acid at a position corresponding to position 430 is substituted with Ala, Arg, Asn, Asp, Cys, Gln, Glu, Gly, His, Leu, Lys, Met, Phe, Pro, Ser, Thr, Trp, Tyr or Val. In another aspect, the variant comprises or consists of the substitution 1430M of the polypeptide of SEQ ID NO: 1. In a preferred embodiment a) comprises a pairwise deletion of the amino acids corresponding to H183*+G184* and b) comprises or consists of the substitution 1430M of the polypeptide of SEQ ID NO: 1.

In another aspect, the variant comprises or consists of a substitution at a position corresponding to position 431. In another aspect, the amino acid at a position corresponding to position 431 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T431S of the polypeptide of SEQ ID NO: 1. In a preferred embodiment a) comprises a pairwise deletion of the amino acids corresponding to H183*+G184* and b) comprises or consists of the substitution T431S of the polypeptide of SEQ ID NO: 1.

In another aspect, the variant comprises or consists of a substitution at a position corresponding to position 437. In another aspect, the amino acid at a position corresponding to position 437 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S437A of the polypeptide of SEQ ID NO: 1. In a preferred embodiment a) comprises a pairwise deletion of the amino acids corresponding to H183*+G184* and b) comprises or consists of the substitution S437A of the polypeptide of SEQ ID NO: 1.

In another aspect, the variant comprises or consists of a substitution at a position corresponding to position 439. In another aspect, the amino acid at a position corresponding to position 439 is substituted with Ala, Asn, Asp, Cys, Gln, Glu, Gly, His, lie, Leu, Lys, Met, Phe, Pro, Ser, Thr, Trp, Tyr or Val. In another aspect, the variant comprises or consists of the substitution R439T of the polypeptide of SEQ ID NO: 1. In a preferred embodiment a) comprises a pairwise deletion of the amino acids corresponding to H183*+G184* and b) comprises or consists of the substitution R439T of the polypeptide of SEQ ID NO: 1.

In another aspect, the variant comprises or consists of a substitution at a position corresponding to position 442. In another aspect, the amino acid at a position corresponding to position 442 is substituted with Arg, Asn, Asp, Cys, Gln, Glu, Gly, His, lie, Leu, Lys, Met, Phe, Pro, Ser, Thr, Trp, Tyr or Val. In another aspect, the variant comprises or consists of the substitution A442V of the polypeptide of SEQ ID NO: 1. In a preferred embodiment a) comprises a pairwise deletion of the amino acids corresponding to H183*+G184* and b) comprises or consists of the substitution A442V of the polypeptide of SEQ ID NO: 1.

In another aspect, the variant comprises or consists of a substitution at a position corresponding to position 444. In another aspect, the amino acid at a position corresponding to position 444 is substituted with Ala, Arg, Asn, Asp, Cys, Gln, Glu, Gly, His, lie, Lys, Met, Phe, Pro, Ser, Thr, Trp, Tyr or Val. In another aspect, the variant comprises or consists of the substitution L444A or L444T or L444R of the polypeptide of SEQ ID NO: 1. In a preferred embodiment a) comprises a pairwise deletion of the amino acids corresponding to H183*+G184* and b) comprises or consists of the substitution L444A or L444T or L444R of the polypeptide of SEQ ID NO: 1.

In another aspect, the variant comprises or consists of a substitution at a position corresponding to position 445. In another aspect, the amino acid at a position corresponding to position 445 is substituted with Ala, Arg, Asn, Asp, Cys, Gln, Glu, Gly, His, lie, Leu, Met, Phe, Pro, Ser, Thr, Trp, Tyr or Val. In another aspect, the variant comprises or consists of the substitution K445Q or K445S or K445A of the polypeptide of SEQ ID NO: 1. In a preferred embodiment a) comprises a pairwise deletion of the amino acids corresponding to H183*+G184* and b) comprises or consists of the substitution K445Q or K445S or K445A of the polypeptide of SEQ ID NO: 1.

In another aspect, the variant comprises or consists of a substitution at a position corresponding to position 446. In another aspect, the amino acid at a position corresponding to position 446 is substituted with Ala, Arg, Asp, Cys, Gln, Glu, Gly, His, lie, Leu, Lys, Met, Phe, Pro, Ser, Thr, Trp, Tyr or Val. In another aspect, the variant comprises or consists of the substitution N446H of the polypeptide of SEQ ID NO: 1. In a preferred embodiment a) comprises a pairwise deletion of the amino acids corresponding to H183*+G184* and b) comprises or consists of the substitution N446H of the polypeptide of SEQ ID NO: 1.

In another aspect, the variant comprises or consists of a substitution at a position corresponding to position 449. In another aspect, the amino acid at a position corresponding to position 449 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E449Q of the polypeptide of SEQ ID NO: 1. In a preferred embodiment a) comprises a pairwise deletion of the amino acids corresponding to H183*+G184* and b) comprises or consists of the substitution E449Q of the polypeptide of SEQ ID NO: 1.

In another aspect, the variant comprises or consists of a substitution at a position corresponding to position 450. In another aspect, the amino acid at a position corresponding to position 450 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T450V or T450I of the polypeptide of SEQ ID NO: 1. In a preferred embodiment a) comprises a pairwise deletion of the amino acids corresponding to H183*+G184* and b) comprises or consists of the substitution T450V or T450I of the polypeptide of SEQ ID NO: 1.

In another aspect, the variant comprises or consists of a substitution at a position corresponding to position 451. In another aspect, the amino acid at a position corresponding to position 451 is substituted with Ala, Arg, Asn, Asp, Cys, Gln, Glu, Gly, His, lie, Leu, Lys, Met, Phe, Pro, Ser, Thr, Tyr or Val. In another aspect, the variant comprises or consists of the substitution W451 F of the polypeptide of SEQ ID NO: 1. In a preferred embodiment a) comprises a pairwise deletion of the amino acids corresponding to H183*+G184* and b) comprises or consists of the substitution W451F of the polypeptide of SEQ ID NO: 1.

In another aspect, the variant comprises or consists of a substitution at a position corresponding to position 452. In another aspect, the amino acid at a position corresponding to position 452 is substituted with Ala, Arg, Asn, Asp, Cys, Gln, Glu, Gly, His, lie, Leu, Lys, Met, Phe, Pro, Ser, Thr, Trp or Val. In another aspect, the variant comprises or consists of the substitution Y452K or Y452H of the polypeptide of SEQ ID NO: 1. In a preferred embodiment a) comprises a pairwise deletion of the amino acids corresponding to H183*+G184* and b) comprises or consists of the substitution Y452K or Y452H of the polypeptide of SEQ ID NO: 1.

In another aspect, the variant comprises or consists of a substitution at a position corresponding to position 454. In another aspect, the amino acid at a position corresponding to position 454 is substituted with Ala, Arg, Asn, Asp, Cys, Gln, Glu, Gly, His, Leu, Lys, Met, Phe, Pro, Ser, Thr, Trp, Tyr or Val. In another aspect, the variant comprises or consists of the substitution I454L of the polypeptide of SEQ ID NO: 1. In a preferred embodiment a) comprises a pairwise deletion of the amino acids corresponding to H183*+G184* and b) comprises or consists of the substitution I454L of the polypeptide of SEQ ID NO: 1.

In another aspect, the variant comprises or consists of a substitution at a position corresponding to position 459. In another aspect, the amino acid at a position corresponding to position 459 is substituted with Ala, Arg, Asn, Asp, Cys, Gln, Glu, Gly, His, lie, Leu, Lys, Met, Phe, Pro, Thr, Trp, Tyr or Val. In another aspect, the variant comprises or consists of the substitution S459T of the polypeptide of SEQ ID NO: 1. In a preferred embodiment a) comprises a pairwise deletion of the amino acids corresponding to H183*+G184* and b) comprises or consists of the substitution S459T of the polypeptide of SEQ ID NO: 1.

In another aspect, the variant comprises or consists of a substitution at a position corresponding to position 460. In another aspect, the amino acid at a position corresponding to position 460 is substituted with Ala, Arg, Asn, Cys, Gln, Glu, Gly, His, lie, Leu, Lys, Met, Phe, Pro, Ser, Thr, Trp, Tyr or Val. In another aspect, the variant comprises or consists of the substitution D460E of the polypeptide of SEQ ID NO: 1. In a preferred embodiment a) comprises a pairwise deletion of the amino acids corresponding to H183*+G184* and b) comprises or consists of the substitution D460E of the polypeptide of SEQ ID NO: 1.

In another aspect, the variant comprises or consists of a substitution at a position corresponding to position 461. In another aspect, the amino acid at a position corresponding to position 461 is substituted with Ala, Arg, Asn, Asp, Cys, Gln, Glu, Gly, His, lie, Leu, Lys, Met, Phe, Pro, Ser, Trp, Tyr or Val. In another aspect, the variant comprises or consists of the substitution T461P or T461K of the polypeptide of SEQ ID NO: 1. In a preferred embodiment a) comprises a pairwise deletion of the amino acids corresponding to H183*+G184* and b) comprises or consists of the substitution T461P or T461K of the polypeptide of SEQ ID NO: 1.

In another aspect, the variant comprises or consists of a substitution at a position corresponding to position 462. In another aspect, the amino acid at a position corresponding to position 462 is substituted with Ala, Arg, Asn, Asp, Cys, Gln, Glu, Gly, His, lie, Leu, Lys, Met, Phe, Pro, Ser, Thr, Trp, or Tyr. In another aspect, the variant comprises or consists of the substitution V462I of the polypeptide of SEQ ID NO: 1. In a preferred embodiment a) comprises a pairwise deletion of the amino acids corresponding to H183*+G184* and b) comprises or consists of the substitution V462I of the polypeptide of SEQ ID NO: 1.

In another aspect, the variant comprises or consists of a substitution at a position corresponding to position 463. In another aspect, the amino acid at a position corresponding to position 463 is substituted with Ala, Arg, Asn, Asp, Cys, Gln, Glu, Gly, His, lie, Leu, Met, Phe, Pro, Ser, Thr, Trp, Tyr or Val. In another aspect, the variant comprises or consists of the substitution K463T or K463V of the polypeptide of SEQ ID NO: 1. In a preferred embodiment a) comprises a pairwise deletion of the amino acids corresponding to H183*+G184* and b) comprises or consists of the substitution K463T or K463V of the polypeptide of SEQ ID NO: 1.

In another aspect, the variant comprises or consists of a substitution at a position corresponding to position 465. In another aspect, the amino acid at a position corresponding to position 465 is substituted with Ala, Arg, Asn, Asp, Cys, Gln, Glu, His, lie, Leu, Lys, Met, Phe, Pro, Ser, Thr, Trp, Tyr or Val. In another aspect, the variant comprises or consists of the substitution G465N of the polypeptide of SEQ ID NO: 1. In a preferred embodiment a) comprises a pairwise deletion of the amino acids corresponding to H183*+G184* and b) comprises or consists of the substitution G465N of the polypeptide of SEQ ID NO: 1.

In another aspect, the variant comprises or consists of a substitution at a position corresponding to position 467. In another aspect, the amino acid at a position corresponding to position 467 is substituted with Ala, Arg, Asn, Cys, Gln, Glu, Gly, His, lie, Leu, Lys, Met, Phe, Pro, Ser, Thr, Trp, Tyr or Val. In another aspect, the variant comprises or consists of the substitution D467A or D467E of the polypeptide of SEQ ID NO: 1. In a preferred embodiment a) comprises a pairwise deletion of the amino acids corresponding to H183*+G184* and b) comprises or consists of the substitution D467A or D467E of the polypeptide of SEQ ID NO: 1.

In another aspect, the variant comprises or consists of a substitution at a position corresponding to position 469. In another aspect, the amino acid at a position corresponding to position 469 is substituted with Ala, Arg, Asn, Asp, Cys, Gln, Glu, Gly, His, lie, Leu, Lys, Met, Phe, Pro, Ser, Thr, Trp, or Val. In another aspect, the variant comprises or consists of the substitution W469Y or W469N or W469T of the polypeptide of SEQ ID NO: 1. In a preferred embodiment a) comprises a pairwise deletion of the amino acids corresponding to H183*+G184* and b) comprises or consists of the substitution W469Y or W469N or W469T of the polypeptide of SEQ ID NO: 1.

In another aspect, the variant comprises or consists of a substitution at a position corresponding to position 470. In another aspect, the amino acid at a position corresponding to position 470 is substituted with Ala, Arg, Asn, Asp, Cys, Gln, Glu, His, lie, Leu, Lys, Met, Phe, Pro, Ser, Thr, Trp, Tyr or Val. In another aspect, the variant comprises or consists of the substitution G470A of the polypeptide of SEQ ID NO: 1. In a preferred embodiment a) comprises a pairwise deletion of the amino acids corresponding to H183*+G184* and b) comprises or consists of the substitution G470A of the polypeptide of SEQ ID NO: 1.

In another aspect, the variant comprises or consists of a substitution at a position corresponding to position 471. In another aspect, the amino acid at a position corresponding to position 471 is substituted with Ala, Arg, Asn, Asp, Cys, Gln, Gly, His, lie, Leu, Lys, Met, Phe, Pro, Ser, Thr, Trp, Tyr or Val. In another aspect, the variant comprises or consists of the substitution E471T of the polypeptide of SEQ ID NO: 1. In a preferred embodiment a) comprises a pairwise deletion of the amino acids corresponding to H183*+G184* and b) comprises or consists of the substitution E471T of the polypeptide of SEQ ID NO: 1.

In another aspect, the variant comprises or consists of a substitution at a position corresponding to position 473. In another aspect, the amino acid at a position corresponding to position 473 is substituted with Ala, Arg, Asn, Asp, Cys, Gln, Glu, Gly, lie, Leu, Lys, Met, Phe, Pro, Ser, Thr, Trp, Tyr or Val. In another aspect, the variant comprises or consists of the substitution H473P or H473R of the polypeptide of SEQ ID NO: 1. In a preferred embodiment a) comprises a pairwise deletion of the amino acids corresponding to H183*+G184* and b) comprises or consists of the substitution H473P or H473R of the polypeptide of SEQ ID NO: 1.

In another aspect, the variant comprises or consists of a substitution at a position corresponding to position 474. In another aspect, the amino acid at a position corresponding to position 474 is substituted with Ala, Arg, Asn, Asp, Cys, Gln, Glu, Gly, His, lie, Leu, Lys, Met, Phe, Pro, Ser, Thr, Trp, or Tyr. In another aspect, the variant comprises or consists of the substitution V474C of the polypeptide of SEQ ID NO: 1. In a preferred embodiment a) comprises a pairwise deletion of the amino acids corresponding to H183*+G184* and b) comprises or consists of the substitution V474C of the polypeptide of SEQ ID NO: 1.

In another aspect, the variant comprises or consists of a substitution at a position corresponding to position 476. In another aspect, the amino acid at a position corresponding to position 476 is substituted with Ala, Arg, Asn, Cys, Gln, Glu, Gly, His, lie, Leu, Lys, Met, Phe, Pro, Ser, Thr, Trp, Tyr or Val. In another aspect, the variant comprises or consists of the substitution D476K of the polypeptide of SEQ ID NO: 1. In a preferred embodiment a) comprises a pairwise deletion of the amino acids corresponding to H183*+G184* and b) comprises or consists of the substitution D476K of the polypeptide of SEQ ID NO: 1.

In another aspect, the variant comprises or consists of a substitution at a position corresponding to position 477. In another aspect, the amino acid at a position corresponding to position 477 is substituted with Ala, Arg, Asn, Asp, Cys, Gln, Glu, His, lie, Leu, Lys, Met, Phe, Pro, Ser, Thr, Trp, Tyr, or Val. In another aspect, the variant comprises or consists of the substitution G477E of the polypeptide of SEQ ID NO: 1. In a preferred embodiment a) comprises a pairwise deletion of the amino acids corresponding to H183*+G184* and b) comprises or consists of the substitution G477E of the polypeptide of SEQ ID NO: 1.

In another aspect, the variant comprises or consists of a substitution at a position corresponding to position 481. In another aspect, the amino acid at a position corresponding to position 481 is substituted with Ala, Arg, Asn, Asp, Cys, Gln, Glu, Gly, His, Leu, Lys, Met, Phe, Pro, Ser, Thr, Trp, Tyr, or Val. In another aspect, the variant comprises or consists of the substitution I481V of the polypeptide of SEQ ID NO: 1. In a preferred embodiment a) comprises a pairwise deletion of the amino acids corresponding to H183*+G184* and b) comprises or consists of the substitution I481V of the polypeptide of SEQ ID NO: 1.

In another aspect, the variant comprises or consists of a substitution at a position corresponding to position 482. In another aspect, the amino acid at a position corresponding to position 482 is substituted with Ala, Arg, Asn, Asp, Cys, Gln, Glu, Gly, His, lie, Leu, Lys, Met, Phe, Pro, Ser, Thr, Trp, or Val. In another aspect, the variant comprises or consists of the substitution Y482W of the polypeptide of SEQ ID NO: 1. In a preferred embodiment a) comprises a pairwise deletion of the amino acids corresponding to H183*+G184* and b) comprises or consists of the substitution Y482W of the polypeptide of SEQ ID NO: 1.

In another aspect, the variant comprises or consists of a substitution at a position corresponding to position 484. In another aspect, the amino acid at a position corresponding to position 484 is substituted with Ala, Arg, Asn, Asp, Cys, Glu, Gly, His, lie, Leu, Lys, Met, Phe, Pro, Ser, Thr, Trp, Tyr, or Val. In another aspect, the variant comprises or consists of the substitution Q484K of the polypeptide of SEQ ID NO: 1. In a preferred embodiment a) comprises a pairwise deletion of the amino acids corresponding to H183*+G184* and b) comprises or consists of the substitution Q484K of the polypeptide of SEQ ID NO: 1.

In another aspect, the variant comprises or consists of a substitution at a position corresponding to position 485. In another aspect, the amino acid at a position corresponding to position 485 is substituted with Ala, Arg, Asn, Asp, Cys, Gln, Glu, Gly, His, lie, Leu, Met, Phe, Pro, Ser, Thr, Trp, Tyr, or Val. In another aspect, the variant comprises or consists of the substitution K485R or K485Q of the polypeptide of SEQ ID NO: 1. In a preferred embodiment a) comprises a pairwise deletion of the amino acids corresponding to H183*+G184* and b) comprises or consists of the substitution K485R or K485Q of the polypeptide of SEQ ID NO: 1.

In one aspect, the variant comprises a) a pairwise deletion of the amino acids corresponding to positions H183*+G184* and b) alteration at one or more of following position corresponding to positions: H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311, 1312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, I389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

In one aspect, the variant comprises a) a pairwise deletion of the amino acids corresponding to positions H183*+

G184* and b) alteration at one or more of following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the polypeptide of SEQ ID NOs: 1, 2, 3, 4 5, 6, 7, 8, 9, 10, 11, 12 or 13.

The variants have at least 20%, e.g., at least 40%, at least 50%, at least 60%, at least 70%, at least 80%, at least 90%, at least 95%, or at least 100% of the alpha-amylase activity of the polypeptide of SEQ ID NOs: 1, 2, 3, 4 5, 6, 7, 8, 9, 10, 11, 12 or 13.

In an embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6% but less than 100% to the amino acid sequence of the parent alpha-amylase having alpha-amylase activity.

In another embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 1.

In another embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 2.

In another embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 3.

In another embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 4.

In another embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 5.

In another embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 6.

In another embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 7.

In another embodiment, the variant has sequence identity of at least at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 8.

In another embodiment, the variant has sequence identity of at least at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 9.

In another embodiment, the variant has sequence identity of at least at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 10.

In another embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 11.

In another embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 12.

In another embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 13.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 1.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 2.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 3.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 4.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 5.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 6.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 7.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 8.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 9.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 10.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 11.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, 1411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 12.

In one aspect, the variant comprises a) a pairwise deletion of the amino acids corresponding to positions H183*+G184* and b) alteration at one or more of the following position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to polypeptide of SEQ ID NO: 13.

In one aspect, the variant comprises a) a pairwise deletion of the amino acids corresponding to positions H183*+G184* and b) at least one alteration at a position corresponding to positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T1 32S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: A51T+N54A+G109A+R118T+E134D+W140Y+R172S+H183*+G184*+E190P+I206L+Y243F+F267Y+Q280N+K281 F+N299A+K302N+R320K+S334T+A339S+V410I+E471T+D476K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471T+D476K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: N174S+H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471T+D476K; N174S+H183*+G184*+N311K+I312L+F313L+Q319S+R320K+H324K+S334T+E345Q+E346P+L355F+T356I+Q361 S+Y371M+R383K+S384H+D387E+E391K+Q394K+K395Q+P400A+V410I+E471T+D476K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: K35A+A51T+N54A+G109A+R118T+W140Y+R172S+N174*+R181Q+H183*+G184*+E190P+I206L+I235L+Y243F+F267Y+Q280N+K281F+N299A+K302T+R320K+S334T+A339S+E345Q+E346P+V410I, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: T5L+N33Y+K35A+S36E+K37H+N95R+G109A+H183*+G184*+E190P+Q280N+W284F+N296Q+L297F+N311K+I312L+F313L+Q319S+R320K+H324K+S334T+L355F+T356I+Q361S+Y371M+R383K+S384H+D387E+E391K+Q394K+K395Q+P400A; M105I+G109A+V131I+Y135H+Q169E+N174*+H183*+G184*+I206Y+M208Y+L217I+I235L+T246L+I250V+A263T+F343T+E346T+I374T+V379I+M382L+V410I+K423N+S437A+A442V+L444A+Y452H+D460E+T461P+K463V+G465N+D467E+K485R; R118N+N174S+H183*+G184*+E190P+I206L+Y243F+F267Y+K281F+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471T+D476K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: N22Q+N25R+N28Q+S29N+A51T+N54A+N70H+R82K+S83G+Q84E+V89I+T90K+K93H+Q98N+M116D+R118T+E130V+T136L+E138K+R142H+D144H+

N150S+H152Y+S154D+R158Y+R181Q+H183*+G184*+E190P+T225A+T227E+G229Q+T356I+Q361S, using SEQ ID NO: 1 for numbering, and wherein said variant at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: H1A+N3A+M9L+K35A+W48Y+A51T+N54A+M105I+G109A+R118T+W140Y+R172S+N174*+R181Q+H183*+G184*+E190P+I206L+I235L+Y243F+T246L+F267Y+Q280N+K281F+N299A+K302T+R320K+S334T+A339S+E345Q+E346P+V379I+M382L+V410I+D476K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: N22Q+N25K+N28Q+S29N+A51T+N54A+N70H+Q84D+V89I+T90K+K93H+Q98N+M116D+R118Q+E130V+V131I+T136L+E138K+N174*+R181Q+H183*+G184*+I206L+G229Q+Q319S+R320K+F343T+E346T+I374T+V379I+M382L+R383K+P400A+K423N+L444A+K463V; H1A+N3A+A51T+N54A+G109A+R118T+E134D+W140Y+R172S+N174S+H183*+G184*+E190P+I206L+Y243F+F267Y+Q280N+K281F+N299A+K302N+R320K+S334T+A339S+V410I+I411V+K423N+S437A+A442V+L444R+K445Q+Y452H+D460E+T461P+K463V+G465N+D467E+D476K+K485R; H1*+N3A+A51T+N54A+G109A+R118T+E134D+W140Y+R172S+N174S+H183*+G184*+E190P+I206L+Y243F+F267Y+Q280N+K281 F+N299A+K302N+R320K+S334T+A339S+V410I+I411V+K423N+S437A+A442V+L444R+K445Q+Y452H+D460E+T461P+K463V+G465N+D467E+D476K+K485R, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: N174S+H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+P408H+V410I+I411V+K423N+S437A+A442V+L444R+K445Q+Y452H+D460E+T461P+K463V+G465N+D467E+D476K+K485R; H1*+N3A+M9L+K35A+W48Y+A51T+N54A+M105I+G109A+R118T+W140Y+R172S+N174*+R181Q+H183*+G184*+E190P+I206L+I235L+Y243F+T246L+F267Y+Q280N+K281F+N299A+K302T+R320K+S334T+A339S+E345Q+E346P+T356I+Q361S+V379I+M382L+V410I+D476K; H1*+N3A+M9L+K35A+W48Y+A51T+N54A+M105I+G109A+R118Q+W140Y+R172S+N174*+R181Q+H183*+G184*+E190P+I206L+V214I+I235L+Y243F+T246L+F267Y+Q280N+K281F+N299A+K302T+R320K+S334T+A339S+E345Q+E346P+V379I+M382L+V410I+D476K+K485R, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: A51T+N54A+Q98N+G109A+M116D+R118Q+E130V+T136L+E138K+R142H+D144H+S154D+R158Y+N174*+R181Q+H183*+G184*+E190P+I206L+E212D+V214A+R218K+N219R+V222T+T225A+S255E+A256K+W284F+N311K+R320K+H324K+S334T+T356I+Q361S+V410I+R439T+W469N+E471T; N174S+H183*+G184*+N311K+I312L+F313L+Q319S+R320K+H324K+S334T+E345Q+E346P+L355F+T356I+Q361S+Y371M+V379I+R383K+S384H+D387E+E391K+Q394K+K395Q+P400A+P408H+V410I+I411V+K423N+S437A+A442V+L444R+K445Q+Y452H+D460E+T461P+K463V+G465N+D467E+D476K+K485R, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: H1A+N3A+K35A+A51T+N54A+G109A+R118T+W140Y+R172S+N174S+R181Q+H183*+G184*+E190P+I206L+I235L+Y243F+F267Y+Q280N+K281F+N299A+K302T+R320K+S334T+A339S+E345Q+E346P+P408H+V410I+I411V+K423N+S437A+A442V+L444R+K445Q+Y452H+D460E+T461P+K463V+G465N+D467E+D476K+K485R, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: A51T+N54A+Q98N+G109A+M116D+

R118Q+E130V+T136L+E138K+W140Y+R142H+D144H+S154D+R158Y+N174*+R181Q+H183*+G184*+E190P+I206L+E212D+V214A+R218K+N219R+V222T+T225A+S255E+A256K+Q280N+W284F+K302N+N311K+R320K+H324K+S334T+T356I+Q361S+V410I+R439T+W469N+E471T+D476K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: H1*+N3A+K35A+A51T+N54A+G109A+R118T+W140Y+R172S+N174S+R181Q+H183*+G184*+E190P+I206L+I235L+Y243F+F267Y+Q280N+K281F+N299A+K302T+R320K+S334T+A339S+E345Q+E346P+T356I+Q361S+P408H+V410I+I411V+K423N+S437A+A442V+L444R+K445Q+Y452H+D460E+T461P+K463V+G465N+D467E+D476K+K485R; H1*+N3A+K35A+A51T+N54A+G109A+R118T+W140Y+R172S+N174S+R181Q+H183*+G184*+E190P+I206L+I235L+Y243F+F267Y+Q280N+K281 F+N299A+K302T+R320K+S334T+A339S+E345Q+E346P+T356I+Q361S+P408H+V410I+I411V+K423N+S437A+A442V+L444R+K445Q+Y452H+D460E+T461P+K463V+G465N+D467E+D476K+K485R; R118Q+N174S+H183*+G184*+E190P+I206L+Y243F+F267Y+K281F+N311K+I312L+F313L+Q319S+R320K+H324K+S334T+E345Q+E346P+L355F+T356I+Q361S+Y371M+R383K+S384H+D387E+E391K+Q394K+K395Q+P400A+P408H+V410I+I411V+K423N+S437A+A442V+L444R+K445Q+Y452H+D460E+T461P+K463V+G465N+D467E+D476K+K485R, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: K35A+A51T+N54A+D62N+M105I+G109A+R118T+V131I+Y135H+W140Y+Q169E+R172S+N174*+H183*+G184*+E190P+I206L+M208Y+L217I+I235L+Y243F+T246L+I250V+A263T+F267Y+Q280N+K281F+N299A+K302T+F343T+E346T+I374T+V379I+M382L+V410I+K423N+S437A+A442V+L444A+Y452H+D460E+T461P+K463V+G465N+D467E+E471T+D476K+K485R, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or13.

In one aspect, a variant comprises substitutions at positions corresponding to positions selected from a group consisting of: H1A+N3A+G4N+T5L+M9L+L17M+N22Q+N25R+N28Q+S29N+A31S+S32A+N33Y+K35A+S36E+K37H+W48Y+A51T+N54A+M105I+G109A+R118T+E134D+W140Y+R172S+N174S+H183*+G184*+E190P+I206L+Y243F+F267Y+Q280N+W284F+N299A+K302N+Q319S+R320K+S323L+H324K+A325S+S334T+A339S+V379I+M382L+V410I+E471T+D476K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: N22Q+N25R+N28Q+S29N+A51T+N54A+N70H+R82K+S83G+Q84E+V89I+T90K+K93H+Q98N+G109A+M116D+R118T+E130V+T136L+E138K+W140Y+R142H+D144H+N150S+H152Y+S154D+R158Y+R172S+N174*+R181Q+H183*+G184*+E190P+I206L+Y243F+F267Y+Q280N+K281F+N299A+K302N+R320K+S334T+A339S+E345Q+E346P+T356I+Q361S+V410I+E471T+D476K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: H1*+N3D+M9L+K35A+W48Y+A51T+N54S+R82K+V89I+M105I+G109A+R118N+W140Y+H152Y+V165T+R172S+N174*+R181Q+H183*+G184*+E190P+I206Y+M208Y+E212D+V214I+L217I+T227E+I235L+Y243F+T246L+N260G+F267Y+I275L+Q280T+K281Y+N299A+K302T+R320K+A325S+S334T+A339S+F343T+E345Q+E346P+T356I+V379I+M382L+R383K+V410I+I430M+D476K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: N22Q+N25K+N28Q+S29N+K35A+A51T+N54A+N70H+Q84D+V891+T90K+K93H+Q98N+G109A+M116D+R118Q+E130V+V131I+T136L+E138K+

W167F+R172S+R181Q+H183*+G184*+I206L+G229Q+I235L+Y243F+F267Y+Q280N+K281 F+N299A+K302N+Q319S+R320K+S334T+A339S+F343T+E345Q+E346T+I374T+V379I+M382L+R383K+P400A+V410I+K423N+L444A+K463V+E471T+D476K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: H1*+N28R+S36D+T40S+A51T+N54A+V75I+S83N+T90N+S91A+N94S+G109A+R118N+T132S+E134D+W140Y+R142K+S154N+R172S+H183*+G184*+A186G+E190P+N195F+I206L+Y243F+F267Y+Q280N+K281F+N299S+K302N+N311Q+R320K+S323M+S334T+A339S+T356I+Q361S+R383K+P400R+P408H+V410I+I411V+K423N+S437A+A442V+L444R+K445Q+Y452H+D460E+T461P+K463V+G465N+D467E+E471T+D476K+K485R, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: H1*+N3D+T5L+M9I+Y16N+L17V+N22Q+N25R+N28Q+S29N+D30N+S32Q+N33Y+K35A+S36E+K37H+V42I+A51T+N54A+V56T+N70H+R82K+S83G+Q84E+Q86E+A87R+V89I+T90K+K93H+N94A+N95R+Q98N+G109A+A113Q+M116D+R118N+N125Q+E130V+T132S+E134T+T136L+E138K+W140Y+R142H+D144H+N150S+T151Q+H152Y+S154D+R158Y+V165T+R172S+N174*+R181Q+H183*+G184*+G184T+E190P+N195F+I206L+V214I+R218N+N219R+T225A+T227E+G229Q+I235L+Y243F+T246M+I250L+N251 G+S255G+A256Q+M261 L+F267Y+I275L+Q280N+K281 F+N285T+H286M+V288A+N299S+K302N+G304S+I312L+F313L+V317L+R320K+S334T+E337G+A339S+E345Q+E346P+L355T+T356I+Q361S+T376S+H377D+A381S+M382Y+S384Q+K385Q+I389L+E391A+K395Q+P400A+H407N+P408Q+V410I+S420A+K423G+L429V+I430M+T431S+R439T+A442V+L444T+K445A+N446H+E449Q+T450V+W451 F+Y452K+D460E+T461P+K463V+G465N+D467A+W469T+E471T+H473R+V474C+D476K+Y482W+Q484K+K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: H1A+H2*+N3A+M9L+K35A+W48Y+A51T+N54A+M105I+G109A+R118T+W140Y+R172S+R181Q+E188P+I204L+I233L+Y241F+T244L+F265Y+Q278N+K279F+N297A+K300T+R318K+S332T+A337S+E343Q+E344P+V377I+M380L+V408I+D474K, H1*+H2*+N3A+M9L+K35A+W48Y+A51T+N54A+M105I+G109A+R118Q+W140Y+R172S+R181Q+E188P+I204L+V212I+I233L+Y241F+T244L+F265Y+Q278N+K279F+N297A+K300T+R318K+S332T+A337S+E343Q+E344P+V377I+M380L+V408I+D474K, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: H1*+N3D+T5L+M9I+Y16N+L17V+N22Q+N25R+N28Q+S29N+D30N+S32Q+N33Y+K35A+S36E+K37H+V42I+A51T+N54A+V56T+N70H+R82K+S83G+Q84E+Q86E+A87R+V89I+T90K+K93H+N94A+N95R+Q98N+G109A+A113Q+M116D+R118N+N125Q+E130V+T132S+E134T+T136L+E138K+W140Y+R142H+D144H+N150S+T151Q+H152Y+S154D+R158Y+V165T+R172S+N174*+R181Q+G182T+H183*+G184*+E190P+N195F+I206L+V214I+R218N+N219R+T225A+T227E+G229Q+I235L+Y243F+T246M+I250L+N251 G+S255G+A256Q+M261 L+F267Y+I275L+Q280N+K281 F+N285T+H286M+V288A+N299S+K302N+G304S+I312L+F313L+V317L+R320K+S334T+E337G+A339S+E345Q+E346P+L355T+T356I+Q361S+Y371M+I374T+P375S+T376Q+H377R+G378E+A381S+M382Y+S384Q+K385Q+I389L+E391A+K395Q+P400A+H407N+P408Q+V410I+S420A+K423G+L429V+I430M+T431S+R439T+A442V+L444T+K445A+N446H+E449Q+T450V+W451F+Y452K+S459T+K463T+G465N+D467A+W469T+E471T+H473R+V474C+D476K+Y482W+Q484K+K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

In one aspect, a variant comprises substitutions at positions corresponding to positions selected from a group consisting of: H1*+H2*+N3A+G4A+L17V+N22Q+H23Q+N28R+S29T+S32P+N33Y+K35S+K37V+T40N+I44T+W48Y+A51T+N54A+A60P+R82K+S83G+Q84E+Q86K+A87S+T90N+S91T+K93H+N94S+G109A+A113Y+M116N+R118T+N125S+N128Y+V131I+T132S+T136N+E138Q+R142G+D144N+N150T+H152Y+S154N+F155W+R158Q+Y160F+V165T+R172S+N174*+N175S+Y178F+R181D+H183*+G184*+E190P+D192S+T193S+I206Y+M208Y+E212D+L217M+R218K+N219K+

T225A+T227E+L228V+F233Y+I235L+Y243F+T246L+R247K+I250V+N251 D+H252N+V253A+S255A+N260E+A263T+A265G+F267Y+K269Q+I275L+E276N+Q280A+T282V+W284Y+H286Q+V288L+V291A+L297F+N299A+K302T+S303G+N306Y+F313L+G315N+V317L+Q319A+R320S+H321N+S323T+H324K+F328L+D330E+S334T+E337G+E338Q+A339S+F343T+E345Q+E346P+W347R+L355F+T356I+E360S+Q361G+Y371M+*372aG+*372bT+*372cK+I374T+P375T+H377R+G378E+V379I+M382L+R383K+D387E+I389L+E391K+Q394K+K395D+P400T+H402R+H407N+S420T+L429V+A442V+L444T+K445S+T450I+I454L+S459T+T461K+V462I+K463T+W469Y+G470A+E471T+H473P+D476K+G477E+I481V+Y482W+K485Q, using SEQ ID NO: 1 for numbering, and wherein said variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NOs: 1, 2, 3, 4 5, 6, 7, 8, 9, 10, 11, 12 or 13.

The inventors of the present invention have identified that these specific alterations at these positions of the amino acid sequence as set forth in SEQ ID NO: 1 or 2, are particularly relevant for improving the performance of a variant alpha-amylase having at least 60% sequence identity to the parent polypeptide.

According to the present invention, a value of 1.0 corresponds to the performance observed for the parent polypeptide. A value above 1.0 indicates an improvement of performance of the variant tested compared to the parent polypeptide. Accordingly, any value of >1.0 is indicative for improvement of property, such as performance, of the variant compared to the parent polypeptide.

According to the present invention, a variant showing improvement of property under at least one condition tested, is considered a variant having improved property as compared to the parent polypeptide.

As stated elsewhere herein, the parent polypeptide may be any polypeptide having alpha-amylase activity and at least 60% sequence identity to any one of the amino acid sequences as set forth in SEQ ID NO: 1 or SEQ ID NO: 2.

As can be seen from the data obtained in Examples, all tested variants have an Improvement Factor (IF) of at least 1.1, i.e. above the parent alpha-amylase has amino acid sequence as shown in SEQ ID NO: 1 and/or SEQ ID NO: 2.

In one embodiment, the variant has an improved wash performance, the enhanced wash performance corresponding to an Improvement Factor (IF) of at least 1.1, preferably at least 1.2, at least 1.3, at least 1.4, at least 1.5, at least 1.6, at least 1.7, at least 1.8, at least 1.9, at least 2.0, at least 2.2, at least 2.4, at least 2.6, at least 2.8, at least 3.0, at least 3.2, at least 3.4, at least 3.6, at least 3.8, or at least 4.0 when compared to said parent alpha-amylase having alpha-amylase activity wherein said IF is determined by using Model A and/or Model J detergent composition and wherein said parent alpha-amylase has amino acid sequence as shown in SEQ ID NO: 1 and/or SEQ ID NO: 2.

In one aspect, the present invention relates to alpha-amylase variants comprises at least one of the following alterations or combinations of alterations:

I. T5L+N33Y+K35A+S36E+K37H+N95R+G109A+H183*+G184*+E190P+Q280N+W284F+N296Q+L297F+N311K+I312L+F313L+Q319S+R320K+H324K+S334T+L355F+T356I+Q361S+Y371M+R383K+S384H+D387E+E391K+Q394K+K395Q+P400A;

II. M105I+G109A+V131I+Y135H+Q169E+N174*+H183*+G184*+I206Y+M208Y+L217I+I235L+T246L+I250V+A263T+F343T+E346T+I374T+V379I+M382L+V410I+K423N+S437A+A442V+L444A+Y452H+D460E+T461P+K463V+G465N+D467E+K485R;

III. N22Q+N25R+N28Q+S29N+A51T+N54A+N70H+R82K+S83G+Q84E+V89I+T90K+K93H+Q98N+M116D+R118T+E130V+T136L+E138K+R142H+D144H+N150S+H152Y+S154D+R158Y+R181Q+H183*+G184*+E190P+T225A+T227E+G229Q+T356I+Q361S;

IV. A51T+N54A+Q98N+G109A+M116D+R118Q+E130V+T136L+E138K+R142H+D144H+S154D+R158Y+N174*+R181Q+H183*+G184*+E190P+I206L+E212D+V214A+R218K+N219R+V222T+T225A+S255E+A256K+W284F+N311K+R320K+H324K+S334T+T356I+Q361S+V410I+R439T+W469N+E471T;

V. N22Q+N25K+N28Q+S29N+A51T+N54A+N70H+Q84D+V89I+T90K+K93H+Q98N+M116D+R118Q+E130V+V131I+T136L+E138K+N174*+R181Q+H183*+G184*+I206L+G229Q+Q319S+R320K+F343T+E346T+I374T+V379I+M382L+R383K+P400A+K423N+L444A+K463V;

VI. A51T+N54A+G109A+R118T+E134D+W140Y+R172S+H183*+G184* E190P+I206L+Y243F+F267Y+Q280N+K281 F+N299A+K302N+R320K+S334T+A339S+V410I+E471T+D476K;

VII. K35A+A51T+N54A+G109A+R118T+W140Y+R172S+N174*+R181Q+H183*+G184*+E190P+I206L+I235L+Y243F+F267Y+Q280N+K281F+N299A+K302T+R320K+S334T+A339S+E345Q+E346P+V410I;

VIII. H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471T+D476K;

IX. K35A+A51T+N54A+D62N+M105I+G109A+R118T+V131I+Y135H+W140Y+Q169E+R172S+N174*+H183*+G184*+E190P+I206L+M208Y+L217I+I235L+Y243F+T246L+1250V+A263T+F267Y+Q280N+K281 F+N299A+K302T+F343T+E346T+I374T+V379I+M382L+V410I+K423N+S437A+A442V+L444A+Y452H+D460E+T461P+K463V+G465N+D467E+E471T+D476K+K485R;

X. N22Q+N25R+N28Q+S29N+A51T+N54A+N70H+R82K+S83G+Q84E+V89I+T90K+K93H+Q98N+G109A+M116D+R118T+E130V+T136L+E138K+W140Y+R142H+D144H+N150S+H152Y+S154D+R158Y+R172S+N174*+R181Q+H183*+G184*+E190P+I206L+Y243F+F267Y+Q280N+K281 F+N299A+K302N+R320K+S334T+A339S+E345Q+E346P+T356I+Q361 S+V410I+E471 T+D476K;

XI. A51T+N54A+Q98N+G109A+M116D+R118Q+E130V+T136L+E138K+W140Y+R142H+D144H+S154D+R158Y+N174*+R181Q+H183*+G184*+E190P+I206L+E212D+V214A+R218K+N219R+V222T+T225A+S255E+A256K+Q280N+W284F+K302N+N311K+R320K+H324K+S334T+T356I+Q361 S+V410I+R439T+W469N+E471T+D476K;

XII. N22Q+N25K+N28Q+S29N+K35A+A51 T+N54A+N70H+Q84D+V89I+T90K+K93H+Q98N+G109A+

M116D+R118Q+E130V+V131I+T136L+E138K+W167F+R172S+R181 Q+H183*+G184*+I206L+G229Q+I235L+Y243F+F267Y+Q280N+K281 F+N299A+K302N+Q319S+R320K+S334T+A339S+F343T+E345Q+E346T+I374T+V379I+M382L+R383K+P400A+V410I+K423N+L444A+K463V+E471 T+D476K;

XIII. N174S+H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471 T+D476K;

XIV. H1A+H2*+N3A+M9L+K35A+W48Y+A51T+N54A+M105I+G109A+R118T+W140Y+R172S+R181Q+E188P+I204L+I233L+Y241F+T244L+F265Y+Q278N+K279F+N297A+K300T+R318K+S332T+A337S+E343Q+E344P+V377I+M380L+V408I+D474K;

XV. H1*+H2*+N3A+M9L+K35A+W48Y+A51T+N54A+M105I+G109A+R118Q+W140Y+R172S+R181Q+E188P+I204L+V212I+I233L+Y241F+T244L+F265Y+Q278N+K279F+N297A+K300T+R318K+S332T+A337S+E343Q+E344P+V377I+M380L+V408I+D474K;

XVI. H1A+N3A+K35A+A51T+N54A+G109A+R118T+W140Y+R172S+N174S+R181Q+H183*+G184*+E190P+I206L+I235L+Y243F+F267Y+Q280N+K281F+N299A+K302T+R320K+S334T+A339S+E345Q+E346P+P408H+V410I+I411V+K423N+S437A+A442V+L444R+K445Q+Y452H+D460E+T461P+K463V+G465N+D467E+D476K+K485R;

XVII. H1A+N3A+G4N+T5L+M9L+L17M+N22Q+N25R+N28Q+S29N+A31S+S32A+N33Y+K35A+S36E+K37H+W48Y+A51T+N54A+M105I+G109A+R118T+E134D+W140Y+R172S+N174S+H183*+G184*+E190P+I206L+Y243F+F267Y+Q280N+W284F+N299A+K302N+Q319S+R320K+S323L+H324K+A325S+S334T+A339S+V379I+M382L+V410I+E471T+D476K;

XVIII. H1A+N3A+A51T+N54A+G109A+R118T+E134D+W140Y+R172S+N174S+H183*+G184*+E190P+I206L+Y243F+F267Y+Q280N+K281 F+N299A+K302N+R320K+S334T+A339S+V410I+I411V+K423N+S437A+A442V+L444R+K445Q+Y452H+D460E+T461P+K463V+G465N+D467E+D476K+K485R;

XIX. H1A+N3A+M9L+K35A+W48Y+A51T+N54A+M105I+G109A+R118T+W140Y+R172S+N174*+R181Q+H183*+G184*+E190P+I206L+I235L+Y243F+T246L+F267Y+Q280N+K281F+N299A+K302T+R320K+S334T+A339S+E345Q+E346P+V379I+M382L+V410I+D476K;

XX. N174S+H183*+G184*+N311K+I312L+F313L+Q319S+R320K+H324K+S334T+E345Q+E346P+L355F+T356I+Q361S+Y371M+V379I+R383K+S384H+D387E+E391K+Q394K+K395Q+P400A+P408H+V410I+I411V+K423N+S437A+A442V+L444R+K445Q+Y452H+D460E+T461P+K463V+G465N+D467E+D476K+K485R;

XXI. H1*+N28R+S36D+T40S+A51T+N54A+V75I+S83N+T90N+S91A+N94S+G109A+R118N+T132S+E134D+W140Y+R142K+S154N+R172S+H183*+G184*+A186G+E190P+N1 95F+I206L+Y243F+F267Y+Q280N+K281 F+N299S+K302N+N311 Q+R320K+S323M+S334T+A339S+T356I+Q361S+R383K+P400R+P408H+V410I+I411V+K423N+S437A+A442V+L444R+K445Q+Y452H+D460E+T461P+K463V+G465N+D467E+E471T+D476K+K485R;

XXII. N174S+H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471 T+D476K;

XXIII. N174S+H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+P408H+V410I+I411V+K423N+S437A+A442V+L444R+K445Q+Y452H+D460E+T461P+K463V+G465N+D467E+D476K+K485R;

XXIV. H1*+N3A+M9L+K35A+W48Y+A51T+N54A+M105I+G109A+R118T+W140Y+R172S+N174*+R181Q+H183*+G184*+E190P+I206L+I235L+Y243F+T246L+F267Y+Q280N+K281F+N299A+K302T+R320K+S334T+A339S+E345Q+E346P+T356I+Q361S+V379I+M382L+V410I+D476K;

XXV. H1*+N3A+K35A+A51T+N54A+G109A+R118T+W140Y+R172S+N174S+R181Q+H183*+G184*+E190P+I206L+I235L+Y243F+F267Y+Q280N+K281F+N299A+K302T+R320K+S334T+A339S+E345Q+E346P+T356I+Q361S+P408H+V410I+I411V+K423N+S437A+A442V+L444R+K445Q+Y452H+D460E+T461P+K463V+G465N+D467E+D476K+K485R;

XXVI. H1*+N3A+K35A+A51T+N54A+G109A+R118T+W140Y+R172S+N174S+R181Q+H183*+G184*+E190P+I206L+I235L+Y243F+F267Y+Q280N+K281F+N299A+K302T+R320K+S334T+A339S+E345Q+E346P+T356I+Q361S+P408H+V410I+I411V+K423N+S437A+A442V+L444R+K445Q+Y452H+D460E+T461P+K463V+G465N+D467E+D476K+K485R;

XXVII. H1*+N3A+A51T+N54A+G109A+R118T+E134D+W140Y+R172S+N174S+H183*+G184*+E190P+I206L+Y243F+F267Y+Q280N+K281 F+N299A+K302N+R320K+S334T+A339S+V410I+I411V+K423N+S437A+A442V+L444R+K445Q+Y452H+D460E+T461P+K463V+G465N+D467E+D476K+K485R;

XXVIII. R118N+N174S+H183*+G184*+E190P+I206L+Y243F+F267Y+K281F+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471T+D476K;

XXIX. R118Q+N174S+H183*+G184*+E190P+I206L+Y243F+F267Y+K281F+N311K+I312L+F313L+Q319S+R320K+H324K+S334T+E345Q+E346P+L355F+T356I+Q361S+Y371M+R383K+S384H+D387E+E391K+Q394K+K395Q+P400A+P408H+V410I+I411V+K423N+S437A+A442V+L444R+K445Q+Y452H+D460E+T461P+K463V+G465N+D467E+D476K+K485R;

XXX. H1*+N3A+M9L+K35A+W48Y+A51T+N54A+M105I+G109A+R118Q+W140Y+R172S+N174*+R181Q+H183*+G184*+E190P+I206L+V214I+I235L+Y243F+T246L+F267Y+Q280N+K281F+N299A+K302T+R320K+S334T+A339S+E345Q+E346P+V379I+M382L+V410I+D476K+K485R;

XXXI. H1*+H2*+N3A+G4A+L17V+N22Q+H23Q+N28R+S29T+S32P+N33Y+K35S+K37V+T40N+I44T+W48Y+A51T+N54A+A60P+R82K+S83G+

Q84E+Q86K+A87S+T90N+S91T+K93H+N94S+G109A+A113Y+M116N+R118T+N125S+N128Y+V131I+T132S+T136N+E138Q+R142G+D144N+N150T+H152Y+S154N+F155W+R158Q+Y160F+V165T+R172S+N174*+N175S+Y178F+R181D+H183*+G184*+E190P+D192S+T193S+I206Y+M208Y+E212D+L217M+R218K+N219K+T225A+T227E+L228V+F233Y+1235L+Y243F+T246L+R247K+I250V+N251 D+H252N+V253A+S255A+N260E+A263T+A265G+F267Y+K269Q+I275L+E276N+Q280A+T282V+W284Y+H286Q+V288L+V291A+L297F+N299A+K302T+S303G+N306Y+F313L+G315N+V317L+Q319A+R320S+H321N+S323T+H324K+F328L+D330E+S334T+E337G+E338Q+A339S+F343T+E345Q+E346P+W347R+L355F+T356I+E360S+Q361G+Y371M+*372aG+*372bT+*372cK+I374T+P375T+H377R+G378E+V379I+M382L+R383K+D387E+I389L+E391K+Q394K+K395D+P400T+H402R+H407N+S420T+L429V+A442V+L444T+K445S+T450I+I454L+S459T+T461K+V462I+K463T+W469Y+G470A+E471T+H473P+D476K+G477E+I481V+Y482W+K485Q;

XXXII. H1*+N3D+T5L+M9I+Y16N+L17V+N22Q+N25R+N28Q+S29N+D30N+S32Q+N33Y+K35A+S36E+K37H+V42I+A51T+N54A+V56T+N70H+R82K+S83G+Q84E+Q86E+A87R+V89I+T90K+K93H+N94A+N95R+Q98N+G109A+A113Q+M116D+R118N+N125Q+E130V+T132S+E134T+T136L+E138K+W140Y+R142H+D144H+N150S+T151Q+H152Y+S154D+R158Y+V165T+R172S+N174*+R181Q+G182T+H183*+G184*+E190P+N195F+I206L+V214I+R218N+N219R+T225A+T227E+G229Q+I235L+Y243F+T246M+I250L+N251G+S255G+A256Q+M261L+F267Y+I275L+Q280N+K281 F+N285T+H286M+V288A+N299S+K302N+G304S+I312L+F313L+V317L+R320K+S334T+E337G+A339S+E345Q+E346P+L355T+T356I+Q361S+Y371M+I374T+P375S+T376Q+H377R+G378E+A381S+M382Y+S384Q+K385Q+I389L+E391A+K395Q+P400A+H407N+P408Q+V410I+S420A+K423G+L429V+I430M+T431 S+R439T+A442V+L444T+K445A+N446H+E449Q+T450V+W451 F+Y452K+S459T+K463T+G465N+D467A+W469T+E471T+H473R+V474C+D476K+Y482W+Q484K+K485Q;

XXXIII. H1*+N3D+T5L+M9I+Y16N+L17V+N22Q+N25R+N28Q+S29N+D30N+S32Q+N33Y+K35A+S36E+K37H+V42I+A51T+N54A+V56T+N70H+R82K+S83G+Q84E+Q86E+A87R+V89I+T90K+K93H+N94A+N95R+Q98N+G109A+A113Q+M116D+R118N+N125Q+E130V+T132S+E134T+T136L+E138K+W140Y+R142H+D144H+N150S+T151Q+H152Y+S154D+R158Y+V165T+R172S+N174*+R181Q+H183*+G184*+G184T+E190P+N195F+I206L+V214I+R218N+N219R+T225A+T227E+G229Q+I235L+Y243F+T246M+I250L+N251G+S255G+A256Q+M261L+F267Y+I275L+Q280N+K281 F+N285T+H286M+V288A+N299S+K302N+G304S+I312L+F313L+V317L+R320K+S334T+E337G+A339S+E345Q+E346P+L355T+T356I+Q361S+T376S+H377D+A381S+M382Y+S384Q+K385Q+I389L+E391A+K395Q+P400A+H407N+P408Q+V410I+S420A+K423G+L429V+I430M+T431S+R439T+A442V+L444T+K445A+N446H+E449Q+T450V+W451 F+Y452K+D460E+T461P+K463V+G465N+D467A+W469T+E471T+H473R+V474C+D476K+Y482W+Q484K+K485Q;

XXXIV. H1*+N3D+M9L+K35A+W48Y+A51T+N54S+R82K+V89I+M105I+G109A+R118N+W140Y+H152Y+V165T+R172S+N174*+R181Q+H183*+G184*+E190P+I206Y+M208Y+E212D+V214I+L217I+T227E+I235L+Y243F+T246L+N260G+F267Y+I275L+Q280T+K281Y+N299A+K302T+R320K+A325S+S334T+A339S+F343T+E345Q+E346P+T356I+V379I+M382L+R383K+V410I+I430M+D476K, using SEQ ID NO: 1 for numbering and wherein the variant has alpha-amylase activity and wherein the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to SEQ ID NO: 1.

Parent Alpha-Amylases

The parent alpha-amylase may be a polypeptide with at least 60% sequence identity with any one of the polypeptides of SEQ ID Nos: 1, 2, 3, 4, 5, 6, 7, 8, 9, 10, 11, 12 or 13.

In one embodiment, the parent has a sequence identity to the polypeptide of SEQ ID NO: 1 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 1.

The parent preferably comprises or consists of the amino acid sequence of SEQ ID NO: 1. In one embodiment the parent comprises or consists of the polypeptide of SEQ ID NO: 1. In another embodiment, the parent is an allelic variant of the polypeptide of SEQ ID NO: 1.

In one embodiment, the parent has a sequence identity to the polypeptide of SEQ ID NO: 2 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 2.

The parent preferably comprises or consists of the amino acid sequence of SEQ ID NO: 2. In one embodiment the parent comprises or consists of the polypeptide of SEQ ID NO: 2. In another embodiment, the parent is an allelic variant of the polypeptide of SEQ ID NO: 2.

In one embodiment, the parent has a sequence identity to the polypeptide of SEQ ID NO: 3 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 3.

The parent preferably comprises or consists of the amino acid sequence of SEQ ID NO: 3. In one embodiment the parent comprises or consists of the polypeptide of SEQ ID NO: 3. In another embodiment, the parent is an allelic variant of the polypeptide of SEQ ID NO: 3.

In one embodiment, the parent has a sequence identity to the polypeptide of SEQ ID NO: 4 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 4.

The parent preferably comprises or consists of the amino acid sequence of SEQ ID NO: 4. In one embodiment the parent comprises or consists of the polypeptide of SEQ ID NO: 4. In another embodiment, the parent is an allelic variant of the polypeptide of SEQ ID NO: 4.

In one embodiment, the parent has a sequence identity to the polypeptide of SEQ ID NO: 5 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 5.

The parent preferably comprises or consists of the amino acid sequence of SEQ ID NO: 5. In one embodiment the parent comprises or consists of the polypeptide of SEQ ID NO: 5. In another embodiment, the parent is an allelic variant of the polypeptide of SEQ ID NO: 5.

In one embodiment, the parent has a sequence identity to the polypeptide of SEQ ID NO: 6 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 6.

The parent preferably comprises or consists of the amino acid sequence of SEQ ID NO: 6. In one embodiment the parent comprises or consists of the polypeptide of SEQ ID NO: 6. In another embodiment, the parent is an allelic variant of the polypeptide of SEQ ID NO: 6.

In one embodiment, the parent has a sequence identity to the polypeptide of SEQ ID NO: 7 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 7.

The parent preferably comprises or consists of the amino acid sequence of SEQ ID NO: 7. In one embodiment the parent comprises or consists of the polypeptide of SEQ ID NO: 7. In another embodiment, the parent is an allelic variant of the polypeptide of SEQ ID NO: 7.

In one embodiment, the parent has a sequence identity to the polypeptide of SEQ ID NO: 8 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 8.

The parent preferably comprises or consists of the amino acid sequence of SEQ ID NO: 8. In one embodiment the parent comprises or consists of the polypeptide of SEQ ID NO: 8. In another embodiment, the parent is an allelic variant of the polypeptide of SEQ ID NO: 8.

In one embodiment, the parent has a sequence identity to the polypeptide of SEQ ID NO: 9 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 9.

The parent preferably comprises or consists of the amino acid sequence of SEQ ID NO: 9. In one embodiment the parent comprises or consists of the polypeptide of SEQ ID NO: 9. In another embodiment, the parent is an allelic variant of the polypeptide of SEQ ID NO: 9.

In one embodiment, the parent has a sequence identity to the polypeptide of SEQ ID NO: 10 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 10.

The parent preferably comprises or consists of the amino acid sequence of SEQ ID NO: 10. In one embodiment the parent comprises or consists of the polypeptide of SEQ ID NO: 10. In another embodiment, the parent is an allelic variant of the polypeptide of SEQ ID NO: 10.

In one embodiment, the parent has a sequence identity to the polypeptide of SEQ ID NO: 11 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 11.

The parent preferably comprises or consists of the amino acid sequence of SEQ ID NO: 11. In one embodiment the parent comprises or consists of the polypeptide of SEQ ID NO: 11. In another embodiment, the parent is an allelic variant of the polypeptide of SEQ ID NO: 11.

In one embodiment, the parent has a sequence identity to the polypeptide of SEQ ID NO: 12 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 12.

The parent preferably comprises or consists of the amino acid sequence of SEQ ID NO: 12. In one embodiment the parent comprises or consists of the polypeptide of SEQ ID NO: 12. In another embodiment, the parent is an allelic variant of the polypeptide of SEQ ID NO: 12.

In one embodiment, the parent has a sequence identity to the polypeptide of SEQ ID NO: 13 of at least 60% e.g., at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, or 100%, which has alpha-amylase activity. In one embodiment, the amino acid sequence of the parent differs by no more than ten amino acids, e.g., by five amino acids, by four amino acids, by three amino acids, by two amino acids, and by one amino acid from the polypeptide of SEQ ID NO: 13.

The parent preferably comprises or consists of the amino acid sequence of SEQ ID NO: 13. In one embodiment the parent comprises or consists of the polypeptide of SEQ ID NO: 13. In another embodiment, the parent is an allelic variant of the polypeptide of SEQ ID NO: 13.

The amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 or an active fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length or at least 200 nucleotides in length, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material, which is used in a Southern blot.

For purposes of the present invention, hybridization indicates that the polynucleotide hybridizes to a labeled nucleotide probe corresponding to a polynucleotide encoding SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 or a subsequence thereof, under low to very high stringency conditions. Molecules to which the probe hybridizes can be detected using, for example, X-ray film or any other detection means known in the art.

In one aspect, the nucleic acid probe is a polynucleotide that encodes the polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 or an active fragment thereof.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), 50° C. (low stringency), 55° C. (medium stringency), 60° C. (medium-high stringency), 65° C. (high stringency), or 70° C. (very high stringency).

For short probes that are about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The parent may be obtained from microorganisms of any genus. For purposes of the present invention, the term "obtained from" as used herein in connection with a given source shall mean that the parent encoded by a polynucleotide is produced by the source or by a cell in which the polynucleotide from the source has been inserted. In one aspect, the parent is secreted extracellularly.

The parent may be a bacterial alpha-amylase. For example, the parent may be a gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* alpha-amylase, or a gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* alpha-amylase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* alpha-amylase.

In another aspect, the parent is a *Streptococcus equisimilis, Streptococcus pyogenes, Streptococcus uberis*, or *Streptococcus equi* subsp. *Zooepidemicus* alpha-amylase.

In another aspect, the parent is a *Streptomyces achromogenes, Streptomyces avermitilis, Streptomyces coelicolor, Streptomyces griseus*, or *Streptomyces lividans* alpha-amylase.

The parent may be a fungal alpha-amylase. For example, the parent may be a yeast alpha-amylase such as a *Candida, Kluyveromyces, Pichia, Saccharomyces, Schizosaccharomyces*, or *Yarrowia* alpha-amylase. For example, the parent may be a filamentous fungal alpha-amylase such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* alpha-amylase.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* alpha-amylase.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* alpha-amylase.

In another aspect, the parent is a *Bacillus* sp. alpha-amylase, e.g., the alpha-amylase of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13.

It will be understood that forthe aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. The polynucleotide encoding a parent may then be derived by similarly screening a genomic or cDNA library of another microorganism or mixed DNA sample. Once a polynucleotide encoding a parent has been detected with a probe(s), the polynucleotide may be isolated or cloned by utilizing techniques that are known to those of ordinary skill in the art (see, e.g., Sambrook et al., 1989, supra).

The parent may be a hybrid polypeptide in which a portion of one polypeptide is fused at the N-terminus or the C-terminus of a portion of another polypeptide.

The parent may also be a fused polypeptide or cleavable fusion polypeptide in which one polypeptide is fused at the N-terminus or the C-terminus of another polypeptide. A fused polypeptide is produced by fusing a polynucleotide encoding one polypeptide to a polynucleotide encoding another polypeptide.

Techniques for producing fusion polypeptides are known in the art and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Polynucleotides

The present invention also relates to polynucleotides encoding a variant of the present invention. Thus, in particular, the present invention relates to a polynucleotide encoding a variant comprising a) a pairwise deletion of the amino acids corresponding to positions H183*+G184* and b) at least one alteration at a position corresponding to positions: an alteration at one or more positions corresponding to postions: H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311, 1312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, I389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering.

The term "polynucleotides encoding" as used herein, refers to a polynucleotide that encodes a polypeptide having alpha-amylase having alpha-amylase activity.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. Thus, in particular, the present invention relates to a nucleic acid construct comprising a polynucleotide encoding a variant comprising a) a pairwise deletion of the amino acids corresponding to positions H183*+G184* and b) an alteration at one or more positions corresponding to positions: H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311I, I312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, I389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering.

The term "nucleic acid construct" as used herein, refers to a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "operably linked" as used herein, refers to a configuration in which a control sequence is placed at an appropriate position relative to the coding sequence of a polynucleotide such that the control sequence directs expression of the coding sequence.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter comprises transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Expression Vectors

The present invention also relates to recombinant expression vectors comprising a polynucleotide encoding a variant of the present invention, a promoter, and transcriptional and translational stop signals. Thus, the present invention relates to an expression vector, optionally recombinant, comprising a polynucleotide encoding a variant comprising a) a pairwise deletion of the amino acids corresponding to positions H183*+G184* and b) an alteration at one or more positions corresponding to positions: H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311I, I312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, I389, E391, Q394, K395, P400, H402, H407, P408, V410, I411, S420, K423, L429, I430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering, a promotor, and transcriptional and translational stop signals.

The term "expression vector" as used herein, refers to a linear or circular DNA molecule that comprises a polynucleotide encoding a variant and is operably linked to control sequences that provide for its expression.

The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

The skilled person would know which expression vector is the most suitable for specific expression systems. Thus, the present invention is not limited to any specific expression vector, but any expression vector comprising the polynucleotide encoding a variant according to the invention is considered part of the present invention.

Host Cells

The present invention also relates to recombinant host cells, comprising a polynucleotide encoding a variant of the present invention operably linked to one or more control sequences that direct the production of a variant of the present invention. Thus, the present invention relates to a host cell, optionally a recombinant host cell, comprising a polynucleotide encoding a variant comprising a) a pairwise deletion of the amino acids corresponding to positions H183*+G184* and b) an alteration at one or more positions corresponding to positions H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311, 1312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, I389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering operably linked to one or more control sequences that direct the production of the variant.

The term "host cell" as used herein, refers to any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

A construct or vector comprising a polynucleotide is introduced into a host cell so that the construct or vector is maintained as a chromosomal integrant or as a self-replicating extra-chromosomal vector as described earlier. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

Preparation of Variants

The present invention also relates to methods for obtaining a variant having alpha-amylase activity, comprising: (a) introducing into a parent alpha-amylase of SEQ ID NO: 1 a pairwise deletion of the amino acids corresponding to positions H183*+G184* and an alteration at one or more positions corresponding to positions: H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311, 1312, F313, G315, V317, Q319, R320, H321, S323, H324, A325, F328, D330, S334, E337, E338, A339, F343, E345, E346, W347, L355, T356, E360, Q361, Y371, 1374, P375, T376, H377, G378, V379, A381, M382, R383, S384, K385, D387, 1389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering and the variant has alpha-amylase activity; and (b) recovering the variant.

The present invention also relates to methods for obtaining a variant having alpha-amylase activity, comprising: (a) introducing into a parent alpha-amylase of SEQ ID NO: 1 comprising a) a pairwise deletion of the amino acids corresponding to positions H183*+G184* and an alteration at one or more positions corresponding to position: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering.

The variants may be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (several) modifications are created at one or more defined sites in a polynucleotide encoding the parent.

Site-directed mutagenesis can be accomplished in vitro by PCR involving the use of oligonucleotide primers containing the desired modification. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the modification in the polynucleotide. Usually the restriction enzyme that digests at the plasmid and the oligonucleotide is the same, permitting sticky ends of the plasmid and insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, Nat. Med. 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein olgionucleotides are synthesized and assembled upon photo-programable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic constuction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR ampflication. Polynucleotide subsequences may then be shuffled.

Methods of Production

The present invention also relates to methods of producing an alpha-amylase variant, comprising: (a) cultivating a host cell of the present invention under conditions suitable for the expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentor's performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods may include use of specific antibodies, formation of an enzyme product, or disappearance of an enzyme substrate. For example, an enzyme assay may be used to determine the activity of the variant.

The variant may be recovered by methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure variants.

Alternatively, the variant is not recovered, but rather a host cell of the present invention expressing a variant is used as a source of the variant.

Fermentation Broth Formulations or Cell Compositions

The present invention also relates to a fermentation broth formulation or a cell composition comprising a polypeptide of the present invention. Thus, in one embodiment, the fermentation broth formulation or the cell composition comprises a polynucleotide encoding a variant comprising a) a pairwise deletion of the amino acids corresponding to positions H183*+G184* and b) an alteration in one or more positions corresponding to the positions: H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311, 1312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, 1389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering, a nucleic acid construct encoding a variant comprising a) a pairwise deletion of the amino acids corresponding to positions H183*+G184* and b) an alteration in one or more positions corresponding to the positions: H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311, 1312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, I389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering, or an expression vector encoding a variant comprising an alteration in one or more positions corresponding to the positions: H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311, 1312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, I389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering. The fermentation broth product may further comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium.

The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In one embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a particular embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one embodiment, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may comprise the unfractionated contents of the fermentation materials derived at the end of the fermentation. Typically, the cell-killed whole broth or composition comprises the spent culture medium and cell debris present after the microbial cells (e.g., filamentous fungal cells) are grown to saturation, incubated under carbon-limiting conditions to allow protein synthesis. In some embodiments, the cell-killed whole broth or composition comprises the spent cell culture medium, extracellular enzymes, and killed filamentous fungal cells. In some embodiments, the microbial cells present in the cell-killed whole broth or composition may be permeabilized and/or lysed using methods known in the art.

A whole broth or cell composition as described herein is typically a liquid, but may comprise insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions

The present invention also relates to composition comprising a variant of the present invention. Accordingly, the present invention relates to compositions comprising a variant comprising a) a pairwise deletion of the amino acids corresponding to positions H183*+G184* and b) an alteration at one or more positions corresponding to positions: H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311, 1312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, 1389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering.

Preferably, the compositions are enriched in such a variant. The term "enriched" means that the alpha-amylase activity of the composition has been increased, e.g., with an enrichment factor of 1.1.

In one embodiment, the invention is directed to compositions comprising a variant of the present invention in combination with one or more additional components. The choice of additional components is within the skill of the artisan and includes conventional ingredients, including the exemplary non-limiting components set forth below.

In one embodiment, the present invention relates to a composition comprising one or more additional components selected from the group consisting of one or more enzymes, oxidizing agents, bleach activators, bleach catalysts, chelating agents, bulking agents, builders, buffering agents, structurants, sequestrants, optical brighteners, antifoaming agents, enzymes, fragrances, anti-redeposition agents, skin conditioning agents, softness extenders, emulsifiers, crystal growth inhibitors, metal care agents, glass care agents and colorants.

In one embodiment, the present invention relates to a composition comprises a surfactant.

In one embodiment, the present invention relates to a composition wherein the surfactant is one or more surfactants selected from the group consisting of an anionic surfactant, a cationic surfactant, a non-ionic surfactant, zwitterionic surfactant, and amphoteric surfactants or any mixtures thereof.

In one embodiment, the present invention relates to a composition wherein the composition is a detergent composition.

In one embodiment, the composition is a liquid laundry or liquid dish wash composition, such as an Automatic Dish Wash (ADW) liquid detergent composition, or a powder laundry, such as a soap bar, or powder dish wash composition, such as an ADW unit dose detergent composition and such as a Hand Dish Wash (HDW) detergent composition.

In one embodiment, the present invention relates to a composition wherein the composition comprises one or more additional enzymes.

The composition may comprise a variant as the major enzymatic component, e.g., a mono-component composition. Alternatively, the composition may comprise multiple enzymatic activities, such as an proteases, amylases, phospho-lipases, esterases, lipases, cutinases, cellulases, endoglucanases, xyloglucanases, xylanases, pectinases, hemicellulases pectin lyases, xanthanases, peroxidases, keratinases haloperoxygenases, catalases, mannanases, lechinase, RNase, DNAse, reductases, oxidases, phenoloxidases, lipoxygenases, ligninases, pullulanases, tannases, pentosanases, malanases, β-glucanases, arabinosidases, hyaluronidase, chondroitinase, and laccase or any mixture thereof.

The additional enzyme(s) may be produced, for example, by a microorganism belonging to the genus *Bacillus*, e.g. *Bacillus licheniformis* and *Bacillus subtilis*, or the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger*, or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, e.g., *Humicola insolens* or *Humicola lanuginosa*; or *Trichoderma*, e.g., *Trichoderma harzianum, Trichoderma koningii, Trichoderma longibrachiatum, Trichoderma reesei*, or *Trichoderma viride* or any other host cell herein described.

The compositions may be prepared in accordance with methods known in the art and may be in the form of a liquid or a dry composition. For instance, the composition may be in the form of a granulate or a microgranulate. The variant may be stabilized in accordance with methods known in the art.

Such compositions comprise a cleaning/detergent components, preferably a mixture of components. Typically, the cleaning components will be present in the composition in an amount from 0.001 to 99.9 wt %, more typically from 0.01 to 80 wt % cleaning component.

In another preferred aspect the composition comprises one or more surfactants, which may be non-ionic including semi-polar and/or anionic and/or cationic and/or zwitterionic and/or ampholytic and/or semi-polar nonionic and/or mixtures thereof. The surfactants are typically present at a level of from 0.1% to 60% by weight or from 0.5 to 50 wt % or 1 to 40 wt % of the composition.

In one embodiment of the present invention, the variant of the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor. The term "protein" in this context is contemplated to be understood to include a variant according to the present invention.

A composition for use in automatic dish wash (ADW), for example, may include 0.0001%-50%, such as 0.001%-20%, such as 0.01%-10%, such as 0.05-5% of enzyme protein by weight of the composition.

A composition for use in hand dish wash (HDW), for example, may include 0.0001%-50%, such as 0.001%-20%, such as 0.01%-10%, such as 0.05-5% of enzyme protein by weight of the composition.

A composition for use in laundry granulation, for example, may include 0.0001%-50%, such as 0.001%-20%, such as 0.01%-10%, such as 0.05%-5% of enzyme protein by weight of the composition.

A composition for use in laundry liquid, for example, may include 0.0001%-10%, such as 0.001-7%, such as 0.1%-5% of enzyme protein by weight of the composition.

The variants of the invention as well as the further active components, such as additional enzymes, may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708.

In certain markets different wash conditions and, as such, different types of detergents are used. This is disclosed in e.g. EP 1 025 240. For example, In Asia (Japan) a low detergent concentration system is used, while the United States uses a medium detergent concentration system, and Europe uses a high detergent concentration system.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. Such detergent compositions are all embodiments of the invention.

A variant of the present invention may also be incorporated in the detergent formulations disclosed in WO97/07202, which is hereby incorporated by reference.

Examples are given herein of preferred uses of the compositions of the present invention. The dosage of the composition and other conditions under which the composition is used may be determined on the basis of methods known in the art.

In particular, a composition according to the present invention further comprises a chelator.

The term "chelator" as used herein, refers to chemicals which form molecules with certain metal ions, inactivating the ions so that they cannot react with other elements. Thus, a chelator may be defined as a binding agent that suppresses chemical activity by forming chelates. Chelation is the formation or presence of two or more separate bindings between a ligand and a single central atom. The ligand may be any organic compound, a silicate or a phosphate. In the present context the term "chelating agents" comprises chelants, chelating agent, chelating agents, complexing agents, or sequestering agents that forms water-soluble complexes with metal ions such as calcium and magnesium. The chelate effect describes the enhanced affinity of chelating ligands for a metal ion compared to the affinity of a collection of similar nonchelating ligands for the same metal. Chelating agents having binding capacity with metal ions, in particular calcium (Ca2+) ions, and has been used widely in detergents and compositions in general for wash, such as laundry or dish wash. Chelating agents have however shown themselves to inhibit enzymatic activity. The term chelating agent is used in the present application interchangeably with "complexing agent" or "chelating agent" or "chelant".

Since most alpha-amylases are calcium sensitive the presence of chelating agents these may impair the enzyme activity. The calcium sensitivity of alpha-amylases can be determined by incubating a given alpha-amylase in the presence of a strong chelating agent and analyze the impact of this incubation on the activity of the alpha-amylase in question. A calcium sensitive alpha-amylase will lose a major part or all of its activity during the incubation. Chelating agent may be present in the composition in an amount from 0.0001 wt % to 20 wt %, preferably from 0.01 to 10 wt %, more preferably from 0.1 to 5 wt %.

Non-limiting examples of chelating agents are; EDTA, DTMPA, HEDP, and citrate. Thus, in one embodiment, the composition comprises a variant according to the invention and a chelating agent, such as EDTA, DTMPA, HEDP or citrate.

The term "EDTA" as used herein, refers to ethylene-diamine-tetra-acetic acid which falls under the definition of "strong chelating agents".

The term "DTMPA" as used herein, refers to diethylenetriamine penta(methylene phosphonic acid). DTMPA can inhibit the scale formation of carbonate, sulfate and phosphate.

The term "HEDP" as used herein, refers to hydroxyethane diphosphonic acid, which falls under the definition of "strong chelating agents".

The chelate effect or the chelating effect describes the enhanced affinity of chelating ligands for a metal ion compared to the affinity of a collection of similar nonchelating ligands for the same metal. However, the strength of this chelate effect can be determined by various types of assays or measure methods thereby differentiating or ranking the chelating agents according to their chelating effect (or strength).

In an assay the chelating agents may be characterized by their ability to reduce the concentration of free calcium ions (Ca2+) from 2.0 mM to 0.10 mM or less at pH 8.0, e.g. by using a test based on the method described by M. K. Nagarajan et al., JAOCS, Vol. 61, no. 9 (September 1984), pp. 1475-1478.

For reference, a chelator having the same ability to reduce the concentration of free calcium ions (Ca2+) from 2.0 mM to 0.10 mM at pH as EDTA at equal concentrations of the chelator are said to be strong chelators.

The composition of the present invention may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multicompartments. It can be of any form, shape and material which is suitable for hold the composition, e.g. without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivatives thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, maltodextrin, polymethacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients may be separated physically from each other by compartments in water dissolvable pouches or in different layers of tablets. Thereby negative storage interaction between components may be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Another form of composition is in the form of a soap bar, such as a laundry soap bar, and may be used for hand washing laundry, fabrics and/or textiles. The term "soap bar" as used herein, refers to includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term "solid" as used herein, refers to a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The soap bar may also comprise complexing agents like EDTA and HEDP, perfumes and/or different type offillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the soap bars by any single method. The premix of the invention may be added to the soap at different stages of the process. For example, the premix comprising a soap, an enzyme, optionally one or more additional enzymes, a protease inhibitor, and a salt of a monovalent cation and an organic anion may be prepared and the mixture may then plodded. The enzyme and optional additional enzymes may be added at the same time as an enzyme inhibitor, e.g. a protease inhibitor, for example in liquid form. Besides the mixing step and the plodding step, the process may further comprise the steps of milling, extruding, cutting, stamping, cooling and/or wrapping.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 0% to about 40% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), epoxy-capped poly(oxyalkylated) alcohols, alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 0% to about 40% by weight of a zwitterionic surfactant. Non-limiting examples of zwitterionic surfactants include betaine, alkyldimethylbetaine, sulfobetaine, and combinations thereof.

The detergent composition may also comprise one or more isoprenoid surfactants as disclosed in US 20130072416 or US 20130072415.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry/ADW/hard surface cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), a-alanine-N,N-diacetic acid (a-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-30% by weight, such as about 1% to about 20%, of a bleaching system. Any bleaching system known in the art for use in laundry/ADW/hard surface cleaning detergents may be utilized. Suitable bleaching system components include bleaching catalysts, photobleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU). N-acylimides, in particular N-nonanoylsuccinimide (NOSI), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy) benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst, for example manganese triazacyclononane, manganese oxalate, Co, Cu, Mn and Fe bispyridylamine and pentamine acetate cobalt(III). In some embodiments the bleach component may be an organic catalyst selected from the group consisting of organic catalysts having the following formulae:

(i)

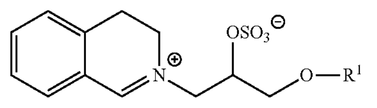

-continued (ii)

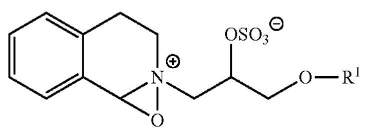

(iii) and mixtures thereof;

wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Adjunct Materials

Any detergent components known in the art for use in laundry, ADW or hard surface cleaning detergents may also be utilized. Other optional detergent components include anti-corrosion agents, anti-shrink agents, anti-soil redeposition agents, anti-wrinkling agents, bactericides, binders, corrosion inhibitors, metal care agents, glass care agents, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry, ADW or hard surface cleaning detergents may be utilized. The choice of such ingredients is well within the skill of the artisan.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2,2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Enzymes

In one embodiment, the composition according to the invention comprises one or more further enzymes, such as at least two enzymes, more preferred at least three, four or five enzymes. Preferably, the enzymes of the detergent composition have different substrate specificity, e.g., proteolytic activity, amylolytic activity, lipolytic activity, cellulytic activity, hemicellulytic activity, oxidative activity, RNAse activity, DNAse activity or pectolytic activity.

The composition according to the invention may comprise one or more additional enzymes selected from proteases, second amylases, lipases, cutinases, cellulases, endoglucanases, lechinase, xyloglucanases, pectinases, pectin lyases, xanthanases, peroxidases, haloperoxygenases, catalases, mannanases, or any mixture thereof. Other suitable enzymes include carbohydrate-active enzymes like carbohydrase, arabinase, galactanase, xylanase; or oxidases, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

In one aspect preferred enzymes include a cellulase. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme□, and Carezyme□ (Novozymes A/S) Carezyme Premium□ (Novozymes A/S), Celluclean□ (Novozymes A/S), Celluclean Classic□ (Novozymes A/S), Cellusoft□ (Novozymes A/S), Whitezyme□ (Novozymes A/S), Clazinase□, and Puradax HA□ (Genencor International Inc.), and KAC-500(B)□ (Kao Corporation).

Mannanases

In one aspect preferred enzymes include a mannanase. Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Peroxidases/Oxidases

In one aspect preferred enzymes include a peroxidase. A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257. Commercially available peroxidases include Guardzyme□ (Novozymes A/S).

A peroxidase according to the invention also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as Caldariomyces, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

Proteases

In one aspect preferred enzymes include a protease. Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO09/021867, and Subtilisin *lentus*, Subtilisin Novo, subtilisin Carlsberg, *Bacillus licheniformis*, subtilisin BPN', subtilisin 309, subtilisin 147 and subtilisin 168 and e.g. protease PD138 described in (WO93/18140). Other useful proteases may be those described in WO01/016285 and WO02/016547. Examples of trypsin-like proteases are trypsin (e.g. of porcine or bovine origin) and the *Fusarium* protease described in WO94/25583 and WO05/040372, and the chymotrypsin proteases derived from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Proctor & Gamble/Genencor Int.) such as those derived from *Bacillus amyloliquefaciens.*

Examples of useful proteases are the variants described in: WO89/06279 WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO 1 of WO 2016/001449. More preferred the protease variants may comprise one or more of the mutations selected from the group consisting of: S3T, V41, S9R, S9E, A15T, S24G, S24R, K27R, N42R, S55P, G59E, G59D, N60D, N60E, V66A, N74D, S85R, A96S, S97G, S97D, S97A, S99E, S99D, S99G, S99M, S99N, S99R, S99H, S101A, V1021, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V1 991, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease shown in SEQ ID NO 1 of WO2016/001449, the *Bacillus amylolichenifaciens* protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO2004/067737.

In one embodiment, the protease is a variant of the polypeptide of SEQ ID NO: 19 comprising the mutation S99D, wherein position numbers correspond to positions of the polypeptide of SEQ ID NO: 20, for example a variant having at least 80%, at least 85%, at least 90%, at least 95%, at least 96%, at least 97% or at least 98% sequence identity to SEQ ID NO: 19. In one embodiment, the protease comprises or consists of the polypeptide of SEQ ID NO: 19 with the mutation S99D.

In one embodiment, the protease is a variant of the polypeptide of SEQ ID NO: 19 comprising the mutation S99E, wherein position numbers correspond to positions of the polypeptide of SEQ ID NO: 20, for example a variant having at least 80%, at least 85%, at least 90%, at least 95%, at least 96%, at least 97% or at least 98% sequence identity to SEQ ID NO: 19. In one embodiment, the protease comprises or consists of the polypeptide of SEQ ID NO: 19 with the mutation S99E.

In one embodiment, the protease is a variant of the polypeptide of SEQ ID NO: 19 comprising the mutations Y167A+R170S+A194P, wherein position numbers correspond to positions of the polypeptide of SEQ ID NO: 20, for example a variant having at least 80%, at least 85%, at least 90%, at least 95%, at least 96%, at least 97% or at least 98% sequence identity to SEQ ID NO: 19. In one embodiment, the protease comprises or consists of the polypeptide of SEQ ID NO: 19 with the mutations Y167A+R170S+A194P.

In one embodiment, the protease is a variant of the polypeptide of SEQ ID NO: 19 comprising the mutations S9E+N43R+N76D+V205I+Q206L+Y209W+S259D+N261W+L262E, wherein position numbers correspond to positions of the polypeptide of SEQ ID NO: 20, for example a variant having at least 80%, at least 85%, at least 90% or at least 95% sequence identity to SEQ ID NO: 19. In one embodiment, the protease comprises or consists of the polypeptide of SEQ ID NO: 19 with the mutations S9E+N43R+N76D+V205I+Q206L+Y209W+S259D+N261W+L262E.

In one embodiment, the protease is a variant of the polypeptide of SEQ ID NO: 19 comprising the mutations S3T+V4I+S99D+S101R+S103A+V104I+G160S+V199M+V205I+L217D, wherein position numbers correspond to positions of the polypeptide of SEQ ID NO: 20, for example a variant having at least 80%, at least 85%, at least 90% or at least 95% sequence identity to SEQ ID NO: 19. In one embodiment, the protease comprises or consists of the polypeptide of SEQ ID NO: 19 with the mutations S3T+V4I+S99D+S101R+S103A+V104I+G160S+V199M+V205I+L217D.

In one embodiment, the protease is a variant of the polypeptide of SEQ ID NO: 19 comprising the mutations S3T+V4I+S99D+S101E+S103A+V104I+G160S+V2051, wherein position numbers correspond to positions of the polypeptide of SEQ ID NO: 20, for example a variant having at least 80%, at least 85%, at least 90% or at least 95% sequence identity to SEQ ID NO: 19. In one embodiment, the protease comprises or consists of the polypeptide of SEQ ID NO: 19 with the mutations S3T+V4I+S99D+S101E+S103A+V104I+G160S+V2051.

In one embodiment, the protease is a variant of the polypeptide of SEQ ID NO: 19 comprising the mutations S99D+S101E+S103A+V104I+G160S, wherein position numbers correspond to positions of the polypeptide of SEQ ID NO: 20, for example a variant having at least 80%, at least 85%, at least 90%, at least 95% or at least 96% sequence identity to SEQ ID NO: 19. In one embodiment, the protease comprises or consists of the polypeptide of SEQ ID NO: 19 with the mutations S99D+S101E+S103A+V104I+G160S.

In one embodiment, the protease is a variant of the polypeptide of SEQ ID NO: 19 comprising the mutations S99D+S101E+S103A+V104I+S156D+G160S+L262E, wherein position numbers correspond to positions of the polypeptide of SEQ ID NO: 20, for example a variant having at least 80%, at least 85%, at least 90% or at least 95% sequence identity to SEQ ID NO: 19. In one embodiment, the protease comprises or consists of the polypeptide of SEQ ID NO: 19 with the mutations S99D+S101E+S103A+V104I+S156D+G160S+L262E.

In one embodiment, the protease is a variant of the polypeptide of SEQ ID NO: 19 comprising the mutations S87N+S101G+V104N, wherein position numbers correspond to positions of the polypeptide of SEQ ID NO: 20, for example a variant having at least 80%, at least 85%, at least 90%, at least 95%, at least 96%, at least 97% or at least 98% sequence identity to SEQ ID NO: 19. In one embodiment, the protease comprises or consists of the polypeptide of SEQ ID NO: 19 with the mutations S87N+S101G+V104N.

In one embodiment, the protease comprises or consists of the polypeptide of SEQ ID NO: 20.

In one embodiment, the protease is a variant of the polypeptide of SEQ ID NO: 20 comprising the mutation Y217L, for example a variant having at least 80%, at least 85%, at least 90%, at least 95%, at least 96%, at least 97% or at least 98% sequence identity to SEQ ID NO: 20. In one embodiment, the protease comprises or consists of the polypeptide of SEQ ID NO: 20 with the mutation Y217L.

In one embodiment, the protease is a variant of the polypeptide of SEQ ID NO: 20 comprising the mutations S24G+S53G+S78N+S101N+G128S+Y217Q, for example a variant having at least 80%, at least 85%, at least 90%, at least 95% or at least 96% sequence identity to SEQ ID NO: 20. In one embodiment, the protease comprises or consists of the polypeptide of SEQ ID NO: 20 with the mutations S24G+S53G+S78N+S101N+G128S+Y217Q.

In one embodiment, the protease is a variant of the polypeptide of SEQ ID NO: 20 comprising the mutations S24G+S53G+S78N+S101N+G128A+Y217Q, for example a variant having at least 80%, at least 85%, at least 90%, at least 95% or at least 96% sequence identity to SEQ ID NO: 20. In one embodiment, the protease comprises or consists of the polypeptide of SEQ ID NO: 20 with the mutations S24G+S53G+S78N+S101N+G128A+Y217Q.

In one embodiment, the protease comprises or consists of the polypeptide of SEQ ID NO: 21.

In one embodiment, the protease is a variant of the polypeptide of SEQ ID NO: 21 having at least 80%, at least 85%, at least 90% or at least 95% sequence identity to SEQ ID NO: 21. The protease may e.g. be a variant of the polypeptide of SEQ ID NO: 21 comprising one or more mutations selected from the group consisting of S27K, N109K, S111E, S171E, S173P, G174K, S175P, F180Y, G182A, L184F, Q198E, N199K and T297P, for example 1, 2, 3, 4, 5, 6, 7, 8, 9, 10, 11, 12 or all of said mutations.

In one embodiment, the protease is a variant of the polypeptide of SEQ ID NO: 21 comprising the mutations S27K+N109K+S111E+S171E+S173P+G174K+S175P+F180Y+G182A+L184F+Q198E+N199K+T297P, for example a variant having at least 80%, at least 85%, at least 90% or at least 95% sequence identity to SEQ ID NO: 21. In one embodiment, the protease comprises or consists of the polypeptide of SEQ ID NO: 21 with the mutations S27K+N109K+S111E+S171E+S173P+G174K+S175P+F180Y+G182A+L184F+Q198E+N199K+T297P.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity®100T, Blaze Evity®125T, Blaze Evity®150T, Neutrase®, Everlase®, Esperase®, Novozymes Progress®, Novozymes Progress® Uno and Novozymes Progress® Excel (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™ Purafect Prime®, Preferenz P110™, Effectenz P1000™ PurafectS™, Effectenz P1050™ Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Nucleases

Suitable nucleases include deoxyribonucleases (DNases) and ribonucleases (RNases) which are any enzyme that catalyzes the hydrolytic cleavage of phosphodiester linkages in the DNA or RNA backbone respectively, thus degrading DNA and RNA. There are two primary classifications based on the locus of activity. Exonucleases digest nucleic acids from the ends. Endonucleases act on regions in the middle of target molecules. The nuclease is preferably a DNase, which is preferable is obtainable from a microorganism, preferably a fungi or bacterium. In particular, a DNase which is obtainable from a species of *Bacillus* is preferred; in particular a DNase which is obtainable from *Bacillus cibi, Bacillus subtilis* or *Bacillus licheniformis* is preferred. Examples of such DNases are described in WO 2011/098579, WO2014/087011 and WO2017/060475. Particularly preferred is also a DNase obtainable from a species of *Aspergillus*; in particular a DNase which is obtainable from *Aspergillus oryzae*, such as a DNase described in WO 2015/155350. The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates as described above, liquids, in particular stabilized liquids, or slurries.

Lipases and Cutinases

In one aspect preferred enzymes include a lipase and/or cutinase. Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

In one aspect preferred enzymes include another amylase. Suitable amylases which can be used together with the compositions of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, 1201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

$$M197T;$$

$$H156Y+A181T+N190F+A209V+Q264S; \text{ or}$$

$$G48A+T49I+G107A+H156Y+A181T+N190F+I201F+A209V+Q264S.$$

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

$$N128C+K178L+T182G+Y305R+G475K;$$

$$N128C+K178L+T182G+F202Y+Y305R+D319T+G475K;$$

$$S125A+N128C+K178L+T182G+Y305R+G475K; \text{ or}$$

$$S125A+N128C+T131I+T165I+K178L+T182G+Y305R+G475K$$

wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, 1203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

$$E187P+I203Y+G476K$$

$$E187P+I203Y+R458N+T459S+D460T+G476K$$

$$T38N+N126Y+T129I+F153W+R178^*+G179^*+T180D+E187P+I203Y+G476K+G477E$$

wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128K177, R179, S180, 1181, G182, M200, L204, E242, G477 and G478. More preferred variants of SEQ ID NO: 1 are those having the substitution in one of more of the following positions: N21D, D97N, V1281K177L, M200L, L204YF, E242QA, G477K and G478K and/or deletion in position R179 and/or S180 or of 1181 and/or G182. Most preferred amylase variants of SEQ ID NO: 1 are those having the substitutions:

N21 D+D97N+V128I wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Amplify Prime™, Atlantic™, Arctic™, Everest™, Duramyl™, Termamyl™, Fungamyl™, Stainzyme™ Stainzyme Plus™, Natalase™, Liquozyme X and BAN™ (from Novozymes A/S), and Rapidase™, Purastar™/Effectenz™, Powerase, Preferenz S1000, Preferenz S100, Preferenz S110 and Preferenz S210 (from Genencor International Inc./DuPont).

The detergent enzyme(s) may be included in the detergent composition according to the invention by adding separate additives containing one or more enzymes, or by adding a combined additive comprising all of these enzymes. A detergent additive, i.e., a separate additive or a combined additive, may be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Microorganisms

The detergent additive as well as the detergent composition may also comprise one or more microorganisms, such as one or more fungi, yeast, or bacteria.

In an embodiment, the one or more microorganisms are dehydrated (for example by lyophilization) bacteria or yeast, such as a strain of *Lactobacillus*.

In another embodiment, the microrganisms are one or more microbial spores (as opposed to vegetative cells), such as bacterial spores; or fungal spores, conidia, hypha. Preferably, the one or more spores are *Bacillus* endospores; even more preferably the one or more spores are endospores of *Bacillus subtilis, Bacillus licheniformis, Bacillus amyloliquefaciens*, or *Bacillus megaterium.*

The microrganisms may be included in the detergent composition or additive in the same way as enzymes (see above).

It is at present contemplated that in the detergent compositions any enzyme, in particular the alpha amylase polypeptides of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The alpha amylase polypeptides of the invention may additionally be incorporated in the detergent formulations disclosed in WO 2006/002643, which is hereby incorporated as reference.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

A detergent composition according to the invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

Thus, in one embodiment, the detergent composition according to the present invention is a liquid laundry detergent composition, a powder laundry detergent composition, a liquid dishwash detergent composition, or a powder dishwash detergent composition. In an embodiment, the composition is a liquid or powder automatic dishwashing (ADW) detergent composition; or a liquid manual dishwashing detergent composition.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Granular Detergent Formulations

A granular detergent may be formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, and WO09/015951.

WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905,

WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792, WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, WO2010000636.

Formulation of Enzyme in Co-Granule

The enzyme of the invention may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component.

WO 2013/188331 also relates to a method of treating and/or cleaning a surface, preferably a fabric surface comprising the steps of (i) contacting said surface with the detergent composition as claimed and described herein in an aqueous wash liquor, (ii) rinsing and/or drying the surface.

The multi-enzyme co-granule may comprise an enzyme of the invention and (a) one or more enzymes selected from the group consisting of lipases, cellulases, xyloglucanases, perhydrolases, peroxidases, lipoxygenases, laccases, hemicellulases, proteases, cellobiose dehydrogenases, xylanases, phospholipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, second amylases, and mixtures thereof.

Uses

The present invention is also directed to methods for using the alpha-amylase variants. The alpha-amylase variants of the invention are useful in detergent compositions, laundry washing, dishwashing and/or cleaning processes.

In one embodiment, the invention relates the use of variants of the present invention in detergent compositions, for use in cleaning hard-surfaces, such as dish wash, or in laundering or for stain removal. In another embodiment, the invention relates to the use of an alpha-amylase variant according to the invention in a cleaning process such as laundry or hard surface cleaning including, but not limited to, dish wash and industrial cleaning. Thus, in one embodiment, the invention relates to the use of a variant comprising a) a pairwise deletion of the amino acids corresponding to positions H183*+G184* and b) an alteration in one or more positions corresponding to the positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, 1235L, Y243F, T246M, T246L, R247K, I250L, I250V, N251D, N251G, H252N, V253A, S255E, S255G, S255A, A256Q, A256K, N260E, N260G, M261 L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering in a cleaning process such as laundry or hard surface cleaning including dish wash and industrial cleaning.

The soils and stains that are important for cleaning are composed of many different substances, and a range of different enzymes, all with different substrate specificities, have been developed for use in detergents both in relation to laundry and hard surface cleaning, such as dishwashing. These enzymes are considered to provide an enzyme detergency benefit, since they specifically improve stain removal in the cleaning process that they are used in, compared to the same process without enzymes. Stain removing enzymes that are known in the art include enzymes such as proteases, second amylases, lipases, cutinases, cellulases, endoglucanases, xyloglucanases, pectinases, pectin lyases, xanthanases, peroxidaes, haloperoxygenases, catalases and mannanases.

In one aspect, the present invention relates to the use of a variant as described herein, or to the use of a composition comprising the variant, in a domestic or industrial cleaning process.

In one aspect, the present invention relates to the use of a variant as described herein, or to the use of a composition comprising the variant for cleaning of fabric, for example laundry.

In one aspect, the present invention relates to the use of a variant as described herein, or to the use of a composition comprising the variant for cleaning of ceramic, plastic or glass material, for example dishwashing.

In one aspect, the invention relates to a laundering process which may be for household laundering as well as industrial laundering. Furthermore, the invention relates to a process for the laundering of textiles (e.g. fabrics, garments, cloths etc.) where the process comprises treating the textile with a washing solution containing a detergent composition of the present invention. The laundering can for example be carried out using a household or an industrial washing machine or be carried out by hand using a detergent composition of the invention.

In one aspect, the invention relates to a dish wash process, including ADW and/or HDW; or hard surface cleaning, which may be for household cleaning as well as industrial cleaning. Furthermore, the invention relates to a process for dish wash or hard surface cleaning, where the process comprises treating the dishes or hard surfaces with a washing solution comprising a detergent composition of the present invention. The dish wash or hard surface cleaning can for example be carried out using a household dish washing machine or be carried out by hand using a detergent composition of the invention.

Methods of Use

The invention provides a use of a detergent composition in a domestic or industrial cleaning process. A cleaning process may for example be a dishwashing process, such as dishwashing; a laundry process; or cleaning of hard surfaces such as bathroom tiles, floors, table tops, drains, sinks and washbasins.

Dishwashing

An automated dishwashing process may comprise the following steps:

a. Exposing dishware to an aqueous wash liquor comprising a detergent composition;
b. Completing at least one wash cycle; and
c. Optionally rinsing and drying the dishware.

Thus, the invention provides a method of dishwashing in an automatic dishwashing machine using a detergent composition as described herein, comprising the steps of adding said detergent composition in a detergent composition compartment in said automatic dishwashing machine, and releasing said detergent composition during a main-wash cycle.

The compositions may be employed at concentrations from about 1000-8000 ppm in the wash liquor, such as 2000-6000 ppm in the wash liquor. The hardness of the wash liquor may be 3-30° dH. The pH of the wash liquor may be 3-11, such as 7-11.

The temperature of the wash liquor when used may be in the range of 10-70° C. For example the temperature of the wash liquor can be in the range of 15-60° C., in the range of 20-50° C., in the range of 25-50° C., in the range of 30-45° C., in the range of 35-40° C., in the range of 35-55° C., or in the range of 40-50° C.

The temperature may vary throughout the wash program. One enzyme may be activated at one active temperature range and other enzymes may be activated at another active temperature range differing from the active temperature range of the first enzyme. For example, one or more wash cycles may be carried out at a temperature of 32-38° C. and other wash cycles may be carried out at a temperature of 45-55° C. The advantage of this is that the single enzymes are allowed to work at their optimal temperature. The optimal temperature of the enzymes of a detergent composition may vary but is typically in the range of 65-70° C. for proteases and in the range of 55-65° C. for amylases. The optimal temperature may be determined by different assays, such as comparing the activity over a 15 min period of time in a buffered solution at different temperatures.

During or after completion of a wash cycle the dishware can be rinsed with water or with water comprising a rinsing aid. The effectiveness of the cleaning can be further improved if an acidic rinsing aid is used. The rinsing aid should be capable of lowering the pH below 4 during at least a period of the rinsing step. The pH may be even further lowered e.g. to below pH 3.5, such as below pH 3, below pH 2.5 or below pH 2. The period of lowering the pH may be at least 1 minute, such as at least 2 minutes, at least 3 minutes, at least 4 minutes, at least 5 minutes, at least 6 minutes or at least 7 minutes. The period of lowering the pH may even be as long as the time period for the full rinsing step.

The ability of lowering the pH during the rinsing step is due to a buffering agent. A buffer with strong buffer capacity at low pH, from pH 4 and below should be selected. The buffer capacity should correspond to the same effect as the pH drop was done with 15 ml 4M HCL/rinse cycle. The ability of lowering the pH during the rinsing step is due to a buffering agent selected from the group consisting of citric acid, acetic acid, potassium dihydrogen phosphate, boric acid, diethyl barbituric acid, Carmody buffer and Britton-Robinson buffer.

The rinsing aid can further improve the cleaning of the dishware by rinsing away any soil released from the dishware during the washing cycle. In addition, the acidic rinsing aid prevents precipitation of calcium on the dishware.

Laundering

Laundry processes can for example be household laundering, but it may also be industrial laundering. A process for laundering of fabrics and/or garments may be a process comprises treating fabrics with a washing solution containing a detergent composition as described herein. A cleaning process or a textile care process can for example be carried out in a machine washing process or in a manual washing process.

The fabrics and/or garments subjected to a washing, cleaning or textile care process may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibres (tricell), lyocell or blends thereof. The fabrics may also be non-cellulose based such as natural polyamides including wool, camel, cashmere, mohair, rabbit and silk or synthetic polymer such as nylon, aramid, polyester, acrylic, polypropylene and spandex/elastane, or blends thereof as well as blend of cellulose based and non-cellulose based fibres.

In one aspect, the present invention relates to a method of laundering in an automatic laundering machine using a detergent composition as described herein, comprising the steps of adding said detergent composition in a detergent composition compartment in said automatic laundering machine, and releasing said detergent composition during a main wash cycle. In another aspect, the present invention relates to a method of laundering, comprising laundering a garment with a detergent composition as described herein, preferably at a temperature of 50° C. or less, or more preferably at a temperature of 45° C. or less, or even more preferably at a temperature of 40° C. or less even more preferably at a temperature of 35° C. or less or even more preferably at a temperature of 30° C. or less, even more preferably at a temperature of 25° C. or less or even more preferably at a temperature of 20° C. or less.

These methods include a method for laundering a fabric. The method comprises the steps of contacting a fabric to be laundered with a cleaning laundry solution comprising a detergent composition. The fabric may comprise any fabric capable of being laundered in normal consumer use conditions. The solution preferably has a pH from about 5.5 to about 11.5. The compositions may be employed at concentrations from about 100 ppm, preferably 500 ppm to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a degree of hardness of from about 0° dH to about 30° dH. Under typical European wash conditions, the degree of hardness is about 16° dH, under typical US wash conditions about 6° dH, and under typical Asian wash conditions, about 3° dH.

The invention is further described in the following paragraphs:

1. An alpha-amylase variant of a parent alpha-amylase comprising a) a deletion and/or a substitution at two or three or four positions corresponding to positions R181, G182, H183 and G184, and b) an alteration at one or more positions corresponding to positions: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering and wherein each alteration is independently a substitution, insertion, or deletion, and wherein said variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the amino acid sequence to the of SEQ ID NOs: 1-13 and wherein said variant has alpha-amylase activity and wherein the alpha-amylase variant has an improved property relative to said parent alpha-amylase.
2. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NO: 1, and wherein said variant has alpha-amylase activity.

3. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NO: 2, and wherein said variant has alpha-amylase activity.

4. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6%, but less than 100% sequence identity to the polypeptide of SEQ ID NO: 3, and wherein said variant has alpha-amylase activity.

5. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 4, and wherein said variant has alpha-amylase activity.

6. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has e.g. at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 5, and wherein said variant has alpha-amylase activity.

7. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 6, and wherein said variant has alpha-amylase activity.

8. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 7, and wherein said variant has alpha-amylase activity.

9. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 8, and wherein said variant has alpha-amylase activity.

10. The alpha-amylase variant of paragraph 1, wherein said variant of a parent alpha-amylase comprises a) a deletion and/or a substitution at two or three or four positions corresponding to positions R181, G182, H183 and G184, and b) a alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 9, and wherein said variant has alpha-amylase activity.

11. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 10, and wherein said variant has alpha-amylase activity.

12. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297,299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 11, and wherein said variant has alpha-amylase activity.

13. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142,144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 12, and wherein said variant has alpha-amylase activity.

14. The alpha-amylase variant of paragraph 1, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NO: 13, and wherein said variant has alpha-amylase activity.

15. The alpha-amylase variant according to paragraph 1, which has an improved property relative to the parent alpha-amylase, wherein the improved property is selected from the group consisting of increased catalytic efficiency, increased catalytic rate, increased chemical stability, increased oxidation stability, increased pH activity, increased pH stability, increased specific activity, increased stability under storage conditions, increased substrate binding, increased substrate cleavage, increased substrate specificity, increased substrate stability, increased surface properties, increased thermal activity, and increased thermostability.

16. The alpha-amylase variant according to any one of the preceding paragraphs, wherein said variant of a parent alpha-amylase comprises a) a deletion and/or a substitution at two or three or four positions corresponding to positions R181, G182, H183 and G184, and b) an alteration at one or more positions corresponding to position: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, and 485, using SEQ ID NO: 1 for numbering; and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NOs: 1-13, and wherein said variant has alpha-amylase activity and wherein said variant has Improvement Factor (IF)>1.0 for a measure of wash performance when compared to said parent alpha-amylase having alpha-amylase activity as shown in SEQ ID NO: 1 and/or SEQ ID NO: 2.

17. The alpha-amylase variant according to any one of the preceding paragraphs, wherein said alteration in one or more positions corresponding to positions H1, H2, N3, G4, T5, M9, Y16, L17, N22, H23, N25, N28, S29, D30, A31, S32, N33, K35, S36, K37, T40, T40N, V42, 144, W48, A51, N54, V56, A60, D62, N70, V75, R82, S83, Q84, Q86, A87, V89, T90, S91, K93, N94, N95, Q98, M105, G109, A113, M116, R118, N125, N128, E130, V131, T132, E134, Y135, T136, E138, W140, R142, D144, N150, T151, H152, S154, F155, R158, Y160, V165, W167, Q169, R172, N174, N175, Y178, A186, E190, D192, T193, N195, I206, M208, E212, V214, L217, R218, N219, V222, T225, T227, L228, G229, F233, 1235, Y243, T246, R247, 1250, N251, H252, V253, S255, A256, N260, M261, A263, A265, F267, K269, I275, E276, Q280, K281, T282, W284, N285, H286, V288, V291, N296, L297, N299, K302, S303, G304, N306, N311, 1312, F313, G315, V317, Q319, R320, H321, S323, H324, A325, F328, D330, S334, E337, E338, A339, F343, E345, E346, W347, L355, T356, E360, Q361, Y371, I374, P375, T376, H377, G378, V379, A381, M382, R383, S384, K385, D387, 1389, E391, Q394, K395, P400, H402, H407, P408, V410, I411, S420, K423, L429, 1430, T431, S437, R439, A442, L444, K445, N446, E449, T450, W451, Y452, I454, S459, D460, T461, V462, K463, G465, D467, W469, G470, E471, H473, V474, D476, G477, I481, Y482, Q484, and K485, using SEQ ID NO: 1 for numbering and wherein each alteration is independently a substitution, insertion, or deletion, and wherein said variant has at least 60%, e.g. at least 65%, e.g., at least 70%, at least 75%, at least 80%, at least 85%, at least 90%, at least 95%, at least 96%, at least 97%, at least 98%, or at least 99%, but less than 100% sequence identity to the polypeptide of SEQ ID NOs: 1-13, and wherein said variant has alpha-amylase activity and wherein said variant having an Improvement Factor (IF) of >1.0 for a measure of wash performance when compared to said parent alpha-amylase having alpha-amylase activity as shown in SEQ ID NO: 1 or SEQ ID NO: 2.

18. The alpha-amylase variant according to any one of the preceding paragraphs, wherein said variant comprises a) a deletion and/or a substitution at two or three or four positions corresponding to positions R181, G182, H183 and G184, and b) alterations at one or more of the following positions: H1A, H1*, H2*, N3D, N3A, G4N, G4A, T5L, M9L, M91, Y16N, L17M, L17V, N22Q, H23Q, N25R, N25K, N28R, N28Q, S29N, S29T, D30N, A31S, S32P, S32A, S32Q, N33Y, K35A, K35S, S36E, S36D, K37V, K37H, T40S, T40N, V421, 144T, W48Y, A51T, N54A, N54S, V56T, A60P, D62N, N70H, V751, R82K, S83N, S83G, Q84D, Q84E, Q86E, Q86K, A87S, A87R, V891, T90N, T90K, S91A, S91T, K93H, N94S, N94A, N95R, Q98N, M105I, G109A, A113Y, A113Q, M116D, M116N, R118N, R118T, R118Q, N125S, N125Q, N128Y, E130V, V131I, T132S, E134T, E134D, Y135H, T136L, T136N, E138K, E138Q, W140Y, R142G, R142K, R142H, D144N, D144H, N150T, N150S, T151Q, H152Y, S154N, S154D, F155W, R158Q, R158Y, Y160F, V165T, W167F, Q169E, R172S, N174*, N174S, N175S, Y178F, A186G, E190P, D192S, T193S, N195F, I206L, I206Y, M208Y, E212D, V214I, V214A, L217I, L217M, R218K, R218N, N219K, N219R, V222T, T225A, T227E, L228V, G229Q, F233Y, I235L, Y243F, T246M, T246L, R247K, I250L, I250V, N251D, N251G, H252N, V253A, S255E, S255G, S255A, A256Q, A256K, N260E, N260G, M261L, A263T, A265G, F267Y, K269Q, I275L, E276N, Q280A, Q280N, Q280T, K281Y, K281F, T282V, W284Y, W284F, N285T, H286Q, H286M, V288L, V288A, V291A, N296Q, L297F, N299A, N299S, K302N, K302T, S303G, G304S, N306Y, N311K, N311Q, I312L, F313L, G315N, V317L, Q319A, Q319S, R320S, R320K, H321N, S323L, S323T, S323M, H324K, A325S, F328L, D330E, S334T, E337G, E338Q, A339S, F343T, E345Q, E346T, E346P, W347R, L355F, L355T, T356I, E360S, Q361G, Q361S, Y371M, 1374T, P375T, P375S, T376S, T376Q, H377R, H377D, G378E, V379I, A381S, M382Y, M382L, R383K, S384Q, S384H, K385Q, D387E, I389L, E391A, E391K, Q394K, K395Q, K395D, P400R, P400A, P400T, H402R, H407N, P408H, P408Q, V410I, I411V, S420A, S420T, K423N, K423G, L429V, 1430M, T431S, S437A, R439T, A442V, L444A, L444T, L444R, K445Q, K445S, K445A, N446H, E449Q, T450V, T450I, W451F, Y452K, Y452H, I454L, S459T, D460E, T461P, T461K, V462I, K463T, K463V, G465N, D467A, D467E, W469Y, W469N, W469T, G470A, E471T, H473P, H473R, V474C, D476K, G477E, I481V, Y482W, Q484K, K485R, and K485Q, using SEQ ID NO: 1 for numbering 19. The alpha-amylase variant according to any one of the preceding paragraphs, wherein the different amino acid residue is selected from the group consisting of A, C, D, E, F, G, H, I, K, L, M, N, P, Q, R, S, T, V, W, and Y, with the proviso that the different amino acid residue is different from the naturally-occurring amino acid residue.

20. The variant according to any one of the preceding paragraphs, wherein said variant has an Improvement Factor (IF) of at least 1.1, at least 1.2, at least 1.3, at least 1.4, at least 1.5, at least 1.6, at least 1.7, at least 1.8, at least 1.9, at least 2.0, at least 2.2, at least 2.4, at least 2.6, at least 2.8, at least 3.0, at least 3.2, at least 3.4, at least 3.6, at least 3.8, or at least 4.0 for a measure of wash performance when compared to said parent alpha-amylase as shown in SEQ ID NO: 1 and/or SEQ ID NO: 2.

21. The variant according to any one of the preceding paragraphs, wherein said variant has an Improvement Factor (IF) of at least 1.1, at least 1.2, at least 1.3, at least 1.4, at least 1.5, at least 1.6, at least 1.7, at least 1.8, at least 1.9, at least 2.0, at least 2.2, at least 2.4, at least 2.6, at least 2.8, at least 3.0, at least 3.2, at least 3.4, at least 3.6, at least 3.8, or at least 4.0 for a measure of wash performance in Model A detergent composition when compared to said parent alpha-amylase as shown in SEQ ID NO: 1 and/or SEQ ID NO: 2.

22. The variant according to any one of the preceding paragraphs, wherein said variant has an Improvement Factor (IF) of at least 1.1, at least 1.2, at least 1.3, at least 1.4, at least 1.5, at least 1.6, at least 1.7, at least 1.8, at least 1.9, at least 2.0, at least 2.2, at least 2.4, at least 2.6, at least 2.8, at least 3.0, at least 3.2, at least 3.4, at least 3.6, at least 3.8, or at least 4.0 for a measure of wash performance in Model J detergent composition when compared to said parent alpha-amylase as shown in SEQ ID NO: 1 and/or SEQ ID NO: 2.

23. The variant according to any one of the preceding paragraphs, wherein said variant has an Improvement Factor (IF) of at least 1.1, at least 1.2, at least 1.3, at least 1.4, at least 1.5, at least 1.6, at least 1.7, at least 1.8, at least 1.9, at least 2.0, at least 2.2, at least 2.4, at least 2.6, at least 2.8, at least 3.0, at least 3.2, at least 3.4, at least 3.6, at least 3.8, or at least 4.0 for a measure of wash performance in Model A and Model J detergent composition when compared to said parent alpha-amylase as shown in SEQ ID NO: 1 and/or SEQ ID NO: 2.

24. The variant according to any one of the preceding paragraphs, wherein said variant is selected from the group consisting of:

I. T5L+N33Y+K35A+S36E+K37H+N95R+G109A+H183*+G184*+E190P+Q280N+W284F+N296Q+L297F+N311K+I312L+F313L+Q319S+R320K+H324K+S334T+L355F+T356I+Q361S+Y371M+R383K+S384H+D387E+E391K+Q394K+K395Q+P400A;

II. M105I+G109A+V131I+Y135H+Q169E+N174*+H183*+G184*+I206Y+M208Y+L217I+I235L+T246L+I250V+A263T+F343T+E346T+I374T+V379I+M382L+V410I+K423N+S437A+A442V+L444A+Y452H+D460E+T461P+K463V+G465N+D467E+K485R;

III. N22Q+N25R+N28Q+S29N+A51T+N54A+N70H+R82K+S83G+Q84E+V89I+T90K+K93H+Q98N+M116D+R118T+E130V+T136L+E138K+R142H+D144H+N150S+H152Y+S154D+R158Y+R181Q+H183*+G184*+E190P+T225A+T227E+G229Q+T356I+Q361S;

IV. A51T+N54A+Q98N+G109A+M116D+R118Q+E130V+T136L+E138K+R142H+D144H+S154D+R158Y+N174*+R181Q+H183*+G184*+E190P+I206L+E212D+V214A+R218K+N219R+V222T+T225A+S255E+A256K+W284F+N311K+R320K+H324K+S334T+T356I+Q361S+V410I+R439T+W469N+E471T;

V. N22Q+N25K+N28Q+S29N+A51T+N54A+N70H+Q84D+V89I+T90K+K93H+Q98N+M116D+R118Q+E130V+V131I+T136L+E138K+N174*+R181Q+H183*+G184*+I206L+G229Q+Q319S+R320K+F343T+E346T+I374T+V379I+M382L+R383K+P400A+K423N+L444A+K463V;

VI. A51T+N54A+G109A+R118T+E134D+W140Y+R172S+H183*+G184* E190P+I206L+Y243F+F267Y+Q280N+K281 F+N299A+K302N+R320K+S334T+A339S+V410I+E471T+D476K;

VII. K35A+A51T+N54A+G109A+R118T+W140Y+R172S+N174*+R181Q+H183*+G184*+E190P+I206L+I235L+Y243F+F267Y+Q280N+K281F+N299A+K302T+R320K+S334T+A339S+E345Q+E346P+V410I;

VIII. H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471T+D476K;

IX. K35A+A51T+N54A+D62N+M105I+G109A+R118T+V131I+Y135H+W140Y+Q169E+R172S+N174*+H183*+G184*+E190P+I206L+M208Y+L217I+I235L+Y243F+T246L+1250V+A263T+F267Y+Q280N+K281 F+N299A+K302T+F343T+E346T+I374T+V379I+M382L+V410I+K423N+

S437A+A442V+L444A+Y452H+D460E+T461P+K463V+G465N+D467E+E471T+D476K+K485R;

X. N22Q+N25R+N28Q+S29N+A51 T+N54A+N70H+R82K+S83G+Q84E+V89I+T90K+K93H+Q98N+G109A+M116D+R118T+E130V+T136L+E138K+W140Y+R142H+D144H+N150S+H152Y+S154D+R158Y+R172S+N174*+R181Q+H183*+G184*+E190P+I206L+Y243F+F267Y+Q280N+K281 F+N299A+K302N+R320K+S334T+A339S+E345Q+E346P+T356I+Q361 S+V410I+E471 T+D476K;

XI. A51T+N54A+Q98N+G109A+M116D+R118Q+E130V+T136L+E138K+W140Y+R142H+D144H+S154D+R158Y+N174*+R181Q+H183*+G184*+E190P+I206L+E212D+V214A+R218K+N219R+V222T+T225A+S255E+A256K+Q280N+W284F+K302N+N311K+R320K+H324K+S334T+T356I+Q361 S+V410I+R439T+W469N+E471T+D476K;

XII. N22Q+N25K+N28Q+S29N+K35A+A51 T+N54A+N70H+Q84D+V89I+T90K+K93H+Q98N+G109A+M116D+R118Q+E130V+V131I+T136L+E138K+W167F+R172S+R181 Q+H183*+G184*+I206L+G229Q+I235L+Y243F+F267Y+Q280N+K281 F+N299A+K302N+Q319S+R320K+S334T+A339S+F343T+E345Q+E346T+I374T+V379I+M382L+R383K+P400A+V410I+K423N+L444A+K463V+E471T+D476K;

XIII. N174S+H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471 T+D476K;

XIV. H1A+N3A+K35A+A51T+N54A+G109A+R118T+W140Y+R172S+N174S+R181Q+H183*+G184*+E190P+I206L+I235L+Y243F+F267Y+Q280N+K281 F+N299A+K302T+R320K+S334T+A339S+E345Q+E346P+P408H+V410I+I411V+K423N+S437A+A442V+L444R+K445Q+Y452H+D460E+T461P+K463V+G465N+D467E+D476K+K485R;

XV. H1A+N3A+G4N+T5L+M9L+L17M+N22Q+N25R+N28Q+S29N+A31S+S32A+N33Y+K35A+S36E+K37H+W48Y+A51T+N54A+M105I+G109A+R118T+E134D+W140Y+R172S+N174S+H183*+G184*+E190P+I206L+Y243F+F267Y+Q280N+W284F+N299A+K302N+Q319S+R320K+S323L+H324K+A325S+S334T+A339S+V379I+M382L+V410I+E471T+D476K;

XVI. H1A+N3A+A51T+N54A+G109A+R118T+E134D+W140Y+R172S+N174S+H183*+G184*+E190P+I206L+Y243F+F267Y+Q280N+K281 F+N299A+K302N+R320K+S334T+A339S+V410I+I411V+K423N+S437A+A442V+L444R+K445Q+Y452H+D460E+T461P+K463V+G465N+D467E+D476K+K485R;

XVII. H1A+N3A+M9L+K35A+W48Y+A51T+N54A+M105I+G109A+R118T+W140Y+R172S+N174*+R181Q+H183*+G184*+E190P+I206L+I235L+Y243F+T246L+F267Y+Q280N+K281F+N299A+K302T+R320K+S334T+A339S+E345Q+E346P+V379I+M382L+V410I+D476K;

XVIII. N174S+H183*+G184*+N311K+I312L+F313L+Q319S+R320K+H324K+S334T+E345Q+E346P+L355F+T356I+Q361S+Y371M+V379I+R383K+S384H+D387E+E391K+Q394K+K395Q+P400A+P408H+V410I+I411V+K423N+S437A+A442V+L444R+K445Q+Y452H+D460E+T461P+K463V+G465N+D467E+D476K+K485R;

XIX. H1*+N28R+S36D+T40S+A51T+N54A+V75I+S83N+T90N+S91A+N94S+G109A+R118N+T132S+E134D+W140Y+R142K+S154N+R172S+H183*+G184*+A186G+E190P+N1 95F+I206L+Y243F+F267Y+Q280N+K281 F+N299S+K302N+N311 Q+R320K+S323M+S334T+A339S+T356I+Q361S+R383K+P400R+P408H+V410I+I411V+K423N+S437A+A442V+L444R+K445Q+Y452H+D460E+T461P+K463V+G465N+D467E+E471T+D476K+K485R;

XX. N174S+H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471 T+D476K;

XXI. N174S+H183*+G184*+N311K+I312L+F313L+Q319S+R320K+H324K+S334T+E345Q+E346P+L355F+T356I+Q361S+Y371M+R383K+S384H+D387E+E391K+Q394K+K395Q+P400A+P408H+V410I+I411V+K423N+S437A+A442V+L444R+K445Q+Y452H+D460E+T461P+K463V+G465N+D467E+D476K+K485R;

XXII. H1*+N3A+M9L+K35A+W48Y+A51T+N54A+M105I+G109A+R118T+W140Y+R172S+N174*+R181Q+H183*+G184*+E190P+I206L+I235L+Y243F+T246L+F267Y+Q280N+K281F+N299A+K302T+R320K+S334T+A339S+E345Q+E346P+T356I+Q361S+V379I+M382L+V410I+D476K;

XXIII. H1*+N3A+K35A+A51T+N54A+G109A+R118T+W140Y+R172S+N174S+R181Q+H183*+G184*+E190P+I206L+I235L+Y243F+F267Y+Q280N+K281 F+N299A+K302T+R320K+S334T+A339S+E345Q+E346P+T356I+Q361S+P408H+V410I+I411V+K423N+S437A+A442V+L444R+K445Q+Y452H+D460E+T461P+K463V+G465N+D467E+D476K+K485R;

XXIV. H1*+N3A+K35A+A51T+N54A+G109A+R118T+W140Y+R172S+N174S+R181Q+H183*+G184*+E190P+I206L+I235L+Y243F+F267Y+Q280N+K281F+N299A+K302T+R320K+S334T+A339S+E345Q+E346P+T356I+Q361S+P408H+V410I+I411V+K423N+S437A+A442V+L444R+K445Q+Y452H+D460E+T461P+K463V+G465N+D467E+D476K+K485R;

XXV. H1*+N3A+A51T+N54A+G109A+R118T+E134D+W140Y+R172S+N174S+H183*+G184*+E190P+I206L+Y243F+F267Y+Q280N+K281 F+N299A+K302N+R320K+S334T+A339S+V410I+I411V+K423N+S437A+A442V+L444R+K445Q+Y452H+D460E+T461P+K463V+G465N+D467E+D476K+K485R;

XXVI. R118N+N174S+H183*+G184*+E190P+I206L+Y243F+F267Y+K281F+N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471T+D476K;

XXVII. R118Q+N174S+H183*+G184*+E190P+I206L+Y243F+F267Y+K281F+N311K+I312L+F313L+Q319S+R320K+H324K+S334T+E345Q+E346P+L355F+T356I+Q361S+Y371M+R383K+S384H+D387E+E391K+Q394K+K395Q+P400A+P408H+V410I+I411V+K423N+S437A+A442V+L444R+K445Q+Y452H+D460E+T461P+K463V+G465N+D467E+D476K+K485R;

XXVIII. H1*+N3A+M9L+K35A+W48Y+A51T+N54A+M105I+G109A+R118Q+W140Y+R172S+N174*+R181Q+H183*+G184*+E190P+I206L+V214I+I235L+Y243F+T246L+F267Y+Q280N+K281F+N299A+K302T+R320K+S334T+A339S+E345Q+E346P+V379I+M382L+V410I+D476K+K485R;

XXIX. H1*+H2*+N3A+G4A+L17V+N22Q+H23Q+N28R+S29T+S32P+N33Y+K35S+K37V+T40N+I44T+W48Y+A51T+N54A+A60P+R82K+S83G+Q84E+Q86K+A87S+T90N+S91T+K93H+N94S+G109A+A113Y+M116N+R118T+N125S+N128Y+V131I+T132S+T136N+E138Q+R142G+D144N+N150T+H152Y+S154N+F155W+R158Q+Y160F+V165T+R172S+N174*+N175S+Y178F+R181D+H183*+G184*+E190P+D192S+T193S+I206Y+M208Y+E212D+L217M+R218K+N219K+T225A+T227E+L228V+F233Y+1235L+Y243F+T246L+R247K+I250V+N251 D+H252N+V253A+S255A+N260E+A263T+A265G+F267Y+K269Q+I275L+E276N+Q280A+T282V+W284Y+H286Q+V288L+V291A+L297F+N299A+K302T+S303G+N306Y+F313L+G315N+V317L+Q319A+R320S+H321N+S323T+H324K+F328L+D330E+S334T+E337G+E338Q+A339S+F343T+E345Q+E346P+W347R+L355F+T356I+E360S+Q361G+Y371M+*372aG+*372bT+*372cK+I374T+P375T+H377R+G378E+V379I+M382L+R383K+D387E+I389L+E391K+Q394K+K395D+P400T+H402R+H407N+S420T+L429V+A442V+L444T+K445S+T450I+I454L+S459T+T461K+V462I+K463T+W469Y+G470A+E471T+H473P+D476K+G477E+I481V+Y482W+K485Q;

XXX. H1*+N3D+T5L+M9I+Y16N+L17V+N22Q+N25R+N28Q+S29N+D30N+S32Q+N33Y+K35A+S36E+K37H+V42I+A51T+N54A+V56T+N70H+R82K+S83G+Q84E+Q86E+A87R+V89I+T90K+K93H+N94A+N95R+Q98N+G109A+A113Q+M116D+R118N+N125Q+E130V+T132S+E134T+T136L+E138K+W140Y+R142H+D144H+N150S+T151Q+H152Y+S154D+R158Y+V165T+R172S+N174*+R181Q+G182T+H183*+G184*+E190P+N195F+I206L+V214I+R218N+N219R+T225A+T227E+G229Q+I235L+Y243F+T246M+I250L+N251G+S255G+A256Q+M261L+F267Y+I275L+Q280N+K281 F+N285T+H286M+V288A+N299S+K302N+G304S+I312L+F313L+V317L+R320K+S334T+E337G+A339S+E345Q+E346P+L355T+T356I+Q361S+Y371M+I374T+P375S+T376Q+H377R+G378E+A381S+M382Y+S384Q+K385Q+I389L+E391A+K395Q+P400A+H407N+P408Q+V410I+S420A+K423G+L429V+I430M+T431 S+R439T+A442V+L444T+K445A+N446H+E449Q+T450V+W451 F+Y452K+S459T+K463T+G465N+D467A+W469T+E471T+H473R+V474C+D476K+Y482W+Q484K+K485Q;

XXXI. H1A+H2*+N3A+M9L+K35A+W48Y+A51T+N54A+M105I+G109A+R118T+W140Y+R172S+R181Q+E188P+I204L+I233L+Y241F+T244L+F265Y+Q278N+K279F+N297A+K300T+R318K+S332T+A337S+E343Q+E344P+V377I+M380L+V408I+D474K;

XXXII. H1*+H2*+N3A+M9L+K35A+W48Y+A51T+N54A+M105I+G109A+R118Q+W140Y+R172S+R181Q+E188P+I204L+V212I+I233L+Y241F+T244L+F265Y+Q278N+K279F+N297A+K300T+R318K+S332T+A337S+E343Q+E344P+V377I+M380L+V408I+D474K;

XXXIII. H1*+N3D+T5L+M9I+Y16N+L17V+N22Q+N25R+N28Q+S29N+D30N+S32Q+N33Y+K35A+S36E+K37H+V42I+A51T+N54A+V56T+N70H+R82K+S83G+Q84E+Q86E+A87R+V89I+T90K+K93H+N94A+N95R+Q98N+G109A+A113Q+M116D+R118N+N125Q+E130V+T132S+E134T+T136L+E138K+W140Y+R142H+D144H+N150S+T151Q+H152Y+S154D+R158Y+V165T+R172S+N174*+R181Q+H183*+G184*+G184T+E190P+N195F+I206L+V214I+R218N+N219R+T225A+T227E+G229Q+I235L+Y243F+T246M+I250L+N251G+S255G+A256Q+M261L+F267Y+I275L+Q280N+K281 F+N285T+H286M+V288A+N299S+K302N+G304S+I312L+F313L+V317L+R320K+S334T+E337G+A339S+E345Q+E346P+L355T+T356I+Q361S+T376S+H377D+A381S+M382Y+S384Q+K385Q+I389L+E391A+K395Q+P400A+H407N+P408Q+V410I+S420A+K423G+L429V+I430M+T431S+R439T+A442V+L444T+K445A+N446H+E449Q+T450V+W451 F+Y452K+D460E+T461P+K463V+G465N+D467A+W469T+E471T+H473R+V474C+D476K+Y482W+Q484K+K485Q;

XXXIV. H1*+N3D+M9L+K35A+W48Y+A51T+N54S+R82K+V89I+M105I+G109A+R118N+W140Y+H152Y+V165T+R172S+N174*+R181Q+H183*+G184*+E190P+I206Y+M208Y+E212D+V214I+L217I+T227E+I235L+Y243F+T246L+N260G+F267Y+I275L+Q280T+K281Y+N299A+K302T+R320K+A325S+S334T+A339S+F343T+E345Q+E346P+T356I+V379I+M382L+R383K+V410I+I430M+D476K, using SEQ ID NO: 1 for numbering.

25. The alpha-amylase variant according to any one of the preceding paragraphs, wherein the parent alpha amylase has at least 60%, e.g., at least 62%, at least 63%, at least 65%, at least 70%, at least 75%, at least 80%, at least 85%, at least 90%, at least 95%, at least 96%, at least 97%, at least 98%, at least 99% but less than 100% sequence identity to the polypeptide of SEQ ID NO: 1, 2, 3, 4, 5, 6, 7, 8, 9, 10, 11, 12 or 13.

26. The alpha-amylase variant according to any one of the preceding paragraphs, wherein said parent alpha amylase comprises or consists of the polypeptide of SEQ ID NO: 1 or SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 or SEQ ID NO: 13.

27. The alpha-amylase variant according to any one of the preceding paragraphs, which has at least 60%, e.g., at least 65%, at least 70%, at least 75%, at least 80%, at least 85%, at least 90%, at least 95% identity, at least 96%, at least 97%, at least 98%, or at least 99%, but less than 100% sequence identity to the amino acid sequence of the parent alpha amylase.

28. The alpha-amylase variant according to any one of the preceding paragraphs, wherein said variant comprises a substitution and/or deletion at 1, 2, 3, 4, 5, 6, 7, 8, 9, or 10 positions.

29. An isolated polynucleotide encoding the variant according to any one of the preceding paragraphs.

30. A nucleic acid construct comprising the polynucleotide according to paragraph 29.

31. An expression vector comprising the polynucleotide according to paragraph 29.

32. A recombinant host cell transformed with the polynucleotide of paragraph 29.
33. A host cell comprising the polynucleotide according to paragraph 29, the nucleic acid construct according to paragraph 30, or the expression vector according to paragraph 31.
34. A method of producing an alpha-amylase variant, comprising: a. cultivating the host cell of paragraph 32 under conditions suitable for expression of said variant; and b. recovering said variant.
35. A detergent composition comprising the variant according to any one of the paragraphs 1 to 28.
36. The composition according to paragraph 35, further comprising at least one detergent component.
37. The composition according to paragraph 36, wherein said detergent component is selected from the group consisting of surfactants, builders, flocculating aid, chelating agents, dye transfer inhibitors, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.
38. The composition according to any one of the paragraphs 35 to 37 wherein the detergent component further comprises one or more additional enzymes.
39. The composition according to any one of the paragraphs 35-38, wherein the additional enzyme is selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, licheninases laminarinases, DNAses, or any combinations thereof.
40. The composition according to any one of the paragraphs 35-39, wherein the detergent composition is selected from a group comprising: liquid detergents, solid detergents, gel detergents, powder detergents and granule detergents.
41. The composition according to any one of the paragraphs 35-40, wherein the composition is a liquid laundry or liquid dish wash composition, such as an Automatic Dish Wash (ADW) liquid detergent composition, or a powder laundry, such as a soap bar, or powder dish wash composition, such as an ADW unit dose detergent composition and such as a Hand Dish Wash (HDW) detergent composition.
42. Use of a composition according to any one of the paragraphs 35-41 in a cleaning process such as for laundering, washing, cleaning and/or deep cleaning of a textile and/or a hard surface (such as dish wash).
43. Use of a variant according to any one of the paragraphs 1 to 28 in a cleaning process such as laundry or hard surface cleaning including dishwash and industrial cleaning.
44. A method of obtaining an alpha-amylase variant of a parent alpha-amylase comprising the steps of: a) introducing a deletion and/or a substitution at two orthree or four positions corresponding to positions R181, G182, H183 and G184, and b) introducing an alteration at one or more positions corresponding to positions: 1, 2, 3, 4, 5, 9, 16, 17, 22, 23, 25, 28, 29, 30, 31, 32, 33, 35, 36, 37, 40, 42, 44, 48, 51, 54, 56, 60, 62, 70, 75, 82, 83, 84, 86, 87, 89, 90, 91, 93, 94, 95, 98, 105, 109, 113, 116, 118, 125, 128, 130, 131, 132, 134, 135, 136, 138, 140, 142, 144, 150, 151, 152, 154, 155, 158, 160, 165, 167, 169, 172, 174, 178, 186, 190, 192, 193, 195, 206, 208, 212, 214, 217, 218, 219, 222, 225, 227, 228, 229, 233, 235, 243, 246, 247, 250, 251, 252, 253, 255, 256, 260, 261, 263, 265, 267, 269, 275, 276, 280, 281, 282, 284, 285, 286, 288, 291, 296, 297, 299, 302, 303, 304, 306, 311, 312, 313, 315, 317, 319, 320, 321, 323, 324, 325, 328, 330, 334, 337, 338, 339, 343, 345, 346, 347, 355, 356, 360, 361, 371, 374, 375, 376, 377, 378, 379, 381, 382, 383, 384, 385, 387, 389, 391, 394, 395, 400, 402, 407, 408, 410, 411, 420, 423, 429, 430, 431, 437, 439, 442, 444, 445, 446, 449, 450, 451, 452, 454, 459, 460, 461, 463, 465, 467, 469, 470, 471, 473, 476, 477, 481, 482, 485, using SEQ ID NO: 1 for numbering; said method thereby providing an alpha-amylase variant of said parent alpha-amylase, wherein said variant has at least 60%, such as at least 65%, such as at least 70%, such as at least 75%, such as at least 80%,such as at least 85%, such as at least 90%, such as at least 95%, such as at least 97%, such as at least 99%, but less than 100% sequence identity to the amino acid sequence to the polypeptide of SEQ ID NOs: 1-13.
45. A method of treating a surface, comprising
    a. forming an aqueous wash liquor comprising water, the amylase described herein and a cleaning adjunct,
    b. treating the surface with the aqueous wash liquor preferably at a temperature in the range of 5-60° C.; and
    c. rinsing the surface.

Materials and Method

Assays for Alpha-Amylase Activity pNP-G7 assay

The alpha-amylase activity may be determined by a method employing the G7-pNP substrate. G7-pNP which is an abbreviation for 4,6-ethylidene($G_7$)-p-nitrophenyl($G_1$)-alpha,D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at Q=405 nm (400-420 nm.). Kits containing G7-pNP substrate and alpha-Glucosidase is manufactured by Roche/Hitachi (cat. No. 11876473).

Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether ($C_{14}H_{22}O(C_2H_4O)_n$ (n=9-10))), 1 mM $CaCl_2$, pH8.0.

Procedure:

The amylase sample to be analyzed is diluted in dilution buffer to ensure the pH in the diluted sample is 7. The assay is performed by transferring 20 μl diluted enzyme samples to 96 well microtiter plate and adding 80 μl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Phadebas Activity Assay:

The alpha-amylase activity can also be determined by a method using the Phadebas substrate (from for example Magle Life Sciences, Lund, Sweden). A Phadebas tablet includes interlinked starch polymers that are in the form of globular microspheres that are insoluble in water. A blue dye is covalently bound to these microspheres. The interlinked starch polymers in the microsphere are degraded at a speed that is proportional to the alpha-amylase activity. When the alpha-amylase degrades the starch polymers, the released blue dye is water soluble and concentration of dye can be determined by measuring absorbance at 620 nm. The concentration of blue is proportional to the alpha-amylase activity in the sample. The amylase sample to be analysed is diluted in activity buffer with the desired pH. One substrate tablet is suspended in 5 mL activity buffer and mixed on magnetic stirrer. During mixing of substrate transfer 150 μl to microtiter plate (MTP) or PCR-MTP. Add 30 μl diluted amylase sample to 150 μl substrate and mix. Incubate for 15 minutes at 37° C. The reaction is stopped by adding 30 μl 1M NaOH and mix. Centrifuge MTP for 5 minutes at 4000×g. Transfer 100 μl to new MTP and measure absorbance at 620 nm. The amylase sample should be diluted so that the absorbance at 620 nm is between 0 and 2.2 and is within the linear range of the activity assay.

Reducing Sugar Activity Assay:

The alpha-amylase activity can also be determined by reducing sugar assay with for example corn starch substrate. The number of reducing ends formed by the alpha-amylase hydrolysing the alpha-1,4-glycosidic linkages in starch is determined by reaction with p-Hydroxybenzoic acid hydrazide (PHBAH). After reaction with PHBAH the number of reducing ends can be measured by absorbance at 405 nm and the concentration of reducing ends is proportional to the alpha-amylase activity in the sample. The corns starch substrate (3 mg/ml) is solubilised by cooking for 5 minutes in milliQ water and cooled down before assay. For the stop solution prepare a Ka-Na-tartrate/NaOH solution (K—Na-tartrate (Merck 8087) 50 g/I, NaOH 20 g/I) and prepare freshly the stop solution by adding p-Hydroxybenzoic acid hydrazide (PHBAH, Sigma H9882) to Ka-Na-tartrate/NaOH solution to 15 mg/ml.

In PCR-MTP$^{50}$ μl activity buffer is mixed with 50 μl substrate. Add 50 μl diluted enzyme and mix. Incubate at the desired temperature in PCR machine for 5 minutes. Reaction is stopped by adding 75 μl stop solution (Ka-Na-tartrate/NaOH/PHBAH). Incubate in PCR machine for 10 minutes at 95° C. Transfer 150 μl to new MTP and measure absorbance at 405 nm. The amylase sample should be diluted so that the absorbance at 405 nm is between 0 and 2.2, and is within the linear range of the activity assay.

EnzChek® assay:

For the determination of residual amylase activity an EnzChek® Ultra Amylase Assay Kit (E33651, Invitrogen, La Jolla, CA, USA) may be used.

The substrate is a corn starch derivative, DQ™ starch, which is corn starch labeled with BODIPY® FL dye to such a degree that fluorescence is quenched. One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.125 mM $CaCl_2$, pH 5.5 is added, vortexed thoroughly and stored at room temperature, in the dark until ready to use. The stock substrate working solution is prepared by diluting 10-fold in residual activity buffer (100 mM acetate, 0.01% (w/v) TRITON® X100, 0.125 mM $CaCl_2$, pH 5.5). Immediately after incubation the enzyme is diluted to a concentration of 10-20 ng enzyme protein/ml in 100 mM acetate, 0.01% (W/v) TRITON® X100, 0.125 mM $CaCl_2$, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the Vmax is calculated as the slope of the plot of fluorescence intensity against time. The plot should be linear and the residual activity assay has been adjusted so that the diluted reference enzyme solution is within the linear range of the activity assay.

Wash Performance of Alpha Amylase's Using Automatic Mechanical Stress Assay

In order to assess the wash performance of the alpha-amylases in a detergent base composition, washing experiments may be performed using Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch/melamine plate to be washed against all the slot openings. During the washing time, the plate, test solutions, textile/melamine plate and lid are vigorously shaken to bring the test solution in contact with the textile/melamine plate and apply mechanical stress in a regular, periodic oscillating manner. For further description see WO 02/42740, especially the paragraph "Special method embodiments" at page 23-24.

General Laundry Wash Performance Description

A test solution comprising water (6° dH), 0.79 g/L detergent, e.g. model detergent J as described below, and the enzyme of the invention at concentration of 0.9 mg enzyme protein/L, is prepared. Fabrics stained with starch (CS-28 from Center For Test materials BV, P.O. Box 120, 3133 KT, Vlaardingen, The Netherlands) is added and washed for 20 minutes at 15° C. and/or 30° C., or alternatively 20 minutes at 15° C. and/or 40° C. as specified in the examples. After thorough rinse under running tap water and drying in the dark, the light intensity values of the stained fabrics are subsequently measured as a measure for wash performance. The test with 0 mg enzyme protein/L is used as a blank and corresponds to the contribution from the detergent. Preferably mechanical action is applied during the wash step, e.g. in the form of shaking, rotating or stirring the wash solution with the fabrics. The AMSA wash performance experiments were conducted under the experimental conditions specified below:

TABLE A

| Experimental condition | |
|---|---|
| Detergent | Liquid Model detergent J (see Table B) |
| Detergent dosage | 0.79 g/L |
| Test solution volume | 160 micro L |
| pH | As is |
| Wash time | 20 minutes |
| Temperature | 20° C. |
| Water hardness | 6°dH |
| Enzyme concentration in test | 0.09 mg enzyme protein/L |
| Test material | CS-28 (Rice starch cotton) |

TABLE B

| Model detergent J | | |
|---|---|---|
| Compound | Content of compound (% w/w) | % active component (% w/w) |
| LAS | 5.15 | 5.00 |
| AS | 5.00 | 4.50 |
| AEOS | 14.18 | 10.00 |
| Coco fatty acid | 1.00 | 1.00 |
| AEO | 5.00 | 5.00 |
| MEA | 0.30 | 0.30 |
| MPG | 3.00 | 3.00 |
| Ethanol | 1.50 | 1.35 |
| DTPA (as Na5 salt) | 0.25 | 0.10 |
| Sodium citrate | 4.00 | 4.00 |
| Sodium formate | 1.00 | 1.00 |
| Sodium hydroxide | 0.66 | 0.66 |
| $H_2O$, ion exchanged | 58.95 | 58.95 |

Water hardness was adjusted to 6°dH by addition of CaCl2, MgCl2, and NaHCO3 ($Ca^{2+}$:$Mg^{2+}$:$HCO3^-$ = 2:1:4.5) to the test system. After washing the textiles were flushed in tap water and dried.

TABLE C

| Experimental condition | |
|---|---|
| Detergent | Liquid Model detergent A (see Table D) |
| Detergent dosage | 3.33 g/L |
| Test solution volume | 160 micro L |
| PH | As is |
| Wash time | 20 minutes |
| Temperature | 20° C. |
| Water hardness | 15°dH |
| Enzyme concentration in test | 0.2 mg enzyme protein/L |
| Test material | CS-28 (Rice starch cotton) |

TABLE D

| Model detergent A | | |
|---|---|---|
| Compound | Content of compound (% w/w) | % active component (% w/w) |
| LAS | 12.00 | 11.60 |
| AEOS, SLES | 17.63 | 4.90 |
| Soy fatty acid | 2.75 | 2.48 |
| Coco fatty acid | 2.75 | 2.80 |
| AEO | 11.00 | 11.00 |
| Sodium hydroxide | 1.75 | 1.80 |
| Ethanol/Propan-2-ol | 3.00 | 2.70/0.30 |
| MPG | 6.00 | 6.00 |
| Glycerol | 1.71 | 1.70 |
| TEA | 3.33 | 3.30 |
| Sodium formate | 1.00 | 1.00 |
| Sodium citrate | 2.00 | 2.00 |
| DTMPA | 0.48 | 0.20 |
| PCA | 0.46 | 0.18 |
| Phenoxy ethanol | 0.50 | 0.50 |
| $H_2O$, ion exchanged | 33.64 | 33.64 |

Water hardness was adjusted to 15□dH by addition of CaCl2, MgCl2, and NaHCO3 ($Ca^{2+}$:$Mg^{2+}$:$HCO3^-$ = 4:1:7.5) to the test system. After washing the textiles were flushed in tap water and dried.

Example 1: Construction of Variants by Site-Directed Mutagenesis

Site-directed variants were constructed of *Bacillus* sp alpha-amylase (SEQ ID NO: 1), comprising specific alterations according to the invention. The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence. Mutagenic oligos were designed corresponding to the DNA sequence flanking the desired site(s) of mutation, separated by the DNA base pairs defining the insertions/deletions/substitutions, and purchased from an oligo vendor such as Macrogen, Inc.

Example 2: Laundry Wash Performance of Alpha-Amylase Variants

The wash performance of alpha amylases according to the invention was tested under the conditions and in the model detergents, as described above. The alpha-amylase variants have improved was performance at 20° C. in model detergent A and Model J compared to the reference alpha-amylase having the amino acid sequence of SEQ ID NO: 2.

| Mutations in SEQ ID NO: 2 (using SEQ ID NO: 1 for numbering) | IF (Model J) | IF (Model A) |
|---|---|---|
| SEQ ID NO: 2 | 1.0 | 1.0 |
| K35A + A51T + N54A + G109A + R118T + W140Y + R172S + N174* + R181Q + E190P + I206L + I235L + Y243F + F267Y + Q280N + K281F + N299A + K302T + R320K + S334T + A339S + E345Q + E346P + V410I | 2.1 | 1.6 |
| N311K + I312L + F313L + Q319S + R320K + H324K + S334T + E345Q + E346P + L355F + T356I + Q361S + Y371M + R383K + S384H + D387E + E391K + Q394K + K395Q + P400A + V410I + E471T + D476K | 2.1 | 1.6 |
| N22Q + N25R + N28Q + S29N + A51T + N54A + N70H + R82K + S83G + Q84E + V89I + T90K + K93H + Q98N + G109A + M116D + R118T + E130V + T136L + E138K + W140Y + R142H + D144H + N150S + H152Y + S154D + R158Y + R172S + N174* + R181Q + | 2.0 | 1.5 |

-continued

| Mutations in SEQ ID NO: 2 (using SEQ ID NO: 1 for numbering) | IF (Model J) | IF (Model A) |
|---|---|---|
| E190P + I206L + Y243F + F267Y + Q280N + K281F + N299A + K302N + R320K + S334T + A339S + E345Q + E346P + T356I + Q361S + V410I + E471T + D476K | | |
| H1* + N3A + M9L + K35A + W48Y + A51T + N54A + M105I + G109A + R118Q + W140Y + R172S + N174* + R181Q + E190P + I206L + V214I + I235L + Y243F + T246L + F267Y + Q280N + K281F + N299A + K302T + R320K + S334T + A339S + E345Q + E346P + V379I + M382L + V410I + D476K + K485R | 1.9 | 1.6 |
| H1A + N3A + M9L + K35A + W48Y + A51T + N54A + M105I + G109A + R118T + W140Y + R172S + N174* + R181Q + E190P + I206L + I235L + Y243F + T246L + F267Y + Q280N + K281F + N299A + K302T + R320K + S334T + A339S + E345Q + E346P + V379I + M382L + V410I + D476K | 1.8 | 1.4 |
| A51T + N54A + G109A + R118T + E134D + W140Y + R172S + E190P + I206L + Y243F + F267Y + Q280N + K281F + N299A + K302N + R320K + S334T + A339S + V410I + E471T + D476K | 1.8 | 1.3 |
| N22Q + N25K + N28Q + S29N + K35A + A51T + N54A + N70H + Q84D + V89I + T90K + K93H + Q98N + G109A + M116D + R118Q + E130V + V131I + T136L + E138K + W167F + R172S + R181Q + I206L + G229Q + I235L + Y243F + F267Y + Q280N + K281F + N299A + K302N + Q319S + R320K + S334T + A339S + F343T + E345Q + E346T + I374T + V379I + M382L + R383K + P400A + V410I + K423N + L444A + K463V + E471T + D476K | 1.6 | 1.4 |
| H1A + N3A + A51T + N54A + G109A + R118T + E134D + W140Y + R172S + N174S + E190P + I206L + Y243F + F267Y + Q280N + K281F + N299A + K302N + R320K + S334T + A339S + V410I + I411V + K423N + S437A + A442V + L444R + K445Q + Y452H + D460E + T461P + K463V + G465N + D467E + D476K + K485R | 1.2 | 1.3 |
| H1* + N3A + A51T + N54A + G109A + R118T + E134D + W140Y + R172S + N174S + E190P + I206L + Y243F + F267Y + Q280N + K281F + N299A + K302N + R320K + S334T + A339S + V410I + I411V + K423N + S437A + A442V + L444R + K445Q + Y452H + D460E + T461P + K463V + G465N + D467E + D476K + K485R | 1.1 | 1.2 |
| H1A + N3A + K35A + A51T + N54A + G109A + R118T + W140Y + R172S + N174S + R181Q + E190P + I206L + I235L + Y243F + F267Y + Q280N + K281F + N299A + K302T + R320K + S334T + A339S + E345Q + E346P + P408H + V410I + I411V + K423N + S437A + A442V + L444R + K445Q + Y452H + D460E + T461P + K463V + G465N + D467E + D476K + K485R | — | 1.2 |
| H1A + H2* + N3A + M9L + K35A + W48Y + A51T + N54A + M105I + G109A + R118T + W140Y + R172S + R181Q + E188P + I204L + I233L + Y241F + T244L + F265Y + Q278N + K279F + N297A + K300T + R318K + S332T + A337S + E343Q + E344P + V377I + M380L + V408I + D474K | — | 1.4 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An alpha-amylase variant of a parent alpha-amylase comprising a) a deletion at two or three or four positions corresponding to positions R181, G182, H183 and G184, and b) a set of substitutions selected from the group consisting of:

K35A+A51T+N54A+G109A+R118T+W140Y+R172S+N174*+R181Q+E190P+I206L+I235L+Y243F+F267Y+Q280N+K281F+N299A+K302T+R320K+S334T+A339S+E345Q+E346P+V4101;

N311K+I312L+F313L+Q319S+R320K+H324K+S334T+E345Q+E346P+L355F+T356I+Q361S+Y371M+R383K+S384H+D387E+E391K+Q394K+K395Q+P400A+V410I+E471T+D476K;

N22Q+N25R+N28Q+S29N+A51T+N54A+N70H+R82K+S83G+Q84E+V89I+T90K+K93H+Q98N+G109A+M116D+R118T+E130V+T136L+E138K+W140Y+R142H+D144H+N150S+H152Y+S154D+R158Y+R172S+N174*+R181Q+E190P+I206L+Y243F+F267Y+Q280N+K281F+N299A+K302N+R320K+S334T+A339S+E345Q+E346P+T356I+Q361S+V410I+E471T+D476K

H1*+N3A+M9L+K35A+W48Y+A51T+N54A+M105I+G109A+R118Q+W140Y+R172S+N174*+R181Q+E190P+I206L+V214I+I235L+Y243F+T246L+F267Y+Q280N+K281F+N299A+K302T+R320K+S334T+A339S+E345Q+E346P+V379I+M382L+V410I+D476K+K485R;

H1A+N3A+M9L+K35A+W48Y+A51T+N54A+M105I+G109A+R118T+W140Y+R172S+N174*+R181Q+E190P+I206L+I235L+Y243F+T246L+F267Y+Q280N+K281F+N299A+K302T+R320K+S334T+A339S+E345Q+E346P+V379I+M382L+V410I+D476K;

A51T+N54A+G109A+R118T+E134D+W140Y+R172S+E190P+I206L+Y243F+F267Y+Q280N+K281F+N299A+K302N+R320K+S334T+A339S+V410I+E471T+D476K;

N22Q+N25K+N28Q+S29N+K35A+A51T+N54A+N70H+Q84D+V89I+T90K+K93H+Q98N+G109A+M116D+R118Q+E130V+V131I+T136L+E138K+W167F+R172S+R181Q+I206L+G229Q+I235L+Y243F+F267Y+Q280N+K281F+N299A+K302N+Q319S+R320K+S334T+A339S+F343T+E345Q+E346T+I374T+V379I+M382L+R383K+P400A+V410I+K423N+L444A+K463V+E471T+D476K;

H1A+N3A+A51T+N54A+G109A+R118T+E134D+W140Y+R172S+N174S+E190P+I206L+Y243F+F267Y+Q280N+K281F+N299A+K302N+R320K+S334T+A339S+V4101+1411V+K423N+S437A+A442V+L444R+K445Q+Y452H+D460E+T461P+K463V+G465N+D467E+D476K+K485R;

H1*+N3A+A51T+N54A+G109A+R118T+E134D+W140Y+R172S+N174S+E190P+I206L+Y243F+F267Y+Q280N+K281F+N299A+K302N+R320K+S334T+A339S+V4101+1411V+K423N+S437A+A442V+L444R+K445Q+Y452H+D460E+T461P+K463V+G465N+D467E+D476K+K485R;

H1A+N3A+K35A+A51T+N54A+G109A+R118T+W140Y+R172S+N174S+R181Q+E190P+I206L+I235L+Y243F+F267Y+Q280N+K281F+N299A+K302T+R320K+S334T+A339S+E345Q+E346P+P408H+V4101+1411V+K423N+S437A+A442V+L444R+K445Q+Y452H+D460E+T461P+K463V+G465N+D467E+D476K+K485R; and H1A+H2*+N3A+M9L+K35A+W48Y+A51T+N54A+M105I+G109A+R118T+W140Y+R172S+R181Q+E188P+I204L+I233L+Y241F+T244L+F265Y+Q278N+K279F+N297A+K300T+R318K+S332T+A337S+E343Q+E344P+V377I+M380L+V408I+D474K;

using SEQ ID NO: 1 for numbering; and wherein said variant has at least 80% but less than 100% sequence identity to the amino acid sequence to the polypeptide of SEQ ID NO: 1; wherein said variant has alpha-amylase activity; and wherein said variant has an Improvement Factor (IF)>1.0 for a measure of wash performance when compared to said alpha-amylase having alpha-amylase activity and comprising the polypeptide of SEQ ID NO: 2.

2. The alpha-amylase variant according to claim 1, wherein said parent alpha amylase comprises the polypeptide of SEQ ID NO: 1, SEQ ID NO: 2, SEQ ID NO: 3, SEQ ID NO: 4, SEQ ID NO: 5, SEQ ID NO: 6, SEQ ID NO: 11, or SEQ ID NO: 12.

3. A method of producing an alpha-amylase variant of claim 1, comprising:

a) cultivating an isolated recombinant host cell expressing variant of claim 1 under conditions suitable for expression of said variant; and b) recovering said variant.

4. A detergent composition comprising the variant according to claim 1.

5. The composition according to claim 4, further comprising at least one detergent component.

6. The composition according to claim 5 wherein the one or more detergent component is selected from a group consisting of builders, chelants, polymers, buffers, bactericides, preservatives, hydrotropes, colorants, stabilizers, radical scavengers, bleaches, bleach activators, soil suspenders, dye transfer agents, brighteners, anti-dusting agents, dispersants, dye transfer inhibitors, pigments, silicones, perfumes and/or dyes.

7. A method of treating a surface, comprising a. forming an aqueous wash liquor comprising water, the amylase of claim 1, and a cleaning adjunct, b. treating the surface with the aqueous wash liquor at a temperature in the range of 5° C.-60° C., and c. rinsing the surface.

8. A method of manual dishwashing using a detergent composition according to claim 4 comprising the steps of applying said composition to said dishware and rinsing the dishware.

9. The alpha-amylase variant of claim 1, wherein said variant has at least 85% but less than 100% sequence identity to the polypeptide of SEQ ID NO: 2 and wherein said variant has alpha-amylase activity and wherein said variant has an Improvement Factor (IF)>1.0 for a measure of wash performance when compared to the alpha-amylase having alpha-amylase activity and comprising the polypeptide of SEQ ID NO: 2.

10. The alpha-amylase variant of claim 1, wherein said variant has at least 90% but less than 100% sequence identity to the polypeptide of SEQ ID NO: 2 and wherein said variant has alpha-amylase activity and wherein said variant has an Improvement Factor (IF)>1.0 for a measure of wash performance when compared to the alpha-amylase having alpha-amylase activity and comprising the polypeptide of SEQ ID NO: 2.

11. The alpha-amylase variant of claim 1, wherein said variant has at least 95% but less than 100% sequence identity to the polypeptide of SEQ ID NO: 2 and wherein said variant has alpha-amylase activity and wherein said variant has an Improvement Factor (IF)>1.0 for a measure of wash performance when compared to the alpha-amylase having alpha-amylase activity and comprising the polypeptide of SEQ ID NO: 2.

12. The alpha-amylase variant of claim 1, wherein said variant has at least 97% but less than 100% sequence identity to the polypeptide of SEQ ID NO: 2 and wherein said variant has alpha-amylase activity and wherein said variant has an Improvement Factor (IF)>1.0 for a measure of wash performance when compared to the alpha-amylase having alpha-amylase activity and comprising the polypeptide of SEQ ID NO: 2.

13. The alpha-amylase variant of claim 1, wherein said variant has at least 98% but less than 100% sequence identity to the polypeptide of SEQ ID NO: 2 and wherein said variant has alpha-amylase activity and wherein said variant has an Improvement Factor (IF)>1.0 for a measure of wash performance when compared to the alpha-amylase having alpha-amylase activity and comprising the polypeptide of SEQ ID NO: 2.

* * * * *

SEQUENCE LISTING

```
<160> NUMBER OF SEQ ID NOS: 18

<210> SEQ ID NO 1
<211> LENGTH: 485
<212> TYPE: PRT
<213> ORGANISM: Artificial sequence
<220> FEATURE:
<223> OTHER INFORMATION: Synthetic construct

<400> SEQUENCE: 1

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
```

-continued

```
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Pro
385                 390                 395                 400

Gln His Asp Tyr Leu Asp His Pro Asp Val Ile Gly Trp Thr Arg Glu
                405                 410                 415

Gly Asp Ser Ser His Pro Lys Ser Gly Leu Ala Thr Leu Ile Thr Asp
            420                 425                 430

Gly Pro Gly Gly Ser Lys Arg Met Tyr Ala Gly Leu Lys Asn Ala Gly
        435                 440                 445

Glu Thr Trp Tyr Asp Ile Thr Gly Asn Arg Ser Asp Thr Val Lys Ile
    450                 455                 460
```

Gly Ser Asp Gly Trp Gly Glu Phe His Val Asn Asp Gly Ser Val Ser
465 470 475 480

Ile Tyr Val Gln Lys
485

<210> SEQ ID NO 2
<211> LENGTH: 483
<212> TYPE: PRT
<213> ORGANISM: Artificial sequence
<220> FEATURE:
<223> OTHER INFORMATION: Synthetic construct

<400> SEQUENCE: 2

His His Asn Gly Thr Asn Gly Thr Met Met Gln Tyr Phe Glu Trp Tyr
1 5 10 15

Leu Pro Asn Asp Gly Asn His Trp Asn Arg Leu Asn Ser Asp Ala Ser
20 25 30

Asn Leu Lys Ser Lys Gly Ile Thr Ala Val Trp Ile Pro Pro Ala Trp
35 40 45

Lys Gly Ala Ser Gln Asn Asp Val Gly Tyr Gly Ala Tyr Asp Leu Tyr
50 55 60

Asp Leu Gly Glu Phe Asn Gln Lys Gly Thr Val Arg Thr Lys Tyr Gly
65 70 75 80

Thr Arg Ser Gln Leu Gln Ala Ala Val Thr Ser Leu Lys Asn Asn Gly
85 90 95

Ile Gln Val Tyr Gly Asp Val Val Met Asn His Lys Gly Gly Ala Asp
100 105 110

Ala Thr Glu Met Val Arg Ala Val Glu Val Asn Pro Asn Asn Arg Asn
115 120 125

Gln Glu Val Thr Gly Glu Tyr Thr Ile Glu Ala Trp Thr Arg Phe Asp
130 135 140

Phe Pro Gly Arg Gly Asn Thr His Ser Ser Phe Lys Trp Arg Trp Tyr
145 150 155 160

His Phe Asp Gly Val Asp Trp Asp Gln Ser Arg Arg Leu Asn Asn Arg
165 170 175

Ile Tyr Lys Phe Arg Gly Lys Ala Trp Asp Trp Glu Val Asp Thr Glu
180 185 190

Asn Gly Asn Tyr Asp Tyr Leu Met Tyr Ala Asp Ile Asp Met Asp His
195 200 205

Pro Glu Val Val Asn Glu Leu Arg Asn Trp Gly Val Trp Tyr Thr Asn
210 215 220

Thr Leu Gly Leu Asp Gly Phe Arg Ile Asp Ala Val Lys His Ile Lys
225 230 235 240

Tyr Ser Phe Thr Arg Asp Trp Ile Asn His Val Arg Ser Ala Thr Gly
245 250 255

Lys Asn Met Phe Ala Val Ala Glu Phe Trp Lys Asn Asp Leu Gly Ala
260 265 270

Ile Glu Asn Tyr Leu Gln Lys Thr Asn Trp Asn His Ser Val Phe Asp
275 280 285

Val Pro Leu His Tyr Asn Leu Tyr Asn Ala Ser Lys Ser Gly Gly Asn
290 295 300

Tyr Asp Met Arg Asn Ile Phe Asn Gly Thr Val Val Gln Arg His Pro
305 310 315 320

Ser His Ala Val Thr Phe Val Asp Asn His Asp Ser Gln Pro Glu Glu
325 330 335

Ala Leu Glu Ser Phe Val Glu Glu Trp Phe Lys Pro Leu Ala Tyr Ala
340 345 350

Leu Thr Leu Thr Arg Glu Gln Gly Tyr Pro Ser Val Phe Tyr Gly Asp
355 360 365

Tyr Tyr Gly Ile Pro Thr His Gly Val Pro Ala Met Arg Ser Lys Ile
370 375 380

Asp Pro Ile Leu Glu Ala Arg Gln Lys Tyr Ala Tyr Gly Pro Gln His
385 390 395 400

Asp Tyr Leu Asp His Pro Asp Val Ile Gly Trp Thr Arg Glu Gly Asp
405 410 415

Ser Ser His Pro Lys Ser Gly Leu Ala Thr Leu Ile Thr Asp Gly Pro
420 425 430

Gly Gly Ser Lys Arg Met Tyr Ala Gly Leu Lys Asn Ala Gly Glu Thr
435 440 445

Trp Tyr Asp Ile Thr Gly Asn Arg Ser Asp Thr Val Lys Ile Gly Ser
450 455 460

Asp Gly Trp Gly Glu Phe His Val Asn Asp Gly Ser Val Ser Ile Tyr
465 470 475 480

Val Gln Lys

<210> SEQ ID NO 3
<211> LENGTH: 485
<212> TYPE: PRT
<213> ORGANISM: Artificial sequence
<220> FEATURE:
<223> OTHER INFORMATION: Synthetic construct

<400> SEQUENCE: 3

His His Asn Gly Thr Asn Gly Thr Met Met Gln Tyr Phe Glu Trp Tyr
1 5 10 15

Leu Pro Asn Asp Gly Asn His Trp Asn Arg Leu Asn Ser Asp Ala Ser
20 25 30

Asn Leu Lys Ser Lys Gly Ile Thr Ala Val Trp Ile Pro Pro Ala Trp
35 40 45

Lys Gly Ala Ser Gln Asn Asp Val Gly Tyr Gly Ala Tyr Asp Leu Tyr
50 55 60

Asp Leu Gly Glu Phe Asn Gln Lys Gly Thr Val Arg Thr Lys Tyr Gly
65 70 75 80

Thr Arg Ser Gln Leu Gln Ala Ala Val Thr Ser Leu Lys Asn Asn Gly
85 90 95

Ile Gln Val Tyr Gly Asp Val Val Met Asn His Lys Gly Gly Ala Asp
100 105 110

Ala Thr Glu Met Val Arg Ala Val Glu Val Asn Pro Asn Asn Arg Asn
115 120 125

Gln Glu Val Thr Gly Glu Tyr Thr Ile Glu Ala Trp Thr Arg Phe Asp
130 135 140

Phe Pro Gly Arg Gly Asn Thr His Ser Ser Phe Lys Trp Arg Trp Tyr
145 150 155 160

His Phe Asp Gly Val Asp Trp Asp Gln Ser Arg Arg Leu Asn Asn Arg
165 170 175

Ile Tyr Lys Phe Arg Gly His Gly Lys Ala Trp Asp Trp Glu Val Asp
180 185 190

Thr Glu Asn Gly Asn Tyr Asp Tyr Leu Met Tyr Ala Asp Ile Asp Met
195 200 205

```
Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Pro
385                 390                 395                 400

Gln His Asp Tyr Ile Asp His Pro Asp Val Ile Gly Trp Thr Arg Glu
                405                 410                 415

Gly Asp Ser Ser Ala Ala Lys Ser Gly Leu Ala Ala Leu Ile Thr Asp
            420                 425                 430

Gly Pro Gly Gly Ser Lys Arg Met Tyr Ala Gly Leu Lys Asn Ala Gly
        435                 440                 445

Glu Thr Trp Tyr Asp Ile Thr Gly Asn Arg Ser Asp Thr Val Lys Ile
    450                 455                 460

Gly Ser Asp Gly Trp Gly Glu Phe His Val Asn Asp Gly Ser Val Ser
465                 470                 475                 480

Ile Tyr Val Gln Lys
                485


<210> SEQ ID NO 4
<211> LENGTH: 483
<212> TYPE: PRT
<213> ORGANISM: Artificial sequence
<220> FEATURE:
<223> OTHER INFORMATION: Synthetic construct

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80
```

```
Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365

Tyr Tyr Gly Ile Pro Thr His Gly Val Pro Ala Met Arg Ser Lys Ile
    370                 375                 380

Asp Pro Ile Leu Glu Ala Arg Gln Lys Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys
```

<210> SEQ ID NO 5

```
<211> LENGTH: 485
<212> TYPE: PRT
<213> ORGANISM: Bacillus sp.

<400> SEQUENCE: 5

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
```

385 390 395 400

Gln Asn Asp Tyr Leu Asp His His Asn Ile Ile Gly Trp Thr Arg Glu
405 410 415

Gly Asn Thr Ala His Pro Asn Ser Gly Leu Ala Thr Ile Met Ser Asp
420 425 430

Gly Ala Gly Gly Asn Lys Trp Met Phe Val Gly Arg Asn Lys Ala Gly
435 440 445

Gln Val Trp Thr Asp Ile Thr Gly Asn Arg Ala Gly Thr Val Thr Ile
450 455 460

Asn Ala Asp Gly Trp Gly Asn Phe Ser Val Asn Gly Gly Ser Val Ser
465 470 475 480

Ile Trp Val Asn Lys
485

<210> SEQ ID NO 6
<211> LENGTH: 485
<212> TYPE: PRT
<213> ORGANISM: Bacillus sp.

<400> SEQUENCE: 6

His His Asn Gly Thr Asn Gly Thr Met Met Gln Tyr Phe Glu Trp His
1 5 10 15

Leu Pro Asn Asp Gly Asn His Trp Asn Arg Leu Arg Asp Asp Ala Ser
20 25 30

Asn Leu Arg Asn Arg Gly Ile Thr Ala Ile Trp Ile Pro Pro Ala Trp
35 40 45

Lys Gly Thr Ser Gln Asn Asp Val Gly Tyr Gly Ala Tyr Asp Leu Tyr
50 55 60

Asp Leu Gly Glu Phe Asn Gln Lys Gly Thr Val Arg Thr Lys Tyr Gly
65 70 75 80

Thr Arg Ser Gln Leu Glu Ser Ala Ile His Ala Leu Lys Asn Asn Gly
85 90 95

Val Gln Val Tyr Gly Asp Val Val Met Asn His Lys Gly Gly Ala Asp
100 105 110

Ala Thr Glu Asn Val Leu Ala Val Glu Val Asn Pro Asn Asn Arg Asn
115 120 125

Gln Glu Ile Ser Gly Asp Tyr Thr Ile Glu Ala Trp Thr Lys Phe Asp
130 135 140

Phe Pro Gly Arg Gly Asn Thr Tyr Ser Asp Phe Lys Trp Arg Trp Tyr
145 150 155 160

His Phe Asp Gly Val Asp Trp Asp Gln Ser Arg Gln Phe Gln Asn Arg
165 170 175

Ile Tyr Lys Phe Arg Gly Asp Gly Lys Ala Trp Asp Trp Glu Val Asp
180 185 190

Ser Glu Asn Gly Asn Tyr Asp Tyr Leu Met Tyr Ala Asp Val Asp Met
195 200 205

Asp His Pro Glu Val Val Asn Glu Leu Arg Arg Trp Gly Glu Trp Tyr
210 215 220

Thr Asn Thr Leu Asn Leu Asp Gly Phe Arg Ile Asp Ala Val Lys His
225 230 235 240

Ile Lys Tyr Ser Phe Thr Arg Asp Trp Leu Thr His Val Arg Asn Ala
245 250 255

Thr Gly Lys Glu Met Phe Ala Val Ala Glu Phe Trp Lys Asn Asp Leu
260 265 270

```
Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asp Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485


<210> SEQ ID NO 7
<211> LENGTH: 485
<212> TYPE: PRT
<213> ORGANISM: Bacillus sp.

<400> SEQUENCE: 7

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160
```

His Phe Asp Gly Thr Asp Trp Asp Gln Ser Arg Gln Leu Ala Asn Arg
165 170 175

Ile Tyr Lys Phe Arg Gly Asp Gly Lys Ala Trp Asp Trp Glu Val Asp
180 185 190

Thr Glu Asn Gly Asn Tyr Asp Tyr Leu Met Tyr Ala Asp Val Asp Met
195 200 205

Asp His Pro Glu Val Ile Asn Glu Leu Asn Arg Trp Gly Val Trp Tyr
210 215 220

Ala Asn Thr Leu Asn Leu Asp Gly Phe Arg Leu Asp Ala Val Lys His
225 230 235 240

Ile Lys Phe Ser Phe Met Arg Asp Trp Leu Gly His Val Arg Gly Gln
245 250 255

Thr Gly Lys Asn Leu Phe Ala Val Ala Glu Tyr Trp Lys Asn Asp Leu
260 265 270

Gly Ala Leu Glu Asn Tyr Leu Ser Lys Thr Asn Trp Thr Met Ser Ala
275 280 285

Phe Asp Val Pro Leu His Tyr Asn Leu Tyr Gln Ala Ser Asn Ser Ser
290 295 300

Gly Asn Tyr Asp Met Arg Asn Leu Leu Asn Gly Thr Leu Val Gln Arg
305 310 315 320

His Pro Ser His Ala Val Thr Phe Val Asp Asn His Asp Thr Gln Pro
325 330 335

Gly Glu Ala Leu Glu Ser Phe Val Gln Gly Trp Phe Lys Pro Leu Ala
340 345 350

Tyr Ala Thr Ile Leu Thr Arg Glu Gln Gly Tyr Pro Gln Val Phe Tyr
355 360 365

Gly Asp Tyr Tyr Gly Ile Pro Ser Asp Gly Val Pro Ser Tyr Arg Gln
370 375 380

Gln Ile Asp Pro Leu Leu Lys Ala Arg Gln Gln Tyr Ala Tyr Gly Arg
385 390 395 400

Gln His Asp Tyr Phe Asp His Trp Asp Val Ile Gly Trp Thr Arg Glu
405 410 415

Gly Asn Ala Ser His Pro Asn Ser Gly Leu Ala Thr Ile Met Ser Asp
420 425 430

Gly Pro Gly Gly Ser Lys Trp Met Tyr Val Gly Arg Gln Lys Ala Gly
435 440 445

Glu Val Trp His Asp Met Thr Gly Asn Arg Ser Gly Thr Val Thr Ile
450 455 460

Asn Gln Asp Gly Trp Gly His Phe Phe Val Asn Gly Gly Ser Val Ser
465 470 475 480

Val Trp Val Lys Arg
485

<210> SEQ ID NO 8
<211> LENGTH: 485
<212> TYPE: PRT
<213> ORGANISM: Cytophaga sp.

<400> SEQUENCE: 8

Ala Ala Thr Asn Gly Thr Met Met Gln Tyr Phe Glu Trp Tyr Val Pro
1 5 10 15

Asn Asp Gly Gln Gln Trp Asn Arg Leu Arg Thr Asp Ala Pro Tyr Leu
20 25 30

Ser Ser Val Gly Ile Thr Ala Val Trp Thr Pro Pro Ala Tyr Lys Gly

-continued

```
        35                  40                  45

Thr Ser Gln Ala Asp Val Gly Tyr Gly Pro Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460
```

Gly Ser Asp Gly Tyr Ala Thr Phe Pro Val Asn Gly Gly Ser Val Ser
465 470 475 480

Val Trp Val Gln Gln
485

<210> SEQ ID NO 9
<211> LENGTH: 484
<212> TYPE: PRT
<213> ORGANISM: Bacillus sp.

<400> SEQUENCE: 9

Asn Thr Ala Pro Ile Asn Glu Thr Met Met Gln Tyr Phe Glu Trp Asp
1 5 10 15

Leu Pro Asn Asp Gly Thr Leu Trp Thr Lys Val Lys Asn Glu Ala Ala
20 25 30

Asn Leu Ser Ser Leu Gly Ile Thr Ala Leu Trp Leu Pro Pro Ala Tyr
35 40 45

Lys Gly Thr Ser Gln Ser Asp Val Gly Tyr Gly Val Tyr Asp Leu Tyr
50 55 60

Asp Leu Gly Glu Phe Asn Gln Lys Gly Thr Ile Arg Thr Lys Tyr Gly
65 70 75 80

Thr Lys Thr Gln Tyr Ile Gln Ala Ile Gln Ala Ala Lys Ala Ala Gly
85 90 95

Met Gln Val Tyr Ala Asp Val Val Phe Asn His Lys Ala Gly Ala Asp
100 105 110

Gly Thr Glu Phe Val Asp Ala Val Glu Val Asp Pro Ser Asn Arg Asn
115 120 125

Gln Glu Thr Ser Gly Thr Tyr Gln Ile Gln Ala Trp Thr Lys Phe Asp
130 135 140

Phe Pro Gly Arg Gly Asn Thr Tyr Ser Ser Phe Lys Trp Arg Trp Tyr
145 150 155 160

His Phe Asp Gly Thr Asp Trp Asp Glu Ser Arg Lys Leu Asn Arg Ile
165 170 175

Tyr Lys Phe Arg Ser Thr Gly Lys Ala Trp Asp Trp Glu Val Asp Thr
180 185 190

Glu Asn Gly Asn Tyr Asp Tyr Leu Met Phe Ala Asp Leu Asp Met Asp
195 200 205

His Pro Glu Val Val Thr Glu Leu Lys Asn Trp Gly Thr Trp Tyr Val
210 215 220

Asn Thr Thr Asn Ile Asp Gly Phe Arg Leu Asp Ala Val Lys His Ile
225 230 235 240

Lys Tyr Ser Phe Phe Pro Asp Trp Leu Thr Tyr Val Arg Asn Gln Thr
245 250 255

Gly Lys Asn Leu Phe Ala Val Gly Glu Phe Trp Ser Tyr Asp Val Asn
260 265 270

Lys Leu His Asn Tyr Ile Thr Lys Thr Asn Gly Ser Met Ser Leu Phe
275 280 285

Asp Ala Pro Leu His Asn Asn Phe Tyr Thr Ala Ser Lys Ser Ser Gly
290 295 300

Tyr Phe Asp Met Arg Tyr Leu Leu Asn Asn Thr Leu Met Lys Asp Gln
305 310 315 320

Pro Ser Leu Ala Val Thr Leu Val Asp Asn His Asp Thr Gln Pro Gly
325 330 335

Gln Ser Leu Gln Ser Trp Val Glu Pro Trp Phe Lys Pro Leu Ala Tyr

```
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys


<210> SEQ ID NO 10
<211> LENGTH: 483
<212> TYPE: PRT
<213> ORGANISM: Bacillus amyloliquefaciens

<400> SEQUENCE: 10

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
```

```
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys


<210> SEQ ID NO 11
<211> LENGTH: 485
<212> TYPE: PRT
<213> ORGANISM: Bacillus sp.

<400> SEQUENCE: 11

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
```

-continued

```
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485


<210> SEQ ID NO 12
<211> LENGTH: 484
<212> TYPE: PRT
<213> ORGANISM: Bacillus sp.

<400> SEQUENCE: 12
```

```
His His Asn Gly Thr Asn Gly Thr Met Met Gln Tyr Phe Glu Trp His
1               5                   10                  15

Leu Pro Asn Asp Gly Gln His Trp Asn Arg Leu Arg Asn Asp Ala Ala
            20                  25                  30

Asn Leu Lys Asn Leu Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Ser Gln Leu Gln Ser Ala Ile Ala Ser Leu Gln Asn Asn Gly
                85                  90                  95

Ile Gln Val Tyr Gly Asp Ala Met Asn His Lys Gly Gly Ala Asp Gly
            100                 105                 110

Thr Glu Trp Val Gln Ala Val Glu Val Asn Pro Ser Asn Arg Asn Gln
        115                 120                 125

Glu Val Thr Gly Glu Tyr Thr Ile Glu Ala Trp Thr Lys Phe Asp Phe
    130                 135                 140

Pro Gly Arg Gly Asn Thr His Ser Ser Phe Lys Trp Arg Trp Tyr His
145                 150                 155                 160

Phe Asp Gly Thr Asp Trp Asp Gln Ser Arg Gln Leu Asn Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Val Asp Met Asp
        195                 200                 205

His Pro Glu Val Ile Asn Glu Leu Arg Arg Trp Gly Val Trp Tyr Thr
    210                 215                 220

Asn Thr Leu Asn Leu Asp Gly Phe Arg Ile Asp Ala Val Lys His Ile
225                 230                 235                 240

Lys Tyr Ser Phe Thr Arg Asp Trp Leu Asn His Val Arg Ser Thr Thr
                245                 250                 255

Gly Lys Asn Asn Met Phe Ala Val Ala Glu Phe Trp Lys Asn Asp Leu
            260                 265                 270

Gly Ala Ile Glu Asn Tyr Leu His Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Leu Asn Gly Thr Trp Ser Lys His
305                 310                 315                 320

Pro Ile His Ala Val Thr Phe Val Asp Asn His Asp Ser Gln Pro Ala
                325                 330                 335

Glu Ala Leu Glu Ser Phe Val Glu Ala Trp Phe Lys Pro Leu Ala Tyr
            340                 345                 350

Ala Leu Ile Leu Thr Arg Glu Gln Gly Tyr Pro Ser Val Phe Tyr Gly
        355                 360                 365

Asp Tyr Tyr Gly Ile Pro Thr His Gly Val Ala Ala Met Lys Gly Lys
    370                 375                 380

Ile Asp Pro Ile Leu Glu Ala Arg Gln Lys Tyr Ala Tyr Gly Thr Gln
385                 390                 395                 400

His Asp Tyr Leu Asp His His Asn Ile Ile Gly Trp Thr Arg Glu Gly
                405                 410                 415

Asn Ser Ala His Pro Asn Ser Gly Leu Ala Thr Ile Met Ser Asp Gly
```

```
            420                 425                 430

Pro Gly Gly Ser Lys Trp Met Tyr Val Gly Arg His Lys Ala Gly Gln
        435                 440                 445

Val Trp Arg Asp Ile Thr Gly Asn Arg Thr Gly Thr Val Thr Ile Asn
    450                 455                 460

Ala Asp Gly Trp Gly Asn Phe Ser Val Asn Gly Gly Ser Val Ser Ile
465                 470                 475                 480

Trp Val Asn Lys


<210> SEQ ID NO 13
<211> LENGTH: 486
<212> TYPE: PRT
<213> ORGANISM: Alicyclobacillus sp.

<400> SEQUENCE: 13

Thr Phe Ala Gly Asp Asn Gly Thr Met Met Gln Tyr Phe Glu Trp Tyr
1               5                   10                  15

Leu Pro Asn Asp Gly Thr Leu Trp Thr Lys Met Gly Ser Asp Ala Ser
            20                  25                  30

His Leu Lys Ser Ile Gly Ile Thr Gly Val Trp Phe Pro Pro Ala Tyr
        35                  40                  45

Lys Gly Gln Ser Gln Ser Asp Val Gly Tyr Gly Val Tyr Asp Met Tyr
    50                  55                  60

Asp Leu Gly Glu Phe Asn Gln Lys Gly Thr Val Arg Thr Lys Tyr Gly
65                  70                  75                  80

Thr Lys Ala Gln Leu Gln Ser Ala Ile Thr Ser Leu His Asn Asn Gly
                85                  90                  95

Ile Gln Ala Tyr Gly Asp Val Val Leu Asn His Arg Met Gly Ala Asp
            100                 105                 110

Ala Thr Glu Thr Ile Ser Ala Val Glu Val Asn Pro Ser Asn Arg Asn
        115                 120                 125

Gln Val Thr Ser Gly Ala Tyr Asn Ile Ser Ala Trp Thr Asp Phe Glu
    130                 135                 140

Phe Pro Gly Arg Gly Asn Thr Tyr Ser Ser Phe Lys Trp His Ser Tyr
145                 150                 155                 160

Tyr Phe Asp Gly Val Asp Trp Asp Gln Ser Arg Gln Leu Ser Gly Lys
                165                 170                 175

Ile Tyr Gln Ile Gln Gly Thr Gly Lys Ala Trp Asp Trp Glu Val Asp
            180                 185                 190

Ser Glu Asn Gly Asn Tyr Asp Tyr Leu Met Gly Ala Asp Ile Asp Tyr
        195                 200                 205

Asp His Pro Asp Val Gln Thr Glu Val Lys Asn Trp Gly Lys Trp Phe
    210                 215                 220

Val Asn Thr Leu Asn Leu Asp Gly Val Arg Leu Asp Ala Val Lys His
225                 230                 235                 240

Ile Lys Phe Asp Tyr Met Ser Ser Trp Leu Ser Ser Val Lys Ser Thr
                245                 250                 255

Thr Gly Lys Ser Asn Leu Phe Ala Val Gly Glu Tyr Trp Asn Thr Ser
            260                 265                 270

Leu Gly Ala Leu Glu Asn Tyr Glu Asn Lys Thr Asn Trp Ser Met Ser
        275                 280                 285

Leu Phe Asp Val Pro Leu His Met Asn Phe Gln Ala Ala Ala Asn Gly
    290                 295                 300

Gly Gly Tyr Tyr Asp Met Arg Asn Leu Leu Asn Asn Thr Met Met Lys
```

```
305                 310                 315                 320

Asn His Pro Ile Gln Ala Val Thr Phe Val Asp Asn His Asp Thr Glu
                325                 330                 335

Pro Gly Gln Ala Leu Gln Ser Trp Val Ser Asp Trp Phe Lys Pro Leu
            340                 345                 350

Ala Tyr Ala Thr Ile Leu Thr Arg Gln Glu Gly Tyr Pro Cys Val Phe
        355                 360                 365

Tyr Gly Asp Tyr Tyr Gly Ile Pro Ser Gln Ser Val Ser Ala Lys Ser
    370                 375                 380

Thr Trp Leu Asp Lys Gln Leu Ser Ala Arg Lys Ser Tyr Ala Tyr Gly
385                 390                 395                 400

Thr Gln His Asp Tyr Leu Asp Asn Gln Asp Val Ile Gly Trp Thr Arg
                405                 410                 415

Glu Gly Asp Ser Ala His Ala Gly Ser Gly Leu Ala Thr Val Met Ser
            420                 425                 430

Asp Gly Pro Gly Gly Ser Lys Thr Met Tyr Val Gly Thr Ala His Ala
        435                 440                 445

Gly Gln Val Phe Lys Asp Ile Thr Gly Asn Arg Thr Asp Thr Val Thr
    450                 455                 460

Ile Asn Ser Ala Gly Asn Gly Thr Phe Pro Cys Asn Gly Gly Ser Val
465                 470                 475                 480

Ser Ile Trp Val Lys Gln
                485
```

<210> SEQ ID NO 14
<211> LENGTH: 399
<212> TYPE: PRT
<213> ORGANISM: Artificial sequence
<220> FEATURE:
<223> OTHER INFORMATION: Synthetic construct

<400> SEQUENCE: 14

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
```

180 185 190

Thr Glu Asn Gly Asn Tyr Asp Tyr Leu Met Tyr Ala Asp Ile Asp Met
195 200 205

Asp His Pro Glu Val Val Asn Glu Leu Arg Asn Trp Gly Val Trp Tyr
210 215 220

Thr Asn Thr Leu Gly Leu Asp Gly Phe Arg Ile Asp Ala Val Lys His
225 230 235 240

Ile Lys Tyr Ser Phe Thr Arg Asp Trp Ile Asn His Val Arg Ser Ala
245 250 255

Thr Gly Lys Asn Met Phe Ala Val Ala Glu Phe Trp Lys Asn Asp Leu
260 265 270

Gly Ala Ile Glu Asn Tyr Leu Gln Lys Thr Asn Trp Asn His Ser Val
275 280 285

Phe Asp Val Pro Leu His Tyr Asn Leu Tyr Asn Ala Ser Lys Ser Gly
290 295 300

Gly Asn Tyr Asp Met Arg Asn Ile Phe Asn Gly Thr Val Val Gln Arg
305 310 315 320

His Pro Ser His Ala Val Thr Phe Val Asp Asn His Asp Ser Gln Pro
325 330 335

Glu Glu Ala Leu Glu Ser Phe Val Glu Glu Trp Phe Lys Pro Leu Ala
340 345 350

Tyr Ala Leu Thr Leu Thr Arg Glu Gln Gly Tyr Pro Ser Val Phe Tyr
355 360 365

Gly Asp Tyr Tyr Gly Ile Pro Thr His Gly Val Pro Ala Met Arg Ser
370 375 380

Lys Ile Asp Pro Ile Leu Glu Ala Arg Gln Lys Tyr Ala Tyr Gly
385 390 395

<210> SEQ ID NO 15
<211> LENGTH: 86
<212> TYPE: PRT
<213> ORGANISM: Artificial sequence
<220> FEATURE:
<223> OTHER INFORMATION: Synthetic construct

<400> SEQUENCE: 15

Lys Gln Asn Asp Tyr Leu Asp His His Asn Ile Ile Gly Trp Thr Arg
1 5 10 15

Glu Gly Asn Thr Ala His Pro Asn Ser Gly Leu Ala Thr Ile Met Ser
20 25 30

Asp Gly Ala Gly Gly Ser Lys Trp Met Phe Val Gly Arg Asn Lys Ala
35 40 45

Gly Gln Val Trp Ser Asp Ile Thr Gly Asn Arg Thr Gly Thr Val Thr
50 55 60

Ile Asn Ala Asp Gly Trp Gly Asn Phe Ser Val Asn Gly Gly Ser Val
65 70 75 80

Ser Ile Trp Val Asn Lys
85

<210> SEQ ID NO 16
<211> LENGTH: 397
<212> TYPE: PRT
<213> ORGANISM: Artificial sequence
<220> FEATURE:
<223> OTHER INFORMATION: Synthetic construct

<400> SEQUENCE: 16

```
Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly
385                 390                 395
```

<210> SEQ ID NO 17
<211> LENGTH: 85
<212> TYPE: PRT

-continued

<213> ORGANISM: Artificial sequence
<220> FEATURE:
<223> OTHER INFORMATION: Synthetic construct

<400> SEQUENCE: 17

```
Pro Gln His Asp Tyr Ile Asp His Pro Asp Val Ile Gly Trp Thr Arg
1               5                   10                  15

Glu Gly Asp Ser Ser Ala Ala Lys Ser Gly Leu Ala Ala Leu Ile Thr
            20                  25                  30

Asp Gly Pro Gly Gly Ser Lys Arg Met Tyr Ala Gly Leu Lys Asn Ala
        35                  40                  45

Gly Thr Trp Tyr Asp Ile Thr Gly Asn Arg Ser Asp Thr Val Lys Ile
    50                  55                  60

Gly Ser Asp Gly Trp Gly Glu Phe His Val Asn Asp Gly Ser Val Ser
65                  70                  75                  80

Ile Tyr Val Gln Lys
                85
```

<210> SEQ ID NO 18
<211> LENGTH: 849
<212> TYPE: DNA
<213> ORGANISM: Artificial sequence
<220> FEATURE:
<223> OTHER INFORMATION: Synthetic construct

<400> SEQUENCE: 18

```
tacgctgata ttgatatgga tcacccagaa gtagtaaatg aattaagaaa ttggggtgtt      60

tggtacacaa acacattagg actcgatgga tttagaatag atgcggttaa acatataaag     120

tatagcttta cgcgcgattg gattaatcac gttagaagtg caacaggtaa aaatatgttt     180

gcggttgctg agttttggaa gaatgattta ggtgcaattg aaaactatct gcagaaaaca     240

aactggaacc attcagtctt tgatgtgccg ttacattata atctttataa tgcatcaaaa     300

agcggaggga actatgatat gcgaaacata tttaatggaa cggttgttca acgacatcca     360

agtcatgctg taacatttgt tgataatcat gattcgcagc ctgaagaagc attagaatct     420

tttgttgaag aatggtttaa accattagcg tatgcgctta cattaacgcg tgaacaagga     480

tacccttctg tattttacgg agattattat gggattccaa cacatggagt gccagcaatg     540

agatcaaaaa tcgatccgat tttagaagca cgtcaaaagt atgcatacgg accccagcac     600

gattatcttg accacccgga tgtgatcgga tggacgaggg aaggtgacag ctcccatcct     660

aaatcaggtt tggccacttt aatcacggac ggacccggcg gatcaaagcg gatgtatgcc     720

ggcctgaaaa atgccggcga gacatggtat gacataacgg gcaaccgttc agatactgta     780

aaaatcggat ctgacggctg gggagagttt catgtaaacg atgggtccgt ctccatttat     840

gttcagaaa                                                             849
```